(12) United States Patent
Shanahan et al.

(10) Patent No.: US 8,603,991 B2
(45) Date of Patent: Dec. 10, 2013

(54) INDIVIDUALIZED CANCER THERAPY

(75) Inventors: David Shanahan, Dallas, TX (US); John Nemunaitis, Cedar Hill, TX (US); Neil Senzer, Dallas, TX (US); Phillip Maples, Pilot Point, TX (US); Donald Rao, Dallas, TX (US)

(73) Assignee: Gradalis, Inc., Carrollton, TX (US)

(*) Notice: Subject to any disclaimer, the term of this patent is extended or adjusted under 35 U.S.C. 154(b) by 0 days.

(21) Appl. No.: 11/601,431

(22) Filed: Nov. 17, 2006

(65) Prior Publication Data

US 2007/0248659 A1    Oct. 25, 2007

Related U.S. Application Data

(60) Provisional application No. 60/772,015, filed on Feb. 10, 2006, provisional application No. 60/738,160, filed on Nov. 18, 2005.

(51) Int. Cl.
| | | |
|---|---|---|
| *A61K 31/70* | (2006.01) | |
| *C12Q 1/68* | (2006.01) | |
| *C07H 21/02* | (2006.01) | |
| *C07H 21/04* | (2006.01) | |

(52) U.S. Cl.
USPC .......... 514/44 A; 435/375; 435/377; 435/6.1; 536/24.5

(58) Field of Classification Search
None
See application file for complete search history.

(56) References Cited

U.S. PATENT DOCUMENTS

| | | | |
|---|---|---|---|
| 6,506,559 B1 | 1/2003 | Fire et al. | |
| 2003/0138407 A1 | 7/2003 | Lu et al. | |
| 2003/0148295 A1* | 8/2003 | Wan et al. | 435/6 |
| 2004/0023390 A1 | 2/2004 | Davidson et al. | |
| 2004/0213764 A1 | 10/2004 | Wold et al. | |
| 2004/0241854 A1 | 12/2004 | Davidson et al. | |
| 2005/0043263 A1 | 2/2005 | Giese et al. | |
| 2005/0080031 A1 | 4/2005 | McSwiggen | |
| 2005/0142578 A1 | 6/2005 | Usman et al. | |
| 2005/0143333 A1 | 6/2005 | Richards et al. | |
| 2006/0269518 A1* | 11/2006 | Chang et al. | 424/93.2 |
| 2006/0287260 A1* | 12/2006 | Manoharan et al. | 514/44 |
| 2009/0208514 A1* | 8/2009 | Nakamura et al. | 424/174.1 |

FOREIGN PATENT DOCUMENTS

| | | |
|---|---|---|
| WO | 02/44321 | 6/2002 |
| WO | 02/44321 A2 | 6/2002 |
| WO | 03/006477 | 1/2003 |
| WO | 03/006477 A1 | 1/2003 |

OTHER PUBLICATIONS

Welsh et al. PNAS, 2001, vol. 98, pp. 1176-1181.*
Petricoin et al., Nature Reviews vol. 1:683-695, Sep. 2002.*
Shen et al., Expert Opin. Biol. Ther. vol. 5(11):1427-1441, 2005.*
Shen et al. Expert Opin. Biol. Ther. vol. 5(11):1427-1441, Nov. 1, 2005.*
Carette, Jan E. et al.; *Conditionally Replicating Adenoviruses Expressing Short Hairpin RNAs Silence the Expression of a Target Gene in Cancer Cells*, Cancer Research 64, 2663-2667 (Apr. 15, 2004).
Agrawal, Sudhir, et al., Antisense Therapeutics: Is it as Simple as Complementary Base Recognition?, Molecular Medicine Today, Feb. 2000, vol. 61, pp. 72-83.
Chirila, Trajan V., et al., "The Use of Synthetic Polymers for Delivery of Therapeutic Antisense Oligodeoxynucleotides," Biomaterials, (2002), vol. 23, pp. 321-342.
Crooke, Stanley T., "Progress in Antisense Technology," Annu. Rev. Med., (2004), 55:61-95.
Jang, Jae-Hyung, et al., "Gene Delivery from Polymer Scaffolds for Tissue Engineering," Expert Rev. Medical Devices, (2004), 1(1):127-138.
Opalinska, Joanna B., et al., "Nucleic-Acid Therapeutics: Basic Principles and Recent Applications," Nature, (Jul. 2002, vol. 1, pp. 503-514.
Parco, Zain, et al., "Challenges for RNAi in vivo," Trends in Biotechnology, Aug. 2004, vol. 22, No. 8, pp. 390-394.
Peracchi, Alessio, "Prospects for Antiviral Ribozymes and Deoxyribozymes," Rev. Med. Virol., (2004), vol. 14, pp. 47-64.

\* cited by examiner

*Primary Examiner* — Sean McGarry
(74) *Attorney, Agent, or Firm* — Edwin S. Flores; Chalker Flores, LLP

(57) ABSTRACT

Methods for treating cancer that include (a) obtaining a specimen of cancer issue from a patient; (b) obtaining a specimen of normal tissue in the proximity of the cancer tissue; (c) extracting total protein from the cancer tissue and normal tissue; (d) obtaining a protein expression profile of the cancer tissue and normal tissue; (e) identifying a group of proteins that are expressed in the cancer tissue at significantly different levels than in the normal tissue; (f) identifying one or more prioritized proteins from the group of proteins, which will serve as the target for an RNA interference molecule (RNAi), which, when provided to a patient, will reduce the expression level of the one or more prioritized proteins using both cleavage-dependent and cleavage-independent pathways of the RNA-induced silencing complex (RISC).

10 Claims, 35 Drawing Sheets
(33 of 35 Drawing Sheet(s) Filed in Color)

*Following introduction of RNAi construct, assess perturbation effect using 2D-DIGE and microarray for validation and/or discovery and apply to secondary, tertiary, etc. target selection for multiplex construct.

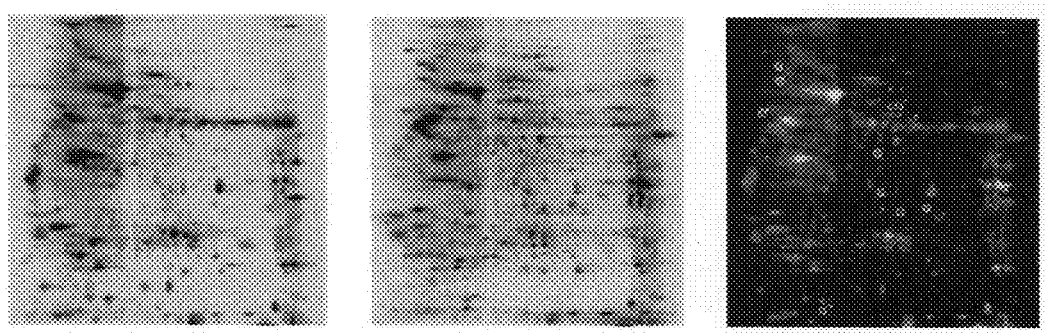
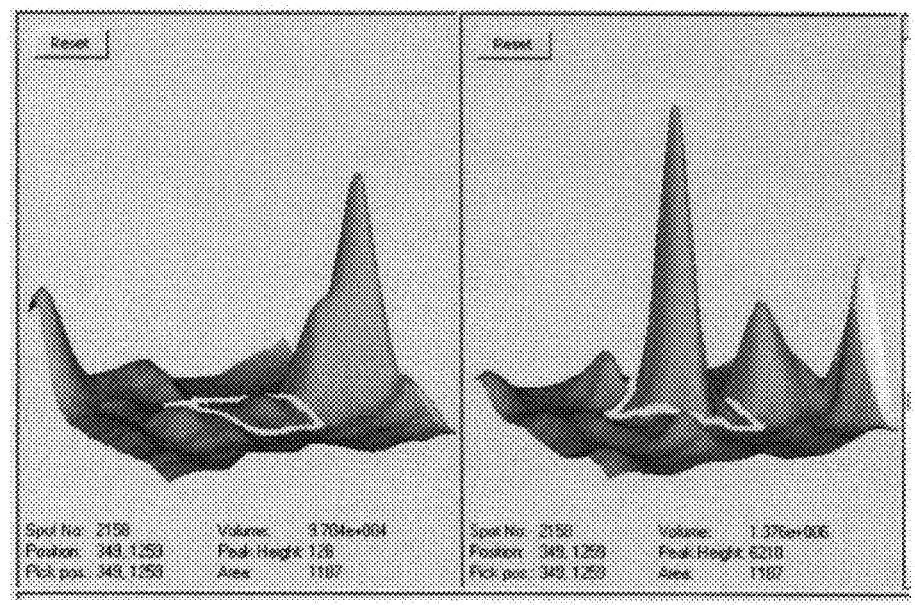
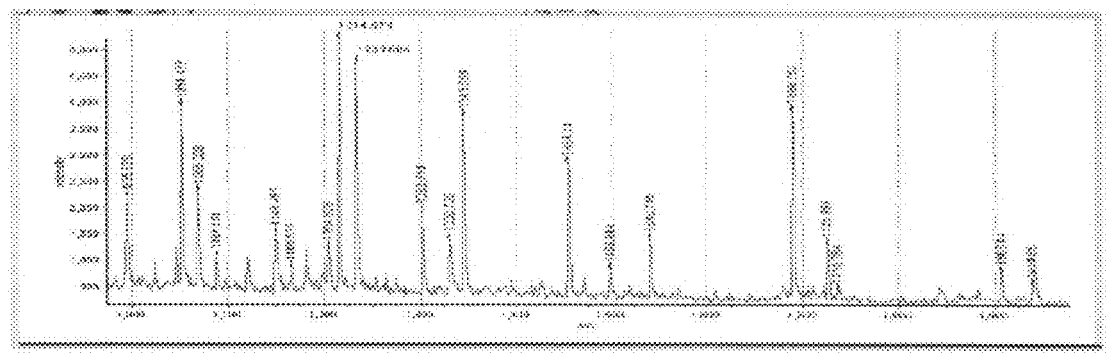
Figure 3

A
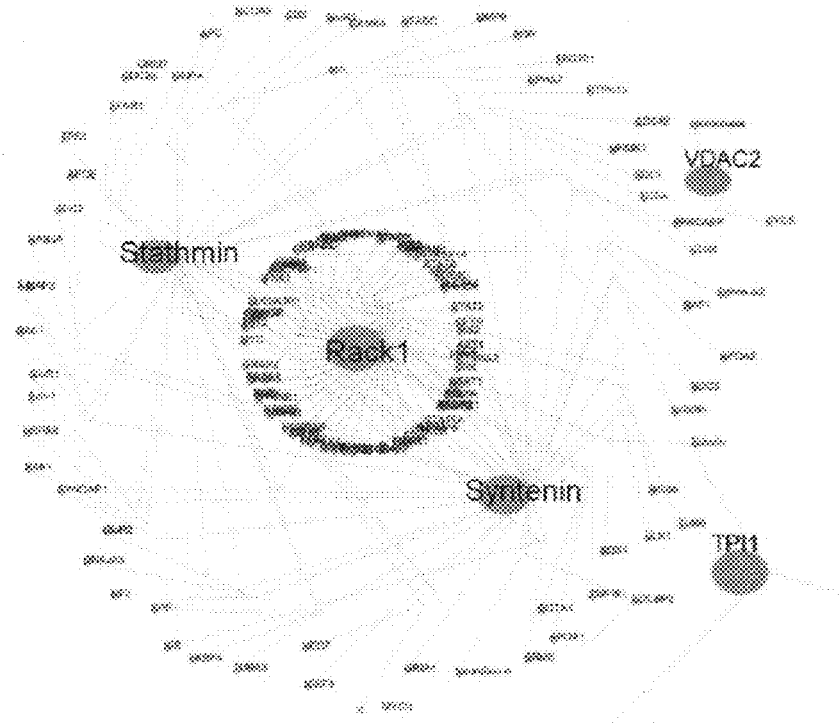
B
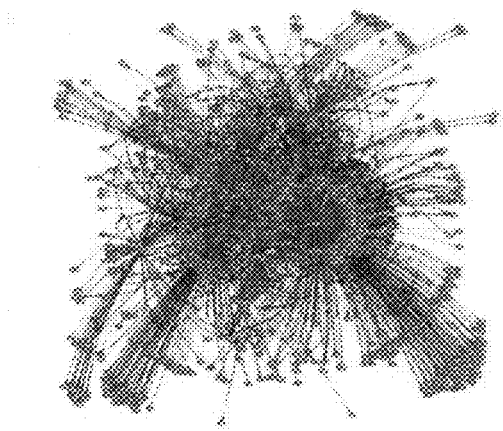
C
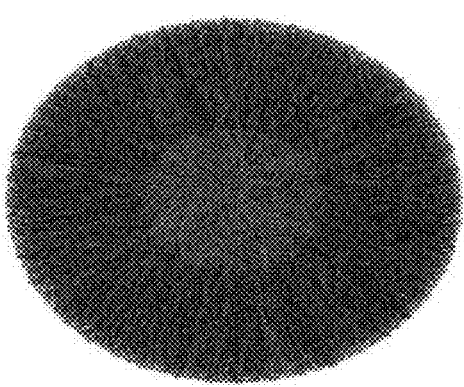
Figure 5

A. Expression of RACK1 in RW tumor and normal tissue
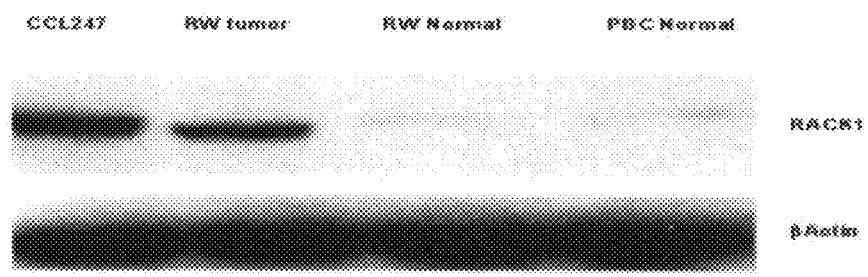
B. siRNA knockdown of RACK1 in cell line CCL247 - >80% at 48hr
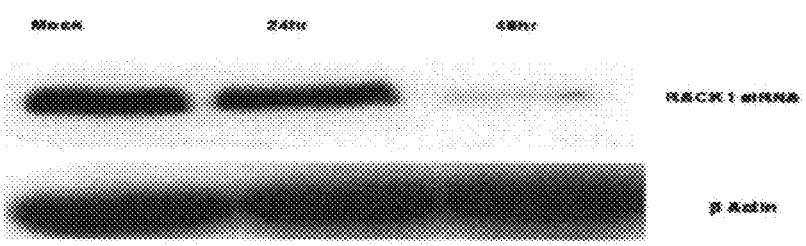
C. Effect of transfection with RACK1 siRNA on cell numbers.
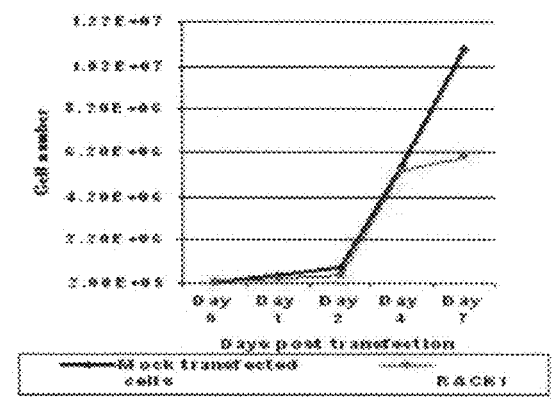
Figure 7

| Protein name | Key Function | Cancer Association | Reference | Protein Malignant/Normal levels (biopsy #1) | mRNA malignant/normal levels (biopsy #1) | DNA cross species preservation percent |
|---|---|---|---|---|---|---|
| Stathmin 1 (Oncoprotein 18) | Cell-cycle regulating protein. Regulates cell migration | SCCHN, Hepatocellular, renal cell, prostate | 54-58 | | | |
| TPI1 | Regulates glucose metabolism | Breast, bladder, prostate | 59-62 | 7.04 | 4.21 | 32.9% amino acid identity with Xenopus tropicalis AAH73451 |
| RACK1 (lung cancer oncogene 7) | A scaffold protein which coordinates multiple intracellular signals associated with cell growth | Colon, pancreas, lung, breast | 63-66 | 3.61 | 1.84 | 33.9% amino acid identity with D. melanogaster AAS77472 |
| Syntenin | Regulates tumor cell growth development and differentiation | Melanoma, breast, gastric cancer | 67-70 | 2.99 | 2.07 | 69.5% amino acid identity with D. melanogaster AAB72148 |
| Voltage-dependent anion channel 2 | Regulates apoptosis | --- | 5,68 | 7.07 | 4.12 | 78.2% amino acid identity with Xenopus tropicalis NP_001006801 |
| | | | | 3.61 | 1.48 | 56.5% amino acid identity with D. melanogaster CAA63413 |

Figure 9

Blue= sense sequence.
Red= anti-sense sequence.
Bold and underlined=mismatches.

Construct 17/18
Sense sequence on the ascending strand; complete match sequence on both strands.
dG = -23.1

AAGGATCCTGCTGTTGACAGTGAGCGCGGCACAAATGGCTGCCAAATAGTGAAGCCACAGA
TGTATTTGGCAGCCATTTGTGCCTTGCCTACTGCCTCGGAAGCTTTG  (SEQ ID NO: 32)

---

Construct 54/18
Sense sequence on the ascending strand; two nucleotide bulge mismatch at the sense strand.
dG = -14.8

AAGGATCCTGCTGTTGACAGTGAGCGCGGCACAAATGATTGCCAAATAGTGAAGCCACAGA
TGTATTTGGCAGCCATTTGTGCCTTGCCTACTGCCTCGGAAGCTTTG  (SEQ ID NO: 33)

---

Construct 55/18
Sense sequence on the ascending strand; two nucleotide bulge mismatch plus one single base mismatches at the sense strand.
dG = -10.9

AAGGATCCTGCTGTTGACAGTGAGCGCGGTACAAATGATTGCCAAATAGTGAAGCCACAGA
TGTATTTGGCAGCCATTTGTGCCTTGCCTACTGCCTCGGAAGCTTTG  (SEQ ID NO: 34)

---

Construct 56/18
Sense sequence on the ascending strand; two nucleotide bulge mismatch plus two single base mismatches at the sense strand.
dG= -7

AAGGATCCTGCTGTTGACAGTGAGCGCGGTACAAATGATTGACAAATAGTGAAGCCACAGA
TGTATTTGGCAGCCATTTGTGCCTTGCCTACTGCCTCGGAAGCTTTG  (SEQ ID NO: 35)

Construct 17/19
Sense sequence on the ascending strand; two nucleotide bulge mismatch at the anti-sense strand.

AAGGATCCTGCTGTTGACAGTGAGCGCGGCACAAATGGCTGCCAAATAGTGAAGCCACAGA
TGTATTTGGCATACATTTGTGCCTTGCCTACTGCCTCGGAAGCTTTG  (SEQ ID NO: 36)

---

Construct 17/20
Sense sequence on the ascending strand; two nucleotide bulge mismatch plus a single base mismatch at anti-sense strand.

AAGGATCCTGCTGTTGACAGTGAGCGCGGCACAAATGGCTGCCAAATAGTGAAGCCACAGA
TGTATTTGACATACATTTGTGCCTTGCCTACTGCCTCGGAAGCTTTG  (SEQ ID NO: 37)

---

Construct 17/21
Sense sequence on the ascending strand; two nucleotide bulge mismatch plus two single base mismatches at anti-sense strand.

AAGGATCCTGCTGTTGACAGTGAGCGCGGCACAAATGGCTGCCAAATAGTGAAGCCACAGA
TGTATTTGACATACATTTATGCCTTGCCTACTGCCTCGGAAGCTTTG  (SEQ ID NO: 38)

---

Construct 15/16
Anti-sense sequence on the ascending strand; complete match sequence on both strands.
dG = -23.0

AAGGATCCTGCTGTTGACAGTGAGCGCTTTGGCAGCCATTTGTGCCTAGTGAAGCCACAGA
TGTAGGCACAAATGGCTGCCAAATTGCCTACTGCCTCGGAAGCTTTG  (SEQ ID NO: 39)

---

Construct 15/22
Anti-sense sequence on the ascending strand; two nucleotide bulge mismatch at the sense strand.

AAGGATCCTGCTGTTGACAGTGAGCGCTTTGGCAGCCATTTGTGCCTAGTGAAGCCACAGA
TGTAGGCACAAATGTATGCCAAATTGCCTACTGCCTCGGAAGCTTTG  (SEQ ID NO: 40)

Figure 10 (Continued)

Construct 15/23
Anti-sense sequence on the ascending strand; two nucleotide bulge mismatch plus one single base mismatch at the sense strand.

AAGGATCCTGCTGTTGACAGTGAGCGCTTTGGCAGCCATTTGTGCCTAGTGAAGCCACAGA
TGTAGGCACAAATGTATGTCAAATTGCCTACTGCCTCGGAAGCTTTG (SEQ ID NO: 41)

---

Construct 15/24
Anti-sense sequence on the ascending strand; two nucleotide bulge mismatch plus two single base mismatches at the sense strand.

AAGGATCCTGCTGTTGACAGTGAGCGCTTTGGCAGCCATTTGTGCCTAGTGAAGCCACAGA
TGTAGGCATAAATGTATGTCAAATTGCCTACTGCCTCGGAAGCTTTG (SEQ ID NO: 42)

Figure 10 (Continued)

(SEQ ID NO: 39)

(SEQ ID NO: 32)

(SEQ ID NO: 33)

(SEQ ID NO: 34)

(SEQ ID NO: 35)

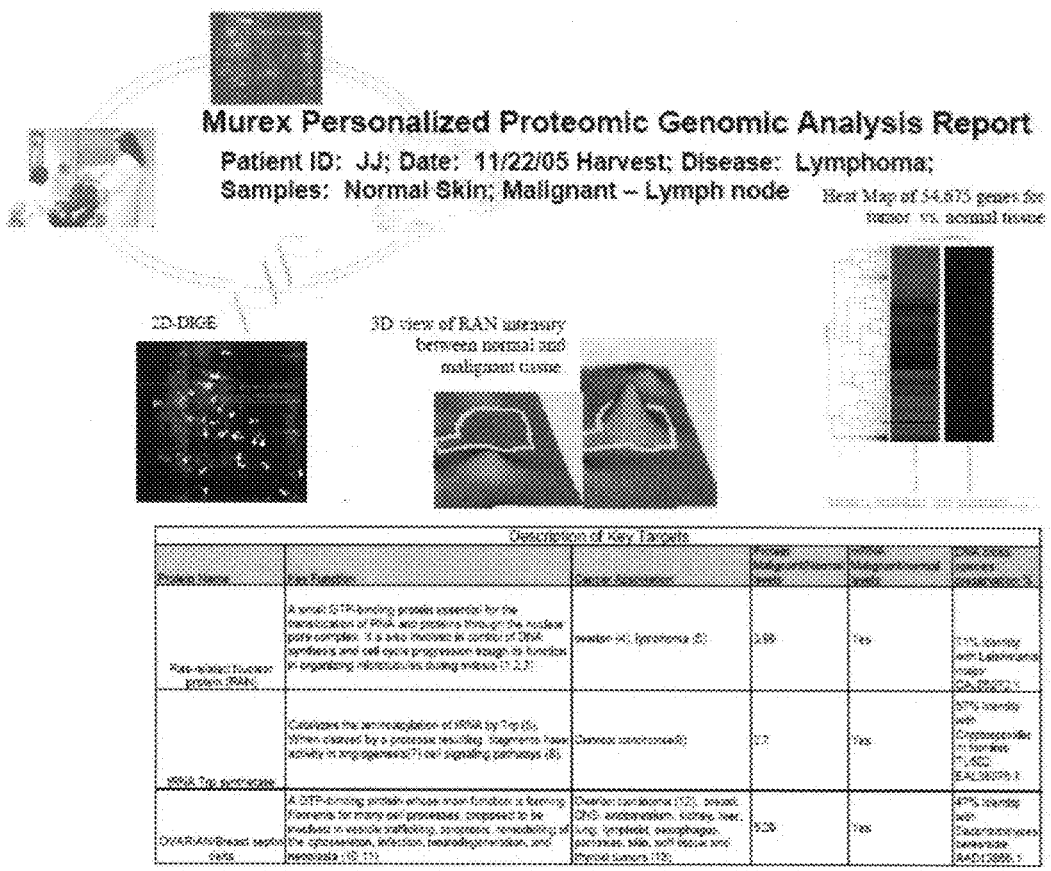
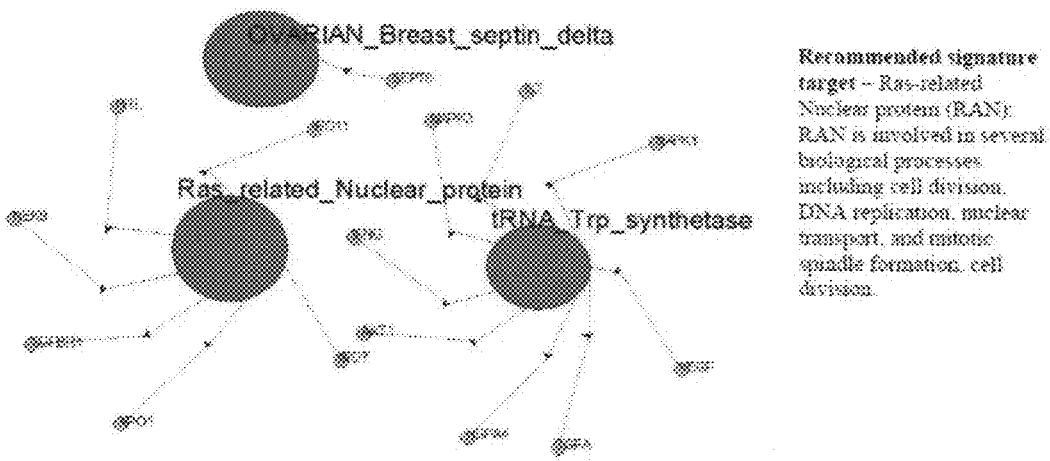
Figure 22C

FIGURE 22F

Murex Personalized Proteomic Genomic Analysis Report
Patient ID: JAG; Date: 2/10/2006 Harvest; Disease: NSCLC;
Samples: Lymph Node; Malignant – Lymph node

| Protein Name | Accession # | Gene ID | Gene Symbol | Gene Title | Key Function | Cancer Association | Protein Malignant/ Normal levels | mRNA Malignant/ normal levels > 1.5 | DNA cross species preservation % |
|---|---|---|---|---|---|---|---|---|---|
| lung cancer oncogene 7 (Homo sapiens) | 37724561 | 10399 | GNB2L1 | guanine nucleotide binding protein (G protein), beta polypeptide 2-like 1 | A ribosomal component (6) and a scaffold protein which coordinates multiple intracellular signals associated with cell growth, proliferation (7, 8, 9, 10, 11), focal adhesions, and motility (12) | Colon (13), pancreas (14), lung, breast (15) | 5.39 | No | 31% identity with Candida albicans BAE44046 1 |
| enolase 1 | 62896593 | 2023 | ENO1 | Enolase 1 | A glycolytic enzyme involved in transcriptional regulation (16). Implicated in the Warburg effect (17). | Breast (18, 19), lymph node, prostate, and brain (17) | 4.16 | Yes | 71% identity with Arabidopsis thaliana CAA4111 4.1 |

Recommended signature target – Lung cancer oncogene 7 (GNB2L1)

6  Ceci M, Gaviraghi C, Gorrini C, Sala LA, Offenhauser N, Marchisio PC, Biffo S. Release of eIF6 (p27BBP) from the 60S subunit allows 80S ribosome assembly. Nature. 2003 Dec 4;426(6966):579-84

7  Yarwood SJ, Steele MR, Scotland G, et al. The RACK1 signaling scaffold protein selectively interacts with the cAMP-specific phosphodiesterase PDE4D5 isoform. J Biol Chem 274:14909-17 1999

8  Hermanto U, Zong CS, Li W, et al. RACK1, an insulin-like growth factor I (IGF-I) receptor-interacting protein, modulates IGF-I-dependent integrin signaling and promotes cell spreading and contact with extracellular matrix. Mol Cell Biol 22:2345-65 2002

9  Usacheva A, Smith R, Minshall R, et al. The WD motif-containing protein receptor for activated protein kinase C (RACK1) is required for recruitment and activation of signal transducer and activator of transcription 1 through the type I interferon receptor. J Biol Chem 276:22948-53 2001

10  Liliental J, Chang DD. Rack1, a receptor for activated protein kinase C, interacts with integrin beta subunit. J Biol Chem 273:2379-83, 1998

11  Chang BY, Conroy KB, Machleder EM, et al. RACK1: a receptor for activated C kinase and a homolog of the beta subunit of G proteins: inhibits activity of src tyrosine kinases and growth of NIH 3T3 cells. Mol Cell Biol 18:3245-56, 1998

12  Besson A, Wilson TL, Yong VW. The anchoring protein RACK1 links protein kinase Cepsilon to integrin beta chains. Requirements for adhesion and motility. J Biol Chem 277:22073-84, 2002

13  Saito A, Fujii G, Sato Y, et al. Detection of genes expressed in primary colon cancers by in situ hybridisation: overexpression of RACK 1. Mol Pathol 55:34-9, 2002

14  Evans JD, Cornford PA, Dodson A, et al. Expression patterns of protein kinase C isoenzymes are characteristically modulated in chronic pancreatitis and pancreatic cancer. Am J Clin Pathol 119:392-402, 2003

15  Berns H, Humar R, Hengerer B, et al. RACK1 is up-regulated in angiogenesis and human carcinomas. Faseb J 14:2549-58, 2000

16  Kim JW, Dang CV. Multifaceted roles of glycolytic enzymes. Trends Biochem Sci. 2005 Mar;30(3):142-50.

17  Altenberg B, Greulich KO. Genes of glycolysis are ubiquitously overexpressed in 24 cancer classes. Genomics. 2004 Dec;84(6):1014-20.

18  Zhang D, Tai LK, Wong LL, Chiu LL, Sethi SK, Koay ES. Proteomic study reveals that proteins involved in metabolic and detoxification pathways are highly expressed in HER-2/neu-positive breast cancer. Mol Cell 19  Somiari RI, Sullivan A, Russell S, Somiari S, Hu H, Jordan R, George A, Katenhusen R, Buchowiecka A, Arciero C, Brzeski H, Hooke J, Shriver C. High-throughput proteomic analysis of human infiltrating ductal carcinoma of the

FIGURE 22G

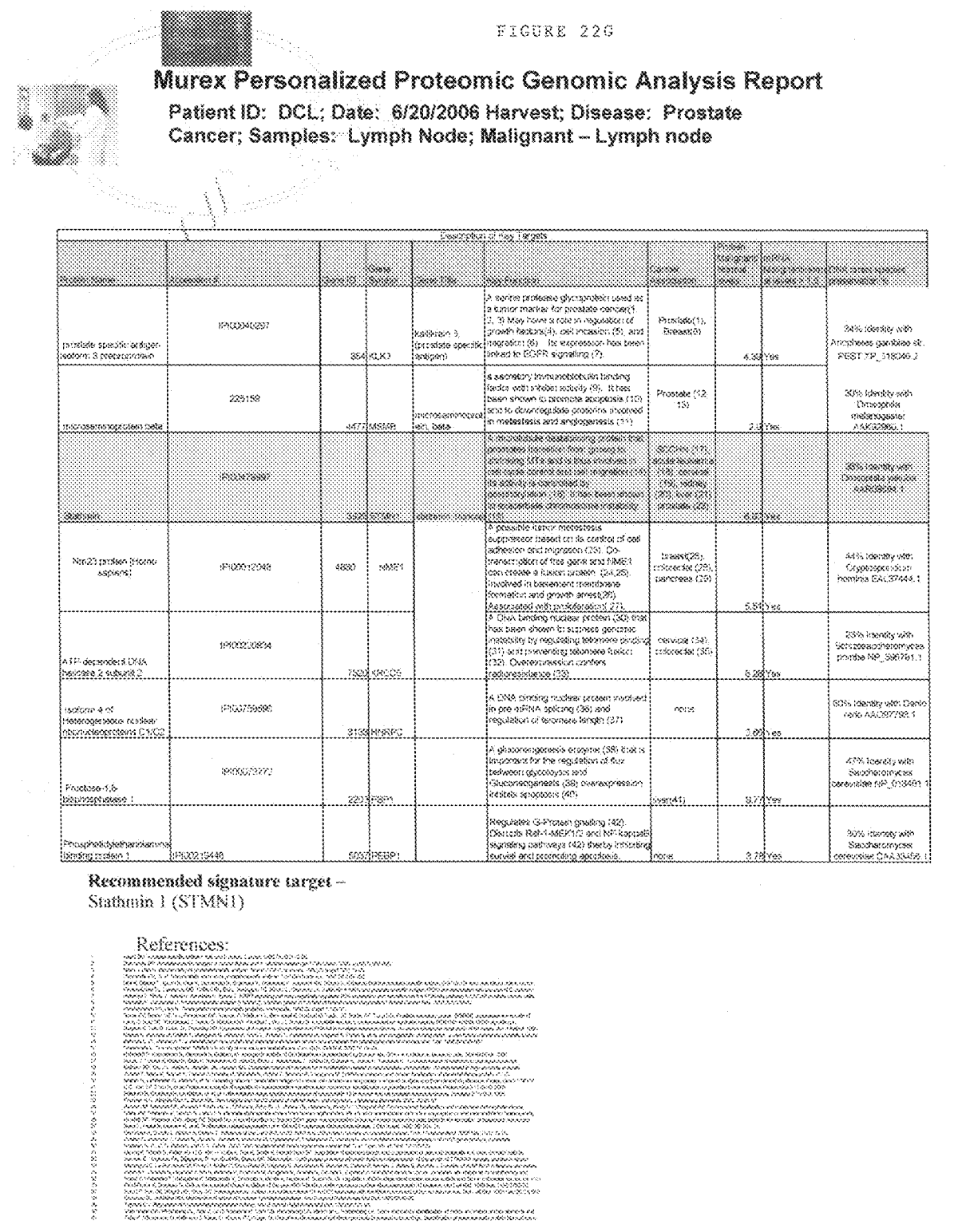

Murex Personalized Proteomic Genomic Analysis Report
Patient ID: DCL; Date: 6/20/2006 Harvest; Disease: Prostate
Cancer; Samples: Lymph Node; Malignant – Lymph node Recommended signature target –
Stathmin 1 (STMN1)

References:

SEQUENCE LISTING

<160> NUMBER OF SEQ ID NOS: 42

<210> SEQ ID NO 1
<211> LENGTH: 20
<212> TYPE: DNA
<213> ORGANISM: Artificial
<220> FEATURE:
<223> OTHER INFORMATION: Gene-specific PCR primer used for cloning

<400> SEQUENCE: 1
tatggcagga aaggatgagg                                           20

<210> SEQ ID NO 2
<211> LENGTH: 29
<212> TYPE: DNA
<213> ORGANISM: Artificial
<220> FEATURE:

-continued

<223> OTHER INFORMATION: Gene specific PCR primer for cDNA cloning

<400> SEQUENCE: 2
atcagatctt ctgtttggcg cttttgtgc                               29

<210> SEQ ID NO 3
<211> LENGTH: 31
<212> TYPE: DNA
<213> ORGANISM: Artificial
<220> FEATURE:
<223> OTHER INFORMATION: Gene specific PCR primer for cDNA cloning

<400> SEQUENCE: 3
atggctagcc acgcttgtgc ttttaatctg c                            31

<210> SEQ ID NO 4
<211> LENGTH: 21
<212> TYPE: DNA
<213> ORGANISM: Artificial
<220> FEATURE:
<223> OTHER INFORMATION: Sense strand of STMN1 siRNA

<400> SEQUENCE: 4
ggcacaaaug gcugccaaat t                                       21

<210> SEQ ID NO 5
<211> LENGTH: 21
<212> TYPE: DNA
<213> ORGANISM: Artificial
<220> FEATURE:
<223> OTHER INFORMATION: Antisense strand of STMN1 siRNA

<400> SEQUENCE: 5
uuuggcagcc auuugugcct c                                       21

<210> SEQ ID NO 6
<211> LENGTH: 22
<212> TYPE: DNA
<213> ORGANISM: Artificial
<220> FEATURE:
<223> OTHER INFORMATION: psiTEST Forward PCR Primer

<400> SEQUENCE: 6
agaccttcat agcgcacgtc at                                      22

<210> SEQ ID NO 7
<211> LENGTH: 20
<212> TYPE: DNA
<213> ORGANISM: Artificial
<220> FEATURE:
<223> OTHER INFORMATION: psiTEST Reverse PCR primer

<400> SEQUENCE: 7
cctccccctg aacctgaaac                                         20

<210> SEQ ID NO 8
<211> LENGTH: 18
<212> TYPE: DNA
<213> ORGANISM: Artificial
<220> FEATURE:
<223> OTHER INFORMATION: pSilencer Reverse PCR primer

<400> SEQUENCE: 8
aggcgattaa gttgggta                                           18

<210> SEQ ID NO 9

```
<211> LENGTH: 18
<212> TYPE: DNA
<213> ORGANISM: Artificial
<220> FEATURE:
<223> OTHER INFORMATION: pSilencer Reverse PCR Primer

<400> SEQUENCE: 9
cggtaggcgt gtacggtg                                                     18

<210> SEQ ID NO 10
<211> LENGTH: 63
<212> TYPE: DNA
<213> ORGANISM: Artificial
<220> FEATURE:
<223> OTHER INFORMATION: shRNA-encoding sequence

<400> SEQUENCE: 10
aaggatcctg ctgttgacag tgagcgcttt ggcagccatt tgtgcctagt gaagccacag        60
atg                                                                     63

<210> SEQ ID NO 11
<211> LENGTH: 60
<212> TYPE: DNA
<213> ORGANISM: Artificial
<220> FEATURE:
<223> OTHER INFORMATION: shRNA-encoding sequence

<400> SEQUENCE: 11
caaagcttcc gaggcagtag gcaatttggc agccatttgt gcctacatct gtggcttcac        60

<210> SEQ ID NO 12
<211> LENGTH: 63
<212> TYPE: DNA
<213> ORGANISM: Artificial
<220> FEATURE:
<223> OTHER INFORMATION: shRNA-encoding sequence

<400> SEQUENCE: 12
aaggatcctg ctgttgacag tgagcgcggc acaaatggct gccaaatagt gaagccacag        60
atg                                                                     63

<210> SEQ ID NO 13
<211> LENGTH: 60
<212> TYPE: DNA
<213> ORGANISM: Artificial
<220> FEATURE:
<223> OTHER INFORMATION: shRNA-encoding sequence

<400> SEQUENCE: 13
caaagcttcc gaggcagtag gcaaggcaca aatggctgcc aaatacatct gtggcttcac        60

<210> SEQ ID NO 14
<211> LENGTH: 60
<212> TYPE: DNA
<213> ORGANISM: Artificial
<220> FEATURE:
<223> OTHER INFORMATION: shRNA-encoding sequence

<400> SEQUENCE: 14
caaagcttcc gaggcagtag gcaaggcaca aatgtatgcc aaatacatct gtggcttcac        60

<210> SEQ ID NO 15
<211> LENGTH: 60
<212> TYPE: DNA
<213> ORGANISM: Artificial
<220> FEATURE:
```

<223> OTHER INFORMATION: shRNA-encoding sequence

<400> SEQUENCE: 15
caaagcttcc gaggcagtag gcaaggcaca aatgtatgtc aaatacatct gtggcttcac    60

<210> SEQ ID NO 16
<211> LENGTH: 60
<212> TYPE: DNA
<213> ORGANISM: Artificial
<220> FEATURE:
<223> OTHER INFORMATION: shRNA-encoding sequence

<400> SEQUENCE: 16
caaagcttcc gaggcagtag gcaaggcata aatgtatgtc aaatacatct gtggcttcac    60

<210> SEQ ID NO 17
<211> LENGTH: 60
<212> TYPE: DNA
<213> ORGANISM: Artificial
<220> FEATURE:
<223> OTHER INFORMATION: shRNA-encoding sequence

<400> SEQUENCE: 17
caaagcttcc gaggcagtag gcaatttggc atacatttgt gcctacatct gtggcttcac    60

<210> SEQ ID NO 18
<211> LENGTH: 60
<212> TYPE: DNA
<213> ORGANISM: Artificial
<220> FEATURE:
<223> OTHER INFORMATION: shRNA-encoding sequence

<400> SEQUENCE: 18
caaagcttcc gaggcagtag gcaatttgac atacatttgt gcctacatct gtggcttcac    60

<210> SEQ ID NO 19
<211> LENGTH: 60
<212> TYPE: DNA
<213> ORGANISM: Artificial
<220> FEATURE:
<223> OTHER INFORMATION: shRNA-encoding sequence

<400> SEQUENCE: 19
caaagcttcc gaggcagtag gcaatttgac atacatttat gcctacatct gtggcttcac    60

<210> SEQ ID NO 20
<211> LENGTH: 63
<212> TYPE: DNA
<213> ORGANISM: Artificial
<220> FEATURE:
<223> OTHER INFORMATION: shRNA-encoding sequence

<400> SEQUENCE: 20
aaggatcctg ctgttgacag tgagcgcggc acaaatgatt gccaaatagt gaagccacag    60
atg                                                                  63

<210> SEQ ID NO 21
<211> LENGTH: 63
<212> TYPE: DNA
<213> ORGANISM: Artificial
<220> FEATURE:
<223> OTHER INFORMATION: shRNA-encoding sequence

<400> SEQUENCE: 21
aaggatcctg ctgttgacag tgagcgcggt acaaatgatt gccaaatagt gaagccacag    60

| atg | 63 |

<210> SEQ ID NO 22
<211> LENGTH: 63
<212> TYPE: DNA
<213> ORGANISM: Artificial
<220> FEATURE:
<223> OTHER INFORMATION: shRNA-encoding sequence

<400> SEQUENCE: 22

| aaggatcctg ctgttgacag tgagcgcggt acaaatgatt gacaaatagt gaagccacag | 60 |
| atg | 63 |

<210> SEQ ID NO 23
<211> LENGTH: 21
<212> TYPE: DNA
<213> ORGANISM: Artificial
<220> FEATURE:
<223> OTHER INFORMATION: Sense strand of RACK1 siRNA

<400> SEQUENCE: 23

| ccuuuacacg cuagauggut t | 21 |

<210> SEQ ID NO 24
<211> LENGTH: 21
<212> TYPE: DNA
<213> ORGANISM: Artificial
<220> FEATURE:
<223> OTHER INFORMATION: Antisense strand of RACK1 siRNA

<400> SEQUENCE: 24

| accaucuagc guguaaaggt g | 21 |

<210> SEQ ID NO 25
<211> LENGTH: 1125
<212> TYPE: DNA
<213> ORGANISM: Homo sapiens

<400> SEQUENCE: 25

| ctctctttca ctgcaaggcg gcggcaggag aggttgtggt gctagtttct ctaagccatc | 60 |
| cagtgccatc ctcgtcgctg cagcgacaca cgctctcgcc gccgccatga ctgagcagat | 120 |
| gacccttcgt ggcaccctca agggccacaa cggctgggta acccgatcg ctactacccc | 180 |
| gcagttcccg gacatgatcc tctccgcctc tcgagataag accatcatca tgtggaaact | 240 |
| gaccagggat gagaccaact atggaattcc acagcgtgct ctgcggggtc actcccactt | 300 |
| tgttagtgat gtggttatct cctcagatgg ccagtttgcc ctctcaggct cctgggatgg | 360 |
| aacccctgcgc ctctgggatc tcacaacggg caccaccacg aggcgatttg tgggccatac | 420 |
| caaggatgtg ctgagtgtgg ccttctcctc tgacaaccgg cagattgtct ctggatctcg | 480 |
| agataaaacc atcaagctat ggaatacct gggtgtgtgc aaatacactg tccaggatga | 540 |
| gagccactca gagtgggtgt cttgtgtccg cttctcgccc aacagcagca accctatcat | 600 |
| cgtctcctgt ggctgggaca agctggtcaa ggtatgaac ctggctaact gcaagctgaa | 660 |
| gaccaaccac attggccaca caggctatct gaacacggtg actgtctctc cagatggatc | 720 |
| cctctgtgct tctggaggca aggatggcca ggccatgtta tgggatctca cgaaggcaa | 780 |
| acacctttac acgctagatg gtgggacat catcaacgcc ctgtgcttca gccctaaccg | 840 |
| ctactggctg tgtgctgcca caggccccag catcaagatc tgggatttag agggaaagat | 900 |
| cattgtagat gaactgaagc aagaagttat cagtaccagc agcaaggcag aaccaccca | 960 |

-continued

| | |
|---|---|
| gtgcacctcc ctggcctggt ctgctgatgg ccagactctg tttgctggct acacggacaa | 1020 |
| cctggtgcga gtgtggcagg tgaccattgg cacacgctag aagtttatgg cagagcttta | 1080 |
| caaataaaaa aaaaactggc tttctgaca aaaaaaaaaa aaaaa | 1125 |

<210> SEQ ID NO 26
<211> LENGTH: 2173
<212> TYPE: DNA
<213> ORGANISM: Homo sapiens

<400> SEQUENCE: 26

| | |
|---|---|
| ggctgaaggc gggggcggtg ccatgacgcg cctcggggc ggtcctcggg cgcgcaccgc | 60 |
| tctcttacac tcgggcctca gaagtccgtg ccagtgaccg gaggcggcgg cggcgagcgg | 120 |
| ttccttgtgg gctagaagaa tcctgcaaaa atgtctctct atccatctct cgaagacttg | 180 |
| aaggtagaca aagtaattca ggctcaaact gcttttttctg caaaccctgc caatccagca | 240 |
| attttgtcag aagcttctgc tcctatccct cacgatggaa atctctatcc cagactgtat | 300 |
| ccagagctct ctcaatacat ggggctgagt ttaaatgaag aagaaatacg tgcaaatgtg | 360 |
| gccgtggttt ctggtgcacc acttcagggg cagttggtag caagaccttc cagtataaac | 420 |
| tatatggtgg ctcctgtaac tggtaatgat gttggaattc gtagagcaga aattaagcaa | 480 |
| gggattcgtg aagtcatttt tgtgtaagga tcaagatgga aaattggact caggcttaaa | 540 |
| tcaatagata atggtatatt tgttcagcta gtccaggcta attctccagc ctcattggtt | 600 |
| ggtctgagat ttggggacca agtacttcag atcaatggtg aaaactgtgc aggatggagc | 660 |
| tctgataaag cgcacaaggt gctcaaacag gcttttggag agaagattac catgaccatt | 720 |
| cgtgacaggc cctttgaacg gacgattacc atgcataagg atagcactgg acatgttggt | 780 |
| tttatctta aaaatggaaa aataacatcc atagtgaaag atagctctgc agccagaaat | 840 |
| ggtcttctca cggaacataa catctgtgaa atcaatggac agaatgtcat tggattgaag | 900 |
| gactctcaaa ttgcagacat actgtcaaca tctgggactg tagttactat tacaatcatg | 960 |
| cctgctttta tctttgaaca tattattaag cggatggcac caagcattat gaaaagccta | 1020 |
| atggaccaca ccattcctga ggtttaaaat tcacggcacc atggaaatgt agctgaacgt | 1080 |
| ctccagtttc cttctttggc aacttctgta ttatgcacgt gaagccttcc cggagccagc | 1140 |
| gagcatatgc tgcatgagga ccttttctatc ttacattatg gctgggaatc ttactctttc | 1200 |
| atctgatacc ttgttcagat ttcaaaatag ttgtagcctt atcctggttt tacagatgtg | 1260 |
| aaactttcaa gagatttact gactttccta gaatagtttc tctactggaa acctgatgct | 1320 |
| tttataagcc attgtgatta ggatgactgt tacaggctta gctttgtgtg aaaaccagtc | 1380 |
| acctttctcc taggtaatga gtagtgctgt tcatattact ttagttctat agcatacttg | 1440 |
| catctttaac atgctatcat agtacattta gaatgattgc ctttgatttt ttttttaaat | 1500 |
| tctgtgtgtg tgtgtgtaaa atgccaatta agaacactgg tttcattcca tgtaagcatt | 1560 |
| aaacagtgta tgtaggtttc aagagattgt gatgattctt aaattttaac taccttcact | 1620 |
| taatatgctt gaactgtcgc cttaactatg ttaagcatct agactaaaag ccaaaatata | 1680 |
| attattgctg cctttctaaa aacccaaaat gtagttctct attaacctga aatgtacact | 1740 |
| agcccagaac agtttaatgg tacttactga gctatagcat agctgcttag ttgtttttga | 1800 |
| gattttttag tcaacacata atggaaactt cttttcttcta aaagttgcca gtgccacttt | 1860 |
| taagaagtga atcactatat gtgatgtaaa agttattaca ctaaacagga taaacttttg | 1920 |
| actcccctt tgttcatttg tggattaagt ggtataatac ttaattttgg catttgactc | 1980 |

```
ttaagattat gtaacctagc tactttggga tggtcttaga atattttct gataacttgt    2040 tcctttcct gactcctcct tgcaaacaaa atgatagttg acactttatc ctgattttt     2100 tcttctttt ggtttatgtc tattctaatt aaatatgtat aaataaagtt acattttagt   2160
ctgtctaaaa aaa                                                      2173

<210> SEQ ID NO 27
<211> LENGTH: 1542
<212> TYPE: DNA
<213> ORGANISM: Homo sapiens

<400> SEQUENCE: 27
gctctcggcc aatgcggagc cccgcgcgga ggtcacgtgc ctctgtttgg cgcttttgtg    60
cgcgcccggg tctgttggtg ctcagagtgt ggtcaggcgg ctcggactga gcaggacttt   120
ccttatccca gttgattgtg cagaatacac tgcctgtcgc ttgtcttcta ttcaccatgg   180
cttcttctga tatccaggtg aaagaactgg agaagcgtgc ctcaggccag gcttttgagc   240
tgattctcag ccctcggtca aaagaatctg ttccagaatt ccccctttcc cctccaaaga   300
agaaggatct ttccctggag gaaattcaga gaaattaga agctgcagaa gaaagacgca   360
agtcccatga agctgaggtc ttgaagcagc tggctgagaa acgagagcac gagaaagaag   420
tgcttcagaa ggcaatagaa gagaacaaca acttcagtaa aatggcagaa gagaaactga   480
cccacaaaat ggaagctaat aaagagaacc gagaggcaca aatggctgcc aaactggaac   540
gtttgcgaga gaaggataag cacattgaag aagtgcggaa gaacaaagaa tccaaagacc   600 tgctgacga gactgaagct gactaatttg ttctgagaac tgactttctc cccatcccct    660
tcctaaatat ccaaagactg tactggccag tgtcatttta ttttttccct cctgacaaat   720 atttagaag ctaatgtagg actgtatagg tagatccaga tccagactgt aagatgttgt    780
tttaggggct aaaggggaga aactgaaagt gttttactct ttttctaaag tgttggtctt    840
tctaatgtag ctatttttct tgttgcatct tttctacttc agtacacttg gtgtactggg   900
ttaatggcta gtactgtatt ggctctgtga aaacatattt gtgaaaagag tatgtagtgg   960
cttcttttga actgttagat gctgaatatc tgttcacttt tcaatcccaa ttctgtccca   1020
atcttaccag atgctactgg acttgaatgg ttaataaaac tgcacagtgc tgttggtggc   1080
agtgacttct tttgagttag gttaataaat caagcccatag agcccctcct ggttgatact   1140
tgttccagat ggggcctttg gggctggtag aaataccca cgcacaaatg accgcacgtt   1200
ctctgccccg tttcttgccc cagtgtggtt tgcattgtct ccttccacaa tgactgctttt  1260 gtttggatgc ctcagcccag gtcagctgtt actttctttc agatgtttat ttgcaaacaa   1320 ccatttttg ttctgtgtcc cttttaaaag gcagattaaa agcacaagcg tgtttctaga   1380
gaacagttga gagagaatct caagattcta cttggtggtt tgcttgctct acgttacagg   1440
tggggcatgt cctcatcctt tcctgccata aaagctatga cacgagaatc agaatattaa   1500 taaaactta tgtactgctg tagcaaaaaa aaaaaaaaaa aa                      1542

<210> SEQ ID NO 28
<211> LENGTH: 21
<212> TYPE: DNA
<213> ORGANISM: Artificial
<220> FEATURE:
<223> OTHER INFORMATION: Sense strand of Stathmin 1 siRNA

<400> SEQUENCE: 28
ggcacaaaug gcugccaaat t                                              21
```

```
<210> SEQ ID NO 29
<211> LENGTH: 21
<212> TYPE: DNA
<213> ORGANISM: Artificial
<220> FEATURE:
<223> OTHER INFORMATION: Anti-sense strand of Stathmin 1 siRNA

<400> SEQUENCE: 29
uuuggcagcc auuugugcct c                                             21

<210> SEQ ID NO 30
<211> LENGTH: 21
<212> TYPE: DNA
<213> ORGANISM: Artificial
<220> FEATURE:
<223> OTHER INFORMATION: Sense strand of Syntenin siRNA

<400> SEQUENCE: 30
gcuauagcau agcugcuuat t                                             21

<210> SEQ ID NO 31
<211> LENGTH: 21
<212> TYPE: DNA
<213> ORGANISM: Artificial
<220> FEATURE:
<223> OTHER INFORMATION: Anti-sense strand of Syntenin siRNA

<400> SEQUENCE: 31
uaagcagcua ugcuauagct c                                             21

<210> SEQ ID NO 32
<211> LENGTH: 108
<212> TYPE: DNA
<213> ORGANISM: Artificial
<220> FEATURE:
<223> OTHER INFORMATION: shRNA-encoding sequence

<400> SEQUENCE: 32
aaggatcctg ctgttgacag tgagcgcggc acaaatggct gccaaatagt gaagccacag     60
atgtatttgg cagccatttg tgccttgcct actgcctcgg aagctttg                108

<210> SEQ ID NO 33
<211> LENGTH: 108
<212> TYPE: DNA
<213> ORGANISM: Artificial
<220> FEATURE:
<223> OTHER INFORMATION: shRNA-encoding sequence

<400> SEQUENCE: 33
aaggatcctg ctgttgacag tgagcgcggc acaaatgatt gccaaatagt gaagccacag     60
atgtatttgg cagccatttg tgccttgcct actgcctcgg aagctttg                108

<210> SEQ ID NO 34
<211> LENGTH: 108
<212> TYPE: DNA
<213> ORGANISM: Artificial
<220> FEATURE:
<223> OTHER INFORMATION: shRNA-encoding sequence

<400> SEQUENCE: 34
aaggatcctg ctgttgacag tgagcgcggt acaaatgatt gccaaatagt gaagccacag     60
atgtatttgg cagccatttg tgccttgcct actgcctcgg aagctttg                108

<210> SEQ ID NO 35
```

```
<211> LENGTH: 108
<212> TYPE: DNA
<213> ORGANISM: Artificial
<220> FEATURE:
<223> OTHER INFORMATION: shRNA-encoding sequence

<400> SEQUENCE: 35
aaggatcctg ctgttgacag tgagcgcggt acaaatgatt gacaaatagt gaagccacag      60
atgtatttgg cagccatttg tgccttgcct actgcctcgg aagctttg                  108

<210> SEQ ID NO 36
<211> LENGTH: 108
<212> TYPE: DNA
<213> ORGANISM: Artificial
<220> FEATURE:
<223> OTHER INFORMATION: shRNA-encoding sequence

<400> SEQUENCE: 36
aaggatcctg ctgttgacag tgagcgcggc acaaatggct gccaaatagt gaagccacag      60
atgtatttgg catacatttg tgccttgcct actgcctcgg aagctttg                  108

<210> SEQ ID NO 37
<211> LENGTH: 108
<212> TYPE: DNA
<213> ORGANISM: Artificial
<220> FEATURE:
<223> OTHER INFORMATION: shRNA-encoding sequence

<400> SEQUENCE: 37
aaggatcctg ctgttgacag tgagcgcggc acaaatggct gccaaatagt gaagccacag      60
atgtatttga catacatttg tgccttgcct actgcctcgg aagctttg                  108

<210> SEQ ID NO 38
<211> LENGTH: 108
<212> TYPE: DNA
<213> ORGANISM: Artificial
<220> FEATURE:
<223> OTHER INFORMATION: shRNA-encoding sequence

<400> SEQUENCE: 38
aaggatcctg ctgttgacag tgagcgcggc acaaatggct gccaaatagt gaagccacag      60
atgtatttga catacattta tgccttgcct actgcctcgg aagctttg                  108

<210> SEQ ID NO 39
<211> LENGTH: 108
<212> TYPE: DNA
<213> ORGANISM: Artificial
<220> FEATURE:
<223> OTHER INFORMATION: shRNA-encoding sequence

<400> SEQUENCE: 39
aaggatcctg ctgttgacag tgagcgcttt ggcagccatt tgtgcctagt gaagccacag      60
atgtaggcac aaatggctgc caaattgcct actgcctcgg aagctttg                  108

<210> SEQ ID NO 40
<211> LENGTH: 108
<212> TYPE: DNA
<213> ORGANISM: Artificial
<220> FEATURE:
<223> OTHER INFORMATION: shRNA-encoding sequence

<400> SEQUENCE: 40
aaggatcctg ctgttgacag tgagcgcttt ggcagccatt tgtgcctagt gaagccacag      60
```

```
-continued atgtaggcac aaatgtatgc caaattgcct actgcctcgg aagctttg                108

<210> SEQ ID NO 41
<211> LENGTH: 108
<212> TYPE: DNA
<213> ORGANISM: Artificial
<220> FEATURE:
<223> OTHER INFORMATION: shRNA-encoding sequence

<400> SEQUENCE: 41
aaggatcctg ctgttgacag tgagcgcttt ggcagccatt tgtgcctagt gaagccacag   60
atgtaggcac aaatgtatgt caaattgcct actgcctcgg aagctttg               108

<210> SEQ ID NO 42
<211> LENGTH: 108
<212> TYPE: DNA
<213> ORGANISM: Artificial
<220> FEATURE:
<223> OTHER INFORMATION: shRNA-encoding sequence

<400> SEQUENCE: 42
aaggatcctg ctgttgacag tgagcgcttt ggcagccatt tgtgcctagt gaagccacag   60
atgtaggcat aaatgtatgt caaattgcct actgcctcgg aagctttg               108
```

INDIVIDUALIZED CANCER THERAPY

CROSS-REFERENCE TO RELATED APPLICATIONS

This application claims priority to, and incorporates by reference, U.S. provisional patent application Ser. No. 60/772,015, filed Feb. 10, 2006, and U.S. provisional patent application Ser. No. 60/738,160, filed Nov. 18, 2005.

FIELD OF THE INVENTION

The field of the invention relates to cancer therapy and, more specifically, to compositions and methods for diagnosing, treating, and monitoring cancer in an individual patient. In addition, the invention relates to compositions and methods for patient-specific cancer genomic/proteomic analysis, genetic network inference, prediction of large-impact key network connector nodes, node-targeted patient-specific treatment, and integrated clinical and post-perturbation loss-of-function assessment in an individual cancer patient.

BACKGROUND OF THE INVENTION

While modern chemotherapeutic drugs provide patients with an established but variable and non-predictable means of combating cancer growth, invasion and metastasis, such drugs have significant limitations and drawbacks. For example, it is well-known that modern chemotherapeutic drugs are generally non-specific in their mechanism of action. That is, such drugs are non-discriminatory in that they preferentially target proliferating over quiescent cells—rather than cancer over normal cells. It is therefore not surprising that traditional chemotherapeutics have compromised efficacy due to the narrow window between therapeutically-effective and toxicity-producing concentrations.

Using rapidly emerging technologies and associated methodologies developed over the last decade, research efforts have actively pursued the development of agents that target specific abnormal genes, cancer phenotype-related amplified genes, and over-expressed oncogene proteins commonly found in human tumors. These methods may be roughly divided into 2 classes: 1) monoclonal antibodies and/or small molecule inhibitors targeted against the inappropriately expressed or over-expressed protein (e.g., tyrosine kinase inhibitors, farnesyltransferase inhibitors, etc.) and 2) manipulations of the transcriptosome machinery itself to suppress the production of these proteins (e.g., antisense, siRNAs, etc.). The second method, that of actually altering production of the oncogene product, for example, entails specific gene-silencing via suppression of expression levels of targeted mRNA or modulation of the stability and/or translational activity of targeted mRNA.

While targeted therapies have demonstrated efficacy in both pre-clinical and clinical applications, such approaches have exhibited significant limitations. The drawbacks of such approaches are caused by the robustness of the co-opted cancer biome. Indeed, cancer cell proliferation and survival is not the result of single, linear protein interactions, but rather the result of interconnected network pathways (with multiple feedback loops) of protein/gene activation. The robustness of this system endows the cancer with functional stability. Therefore, it is not surprising that interventions against a random single cellular target would have only limited effect on the malignant phenotype. That is, despite the application of targeted therapeutics in patients with gene amplification and/or over-expressed protein kinases, for example HER 2 and EGFR, respectively, the presence of functional redundancy in a robust cancer pathway network (from the genome through the proteome and metabalome, inclusively) is likely to "buffer" the effect of random single gene or protein-product knock-out on the malignant process.

In addition, nearly 200,000 possible protein signals and 50,000 mRNA signals are known to be operating in any given cancer cell, and an expanding number of ncRNAs (non-coding RNAs) are being reported that modulate the cancer process by promoter selection, alternate splicing, RNA editing and mRNA stability. These signals are largely independent of cancer morphology and are reformatted as modified vectored edges (links) in an evolved co-opted hierarchical modular power law network which, by the very nature of its robustness, expose fragile critical molecular pathways on which cancer cell proliferation and survival depend.

In light of the foregoing, there is a demand for a process that enables the selection of such fragile pathway (signature) signals unique to the cancer cells in an individual patient. Such process would allow for selectively effective therapeutic management of the patient or patient populations (with similar signals). Still further, there is a demand for compositions and methods that enable physicians to target and modulate the expression of malfunctioning genes and destroy the cancer cells harboring the same (as opposed to merely targeting and destroying proliferating cells) that are implicated in the molecular pathways that are critical to cancer cell survival and/or proliferation. Preferably, such compositions and methods are tailored to the unique, abnormal gene expression identified in the cancer cells of each individual patient.

SUMMARY OF THE INVENTION

According to a first embodiment of the present invention, methods for treating cancer are provided, which comprise (a) obtaining a specimen of cancer tissue from a patient; (b) obtaining a specimen of normal tissue in the proximity of the cancer tissue from such patient; (c) extracting total protein and RNA from the cancer tissue and normal tissue; (d) obtaining a proteomic profile of the cancer tissue and normal tissue using 2D difference in-gel electrophoresis/mass spectrometry (2D-DIGE/MS); (e) identifying proteins that are over-expressed in such cancer tissue compared to normal tissue; (f) obtaining a normalized genomic profile of the cancer tissue and normal tissue using microarray technology; (g) comparing the expression profile of the cancer tissue to that of the normal tissue; (h) prioritizing proteins (and the genes encoding such proteins) with coupled over-expression that are either previously identified as cancer-related genes or in one of six functional groups postulated as foundational to the cancer process; (i) designing an appropriate RNA interference (RNAi) expression cassette to, directly or indirectly, modulate the expression of the genes encoding the prioritized proteins; (j) incorporating said cassette into an appropriate delivery vehicle; (k) providing the patient with an effective amount of the delivery vehicle to, directly or indirectly, modify the expression of such genes exhibiting abnormal expression levels; (l) assessing the molecular activity-based reduction in cellular and potentially plasma levels of the targeted gene(s) after exposure to treatment (i.e., the delivery vehicle); and (m) pursuing subsequent treatment, if necessary, based on the emergence of new priority genes and over-expressed cancer-related proteins.

In other embodiments, target gene expression may be repressed in the tumor and, therefore, require derepression or exogenous supplementation in order to achieve a therapeutic benefit to the patient. Upregulation of gene expression may be achieved by supplying additional gene copy to the tumor cell, wherein said gene copies are insulated from the repressive effect being exerted on the endogenous gene expression. In other cases, the repressive element that suppresses the target gene expression may itself become a target for knock-down or suppressive RNAi therapy. In still other cases, the repressive element may be out-competed by exogenously supplied analogs or gene expression elements that produce such analogs. In the foregoing embodiments, the repressed target gene may be normalized or upregulated (derepressed) using, for example, zinc finger proteins (ZFP), RNA activation (RNAa), or miRNA modulation in linkage with or in a common vector.

The invention further provides that cancer/normal tissue whole genomic analysis may be employed to ascertain an index patient's genetic predisposition to a particular cancer as well as a toxicogenomic display, wherein such analysis may include determining the copy number, structure, location, and sequence of a particular gene (or collection of genes). Such DNA genomic analysis may be carried out using various techniques well-known in the art, including without limitation chromosomal karyotyping, fluorescence in situ hybridization (FISH) (for gene copy number determination), high resolution genetic footprinting (for protein-DNA interactions), restriction fragment length polymorphism (RFLP) analysis, single nucleotide polymorphism analysis, and high-throughput DNA sequencing (for gene structural features and mutations).

According to further embodiments of the present invention, gene expression profile information (and/or proteomic information) is provided to a computing platform which assists in assessing co-expression and pathway/module ascription (and, using established and expanding databases, assessing co-regulation by common transcription factors), as well as identification of genes exhibiting abnormal expression levels and/or patterns, which, when correlated, may represent preferred targets for RNAi therapy (as described herein).

According to still further embodiments of the present invention, certain kits and compositions are provided that may be used for carrying out the methods of diagnosing, treating, and monitoring cancer described herein.

The above-mentioned and additional features of the present invention are further illustrated in the Detailed Description contained herein. All references disclosed herein, including U.S. patents and published patent applications, are hereby incorporated by reference in their entirety as if each was incorporated individually.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 3: Analysis of 2-D DIGE images using DeCyder Software and mass spectrometry protein identification. The upper left panel shows the protein expression pattern of a normal lymph node from Patient-1 following 2-D gel electrophoresis. The upper middle panel shows the protein expression pattern of a malignant lymph node from Patient-1. The upper right panel shows a 2-D gel electrophoresis image showing the protein expression pattern of a normal lymph node (labeled with Cy3 (green)) superimposed over a 2-D gel electrophoresis image showing the protein expression pattern of a malignant lymph node (labeled with Cy5 (red)). Circles indicate protein spots with significant expression level changes. The middle panel shows a computer-generated 3D view of one protein spot change between the normal and malignant lymph nodes shown in the upper right panel. The lower panel shows the results of mass spectrometry analyses that were subsequently performed on certain proteins (exhibiting an increase in expression level in the malignant lymph nodes) excised from the 2-D gel as described herein. The mass spectrometry analysis identified the subject protein as RACK1.

FIG. 5: (A) Diagrams prepared using VisualCell software that show "nearest neighbor protein-protein (first order) interactions" of the 5 prioritized proteins described herein. (B) Diagram showing "second order interactions" for Stathmin1 (SDCBP). (C) Diagram showing "second order interactions" for RACK1 (GNB2L1).

FIG. 7: (A) Western blot demonstrating upregulated expression of RACK1 in Patient-1 malignant tissue and malignant cell line CCL247. Limited expression in normal tissue for Patient-1 (lymph node shown, skin and peripheral blood cells also negative) is also shown for comparison. (B) Western blots showing siRNA knockdown of RACK1 in "mock" (i.e., control) samples (lane 1), 24 hour post-siRNA (post-siRACK) knock-down (lane 2), and 48 hour post-siRACK knock-down (lane 3). (C) Chart showing "cell kill" in response to siRNA-RACK 1 over time in colon cancer cell line CCL247.

FIG. 9: Table of the "prioritized" proteins discussed in the Examples below.

FIG. 10: A list of nucleic acid sequences used to construct certain enhanced shRNA molecules described herein, which shows the location of the sense sequence, anti-sense sequence, and mismatches thereof SEQ ID NOS.: 17 and 19; 17 and 20; 17 and 21; 15 and 16; 15 and 22; 15 and 23 and 15 and 24.

BRIEF DESCRIPTION OF THE SEQUENCE LISTING

SEQ ID NO:1-3 represent gene-specific PCR primers used to prepare the cDNAs described herein.

SEQ ID NO:4 represents the sense strand of the siRNAs used to suppress the expression of STMN1 (#16428).

SEQ ID NO:5 represents the antisense strand of the siRNAs used to suppress the expression of STMN1 (#16428).

SEQ ID NO:6 represents the psiTEST Forward PCR primer.

SEQ ID NO:7 represents the psiTEST Reverse PCR-primer.

SEQ ID NO:8 represents the pSilencer Forward PCR primer.

SEQ ID NO:9 represents the pSilencer Reverse PCR primer.

SEQ ID NO:10-22 represent the sequences used to prepare the enhanced shRNA constructs described herein, and summarized in Table 1 below.

SEQ ID NO:23 represents the sense strand of the RACK1 siRNA molecules described herein.

SEQ ID NO:24 represents the antisense strand of the RACK1 siRNA molecules described herein.

SEQ ID NO:25 represents the RACK1 gene.

SEQ ID NO:26 represents the Syntenin gene.

SEQ ID NO:27 represents the Stathmin 1 gene.

SEQ ID NO:28 represents the sense strand of the Stathmin 1 siRNA.

SEQ ID NO:29 represents the antisense strand of the Stathmin 1 siRNA.

SEQ ID NO:30 represents the sense strand of the Syntenin siRNA.

SEQ ID NO:31 represents the antisense strand of the Syntenin siRNA.

DETAILED DESCRIPTION OF THE INVENTION

The following will describe in detail several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used, and made without departing from the scope and spirit of the invention.

Figure 1A:
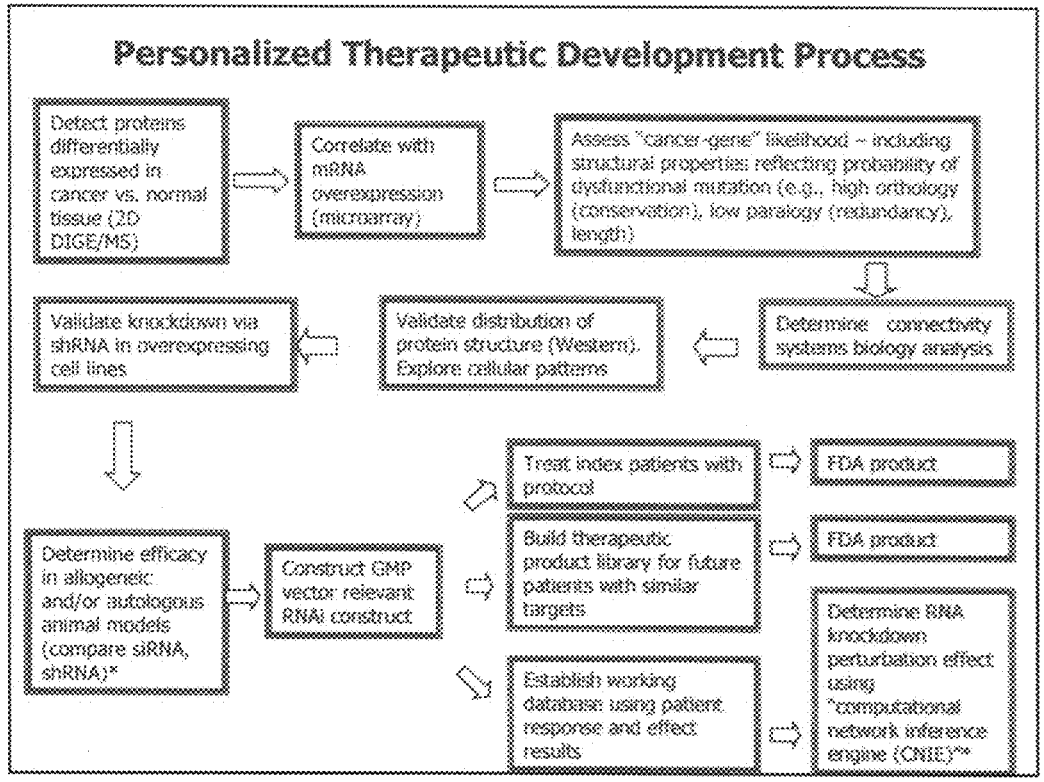
FIG. 1: (A) A flow diagram showing certain methods of the personalized therapeutic programs described herein. (B) A flow diagram showing the various molecular and phenotypic data types that are utilized by certain methods encompassed by the invention described herein.

According to a first embodiment of the present invention, methods for treating cancer are provided (FIG. 1A), which comprise (a) obtaining a specimen of cancer tissue from a patient; (b) obtaining a specimen of normal tissue in the proximity of the cancer tissue from such patient; (c) extracting total protein and RNA from the cancer tissue and normal tissue; (d) obtaining a proteomic profile of the cancer tissue and normal tissue using 2D difference in-gel electrophoresis/mass spectrometry (2D-DIGE/MS); (e) identifying proteins that are over-expressed in such cancer tissue compared to normal tissue; (f) obtaining a normalized genomic profile of the cancer tissue and normal tissue using microarray technology; (g) comparing the expression profile of the cancer tissue to that of the normal tissue; (h) prioritizing proteins (and genes encoding such proteins) with coupled over-expression that are either previously identified as cancer-related genes or in one of six functional groups postulated as foundational to the cancer process; (i) designing an appropriate RNA interference expression cassette to, directly or indirectly, modulate the expression of such genes; (j) incorporating said cassette into an appropriate delivery vehicle; (k) providing the patient with an effective amount of the delivery vehicle to, directly or indirectly, modify the expression of such genes exhibiting abnormal expression levels; (l) assessing the molecular activity-based reduction in cellular and potentially plasma levels of the targeted gene(s) after exposure to treatment (i.e., the delivery vehicle); and (m) pursuing subsequent treatment, if necessary, based on the emergence of new priority genes and over-expressed cancer-related proteins. A non-limiting, preferred embodiment of such methods is illustrated in FIG. 1A. As used herein, the "six functional groups postulated as foundational to the cancer process" consist of cancer cell survival, angiogenesis, self-sufficiency in growth signals, insensitivity to anti-growth signals, limitless replicative potential, and invasiveness (and metastagenicity).

The invention further provides that cancer/normal tissue whole genomic analysis may be employed to ascertain an index patient's genetic predisposition to a particular cancer, as well as a toxicogenomic display, wherein such analysis may include determining the copy number, structure, location, and sequence of a particular gene (or collection of genes). Such DNA genomic analysis may be carried out using various techniques well-known in the art, including without limitation chromosomal karyotyping, fluorescence in situ hybridization (FISH) (for gene copy number determination), high resolution genetic footprinting (for protein-DNA interactions), restriction fragment length polymorphism (RFLP)

analysis, single nucleotide polymorphism analysis, and high-throughput DNA sequencing (for gene structural features and mutations).

According to further embodiments of the present invention, gene expression profile information (and/or proteomic information) is provided to a computing platform which assists in assessing co-expression and pathway/module ascription (and, using established and expanding databases, assessing co-regulation by common transcription factors), as well as identification of proteins (and genes encoding such proteins) exhibiting abnormal expression levels and/or patterns, which may represent preferred targets for RNAi (using, for example, the siRNAs, conventional shRNAs, or enhanced shRNAs described herein).

According to still further embodiments of the present invention, certain kits and compositions are provided that may be used for carrying out the methods of diagnosing, treating, and monitoring cancer described herein.

Tissue Isolation

Normal and malignant tissue may be isolated from a patient using standard and well-known biopsy procedures. In certain preferred embodiments, however, such tissue may be processed using laser capture microdissection (LCM). The majority of tumor samples represent an admixture of different cell types, including hematologic and vascular intercalated stromal tissue. Therefore, reported gene expression patterns may not be specific to malignant cells. This potentially confounding factor may be addressed with the use of LCM technology.

LCM allows malignant cells to be selectively dissected and captured from the mixed population of cells found in a tumor biopsy, so that only a morphologically homogeneous population of cells is investigated from a complex tissue. Improvements in nucleic acid amplification and protein detection technologies have made it possible to accurately and reproducibly analyze small amounts of DNA, RNA, or proteins from LCM-derived cells. Accordingly, the invention provides that LCM may be used to separate malignant from normal cells—followed by amplification in order to carry out the methods described herein and identify those genes differentially expressed in a particular patient's tumor.

Nucleic Acid Extraction

Nucleic acids, such as RNA and/or DNA, may be isolated and purified from cells, tissues or fluids of a patient using readily-available and well-known procedures. For example, RNA may be preferentially obtained from a nucleic acid mix using a variety of standard procedures (see, e.g., RNA Isolation Strategies, pp. 55-104, in *RNA Methodologies, A laboratory guide for isolation and characterization,* 2nd edition, 1998, Robert E. Farrell, Jr., Ed., Academic Press). Additionally, RNA isolation systems/kits are available from numerous commercial vendors, such as the RNAqueous™, Phenol-free Total RNA Isolation Kit offered by Ambion (Austin, Tex.) or the PicoPure RNA Isolation kit offered by Arcturus Bioscience (Mountainview, Calif.). Similarly, DNA isolation systems/kits are readily available, such as the GeneElute™ Mammalian Genomic DNA Miniprep Kit or GeneElute™ Blood Genomic DNA Kit offered by Sigma-Aldrich Company (St. Louis, Mo.).

In certain preferred embodiments of the present invention, total RNA and/or DNA is extracted from LCM-isolated tissues. RNA and/or DNA extraction from LCM samples is a standard operation. It is generally preferred to obtain about 20,000 cells and for gene expression profiles to be conducted for each cancer and normal tissue type.

In certain embodiments, for example, RNA may be extracted from LCM-isolated tissues (or tissues obtained through conventional biopsy procedures) using the PicoPure RNA Isolation kit referenced above—according to the manufacturer's protocol. Quality of captured RNA is, preferably, examined following extraction. The quality of isolated RNA may be measured using well-known procedures, such as with an Agilent 2100 Bioanalyzer and RNA 6000 Pico LabChips (Agilent Technologies, Palo Alto, Calif.). The isolated RNA is preferably divided into separate groups of equal proportion, such as two or more groups, which are then subjected to parallel RNA amplification and gene profile analysis. It is generally preferred that R-square tests be performed to provide an indicator for the reproducibility of the data generated from such different groups of isolated RNA.

In certain preferred embodiments of the present invention, the isolated RNA (and/or DNA) is amplified before labeling (and subsequent gene expression profiling or other nucleic acid analysis described herein). Those of ordinary skill in the art will appreciate that RNA and DNA amplification (and labeling) may be carried out using commercially-available kits and/or well-known procedures. For example, RNA amplification may be carried out using a RiboAmp RNA Amplification Kit (Arcturus Bioscience, Mountainview, Calif.). Following such amplification step, the quality of the amplified RNA (and/or DNA) is, preferably, examined with BioAnalyzer—wherein, for example, the size distribution of amplified RNA should be a healthy streak larger than 250 nucleotides (nt) in size. Next, the amplified RNA (and/or DNA) may be labeled with appropriate isotopes, chemoluminescent molecules, and other agents using well-known techniques and/or commercially-available kits.

Gene Expression Profiling & Other Nucleic Acid Analysis

RNA (cDNA) expression profiles of the isolated cancer and normal cells may be obtained using readily-available technology, such as microarray technology. In recent years, "DNA chips" have provided a reliable means for measuring the expression levels of particular genes or, more particularly, the level of specific mRNA transcripts (or cDNAs) in a sample. Of course, those skilled in the art will appreciate that other methods may be employed to obtain such expression profiles, such as quantitative PCR (qPCR), northern blots, and others (currently-available or discovered hereafter).

In certain preferred embodiments of the present invention, for example, microarray analysis may carried out using the GeneChip® system of Affymetrix following recommended procedures. Still more specifically, for example, such microarray analysis may be carried out using the Affymetrix Human U133 Plus 2.0 GeneChip®, which may be used for hybridization and analysis of the isolated, amplified, and labeled RNA described herein. Hybridization and processing of such GeneChip may be performed using the automated GeneChip Instrument System. Data acquisition, sample normalization, and initial data analysis may be performed with Affymetrix Microarray Suite (MAS) software.

Preferably, the data collected from such microarray analysis are imported into a computing environment, wherein software and other tools may be used to analyze and interpret such data. In certain embodiments, for example, such data may be directly imported into GeneSpring 7.0 gene expression analysis software (Silicon Genetics, Redwood City, Calif.) for expression profile analysis. The RNA expression profile of normal and malignant cells may then be analyzed, preferably, in pair-wise fashion to identify genes that are significantly overexpressed, for example, in the malignant cells (when compared to the corresponding expression level of particular gene(s) in the normal cells). In certain preferred embodiments, the quality of data will also be determined. For example, robust data that reveal significant differential gene-expression patterns (between normal and cancer cells) may be further analyzed at a higher level for target identification. In such embodiments, the raw data will be transported to a computational system, such as the system designed and owned by Gene Network Sciences, Inc. The system employed by GNS to identify abnormally expressed genes and Target Genes (as defined herein) is described in U.S. Patent Application Publications 2003/0144823 (Scale-free Network Inference Methods); 2004/0243354 (Systems and Methods for Inferring Biological Networks); and 2004/0088116 (Methods and systems for creating and using comprehensive and data-driven simulations of biological systems for pharmacological and industrial applications), all of which are expressly incorporated herein by reference.

As previously described, the invention further provides that DNA genomic analysis may be employed in addition to (or in replacement of) gene expression profiling. Such analysis may be employed to, for example, assess co-expression (i.e., genes with similar mRNA expression profiles) and pathway/module ascription (and, using established and expanding databases, assessing co-regulation by common transcription factors), as well as identification of genes exhibiting abnormal expression levels and/or patterns which, when correlated, may represent preferred targets for RNAi. Additionally, DNA genomic analysis may be conducted to ascertain a patient's genetic predisposition to a particular cancer and/or the current disease state of such patient, wherein such analysis may include determining the copy number, structure, location, and sequence of a particular gene (or collection of genes). This may also include a toxicogenomic display to enhance the understanding of mechanisms of toxicity and provide a potential pre-exposure screening for risk of therapy-related adverse events and characterization thereof, especially for trans-modality combination therapy, e.g., a targeted shRNA and a selected chemotherapy agent.

Such DNA genomic analysis may be carried out using various techniques well-known in the art, including without limitation chromosomal karyotyping, fluorescence in situ hybridization (FISH) (for gene copy number determination), high resolution genetic footprinting (for protein-DNA interactions), restriction fragment length polymorphism (RFLP) analysis, single nucleotide polymorphism analysis, and high throughput DNA sequencing (for gene structural features and mutations). The results and information obtained from such DNA genomic analysis are, preferably, imported into a computing environment, wherein software and other tools may be used to analyze and interpret such data. The invention provides that such information may be considered (preferably, in connection with gene expression profile and/or proteomic information) when identifying Target Genes (as described herein).

Proteomics: 2D-DIGE/MS

Microarray technology is well established as a powerful tool for global gene expression analysis. mRNA profiles (or cDNA profiles) have been used both for cancer classification as well as to predict prognosis. Whereas the mRNA (cDNA) microarray studies have greatly enhanced our understanding of the underlying mechanisms of cancer, studies at the protein level also present unique advantages, as proteins are the direct effectors of cellular behavior. Furthermore, the invention provides that because of post-translational modifications ncRNA modulated effects, including alternate RNA splicing, RNA editing and mRNA stability, and quantitative sampling limitations (such as serum), the isolated cancer and normal tissue in each patient are, preferably, analyzed using proteomic approaches.

While such proteomic approaches may be carried out using methods well-known to those of ordinary skill in the art, the invention provides that, in certain embodiments, such approach may be carried out using 2D-DIGE/MS analysis of protein extracted from patient tissue, i.e., normal and cancer tissue (LCM-captured if <70% cancer cells). Preferably, duplicate samples will be selected for reproducibility comparison.

In certain embodiments, the 2D-DIGE system may be optimized to identify approximately 10,000 protein spots—using combinations of smaller pH ranges for isoelectric focusing (IEF) separation, and variable percentage sodium dodecyl sulfate (SDS) gel electrophoresis separation. With the resolution of 10,000 protein spots, the 2D-DIGE/MS analysis system provides yet further information that may be used in identifying Target Genes (defined herein) and corresponding RNAi molecules as described herein. Preferably, the information provided by the 2D-DIGE/MS analysis will be used in connection with (and compared to) the information provided by microarray analysis when identifying Target Genes and corresponding RNAi molecules as described herein.

In certain non-limiting embodiments of the present invention, 2D-DIGE/MS analysis may be carried out by isolating approximately 10 mg-equivalent of human normal and cancer tissues or, alternatively, capturing a sufficient amount of such tissues using laser capture microdissection (LCM). Next, such tissue may be lysed in 2-D lysis buffer containing 30 mM Tris-HCl (pH 8.8), 7 M urea, 2 M thiourea and 4% CHAPS. Sonication may be used to facilitate the lysis step. The protein lysates may, if necessary, be further purified using filters, chromatography, or other means. The sufficiently purified protein isolates may then be labeled with, for example, CyDye fluors (Cy2, Cy3 or Cy5) for 30 minutes at 0° C.—using procedures well-known in the art or commercially-available kits. In such example, the reaction may be terminated with the addition of lysine, and samples to be compared are mixed in an equal molar ratio. Next, in such example, destreak solution and rehydration buffer may be added (100 µl each) before samples are loaded onto a 13-cm IPG strip, with a linear pH range of 3-10, for IEF analysis ($1^{st}$ Dimension) (GE Healthcare, formerly Amersham Biosciences, Piscataway, N.J.).

After the IEF analysis is completed, the IPG strip is incubated with SDS-containing equilibration solutions and placed on top of a 9-12% gradient SDS gel (18×16 cm, 1-mm thickness). Electrophoresis separation with the SDS gel is performed at 16° C. ($2^{nd}$ Dimension). After electrophoresis, the gel is analyzed using an appropriate scanner, such as a Typhoon Trio scanner (GE Healthcare), and the images may be analyzed using ImageQuant and DeCyder software. Protein spots of interest are excised from the gel and protein IDs are determined using matrix-assisted laser desorption/ionization time-of-flight mass spectrometry (MALDI-ToF). Data obtained from 2D-DIGE/MS will be compared to data obtained from microarray. Non-limiting examples of the data, and analysis thereof, produced by the foregoing process are shown in FIG. 3. The differentially-expressed proteins identified by the above proteomic analysis will be provided to and used in the pathway identification and Target Gene selection process described herein.

Target Gene Selection

High-quality raw data from the foregoing gene expression profiling (e.g., microarray analysis), genomic DNA analysis, and/or proteomic (e.g., 2D-DIGE/MS) analysis will be stored and analyzed with a computational system, such as the system designed and owned by GNS, to identify Target Genes. As used herein, "Target Gene" refers to a nucleic acid sequence in a cancer cell, wherein the expression of the sequence is specifically and effectively modulated using the methods of the present invention. Preferably, the Target Gene is shown to be implicated in the growth (proliferation), maintenance (survival), and/or migratory (metastatic) behavior of an individual's cancer. Furthermore, the terms "prioritized proteins," "priority proteins," and like terms refer to the proteins encoded by such Target Genes. Non-limiting examples of results showing the identification and analysis of various Target Genes found in several patients, using the methods described herein, are shown in FIG. 22.

In certain preferred embodiments of the present invention, Target Gene selection may be based on one or more of the following criteria: (1) high cancer expression compared to low normal expression (i.e., the relative magnitude of the difference in expression levels between a particular gene in normal versus malignant cells); (2) key gene regulatory (static) nodes in dominant activated cancer associated pathways (e.g., the role of akt and mTOR in the ras activated pathway); (3) whether a particular gene represents a strategic connecting (dynamic) node shared by multiple cancer signal transduction pathways; (4) known cancer-related genes (to name a few, genes such as HER2 (a growth factor receptor), ras (a signal transduction molecule), myc (a transcription factor), src (a protein tyrosine kinase), and Bcl-2 (an anti-apoptotic molecule); and (5) co-essential genes characterized by low k-robustness the concomitant repression of which overcomes the effect of functional gene duplication (i.e., genetic redundancy)).

As described herein, the invention provides that, in addition to an individual's gene expression profile, other information may be considered when identifying Target Genes. For example, the invention provides that the results and information obtained from DNA genomic analysis may be considered during Target Gene selection. That is, such DNA genomic analysis may reveal whether a patient carries a particular mutation in one or more genes (and/or whether such one or more genes exhibit abnormal gene structure, location, and/or copy number), which are known or suspected to be implicated in cancer growth, maintenance, migratory behavior, etc. For example, based on the results of such DNA genomic analysis (and information that it provides relating to the genetic aberrations, if any, detected in a particular individual), it may be desirable to select a Target Gene(s) that may correct or mitigate the effects of such genetic aberrations.

Still further, Target Gene selection may consider whether the nucleic acid sequence of a candidate gene exhibits RNAi sensitivity characteristics, e.g., genes that have been reported to be effectively knocked-down by RNAi mechanisms (or whether the expression of such nucleic acid may be effectively modulated using, e.g., other transcriptional and/or translational inhibitors). This approach is conceptually consistent with the rationale proposed for the use of RNAi, for example, to evaluate the genetics of synthetic lethality. The foregoing criteria may be used by computational systems, such as the system designed and owned by GNS, to assist in the identification of Target Genes.

The invention provides that, despite the evolved robust survival advantage of cancer cells (due, in large part, to their co-option of normal pathways), sites of fragility resulting from functional tradeoffs accompanying the evolution of the co-opted biomic network result in "addiction" to a limited set of functional pathways with key regulatory cores of single or multiple genes required for said survival. The present invention, preferably, exploits such dependency as the "Achilles heel" of cancer.

In certain embodiments of the present invention, the gene expression profiles of normal and cancer tissues are compared over a non-selective, broad range of coding sequences. In other, preferred embodiments, such comparison is focused on a number of genes that have been shown to be implicated, directly or indirectly, in cancer. Preferably, the identity and sequences of such genes are constantly updated to reflect and incorporate new information that is generated in cancer research. For example, in certain embodiments of the present invention, the analysis of gene expression profiles of normal and cancer cells are made by conferring with a database, which contains a listing of all such genes that are known to be implicated in cancer at the time of such analysis. Preferably, such database is capable of being regularly updated to reflect the most current understandings of cancer and causes thereof, so that the expression levels of all (or a significant number of) relevant genes may be analyzed.

In certain embodiments, the expression levels of the genes analyzed in an individual's cancer tissue are compared to the expected levels in population-derived cancer and normal tissue, wherein such expected values are stored in a database and based on previous research. In other, preferred embodiments of the invention, the expression levels of the genes analyzed in an individual's cancer tissue are compared to the corresponding levels actually measured in normal tissue. The invention provides that by comparing the expression profiles of cancer and normal tissue extracted from the same patient, the individual nuances and expression aberrations that each individual patient may carry are normalized. By co-analyzing the personal data in the context of available population-derived data, the invention allows for the validation of the latter, while benefiting from enhanced discovery in the targeted data set through the recognition of conservation across multiple gene sets otherwise limited in any one gene set.

In some cases, the Target Genes may be expressed at significantly higher levels when compared to normal tissue from the same patient (or predicted levels based on public literature). In such cases, it may be appropriate to build an expression cassette that expresses an shRNA or multiple shRNAs, for example, which hybridize(s) to the targeted mRNA transcript or multiple targeted mRNA transcripts encoded by such Target Genes, and reduces the expression levels of such Target Gene or Genes simultaneously—either at transcriptional and/or at translational levels. Similarly, the invention provides the utilization of small interfering RNA (siRNA) to achieve the above-mentioned repression of Target Gene expression. Furthermore, siRNA and shRNA may be applied in combination to achieve the maximum and desirable modulatory effect that is the most advantageous for the intended therapeutic applications. Still further, the invention provides certain novel enhanced shRNA molecules that may be employed to modulate the expression of such Target Genes, as described herein.

In still other embodiments, the expression levels of the Target Genes may be undesirably repressed. In such cases, multiple mechanisms, including but not limited to microRNA (miRNA), ncRNA, aberrantly-expressed transcription factors and/or transcriptional regulatory elements, may cause a corresponding reduced expression level for the Target Gene (referred to herein as the "Contributing Gene"). For example, the invention provides that the over-expression (or increased copy number) of a Contributing Gene (e.g., a sequence encoding a transcriptional repressor) may, directly or indirectly, cause a Target Gene to exhibit an undesirable reduced expression level. In such embodiments, appropriate siRNA and/or shRNA cassettes, for example, may be constructed to reduce the expression level of the Contributing Gene, thereby decreasing the negative selective pressure on the Target Gene (and, preferably, allowing the expression level of the Target Gene to resume to normal or preferred levels). Similarly, it may be desired to introduce additional or other cassettes that encode preferred transcriptional and/or translational modifiers or inhibitors—to modulate the expression of such Contributing Gene (thereby regulating the expression of the Target Gene).

In yet other cases, the expression levels of a Target Gene may be repressed (e.g., suppressor gene) and, via connectivity, be in causal relationship with overexpressed Target Genes. In such cases, said repressed Target Gene may be normalized or upregulated (derepressed) using zinc finger proteins (ZFP), RNA activation (RNAa), or miRNA modulation in linkage with or in a common vector with the invention. In still other cases, the repression may be overcome by supplying exogenous copies of the Target Gene, wherein said gene copies are insulated from the repressive effect being exerted on the native (i.e., endogenous) gene expression. In still other cases, the repressive element may be out-competed by exogenously-supplied analogs or gene expression elements that produce such analogs.

The invention further provides that multiple siRNA and shRNA combinations may be employed to suppress the expression of abnormally highly expressed Target Genes and Contributing Genes.

Figure 21:
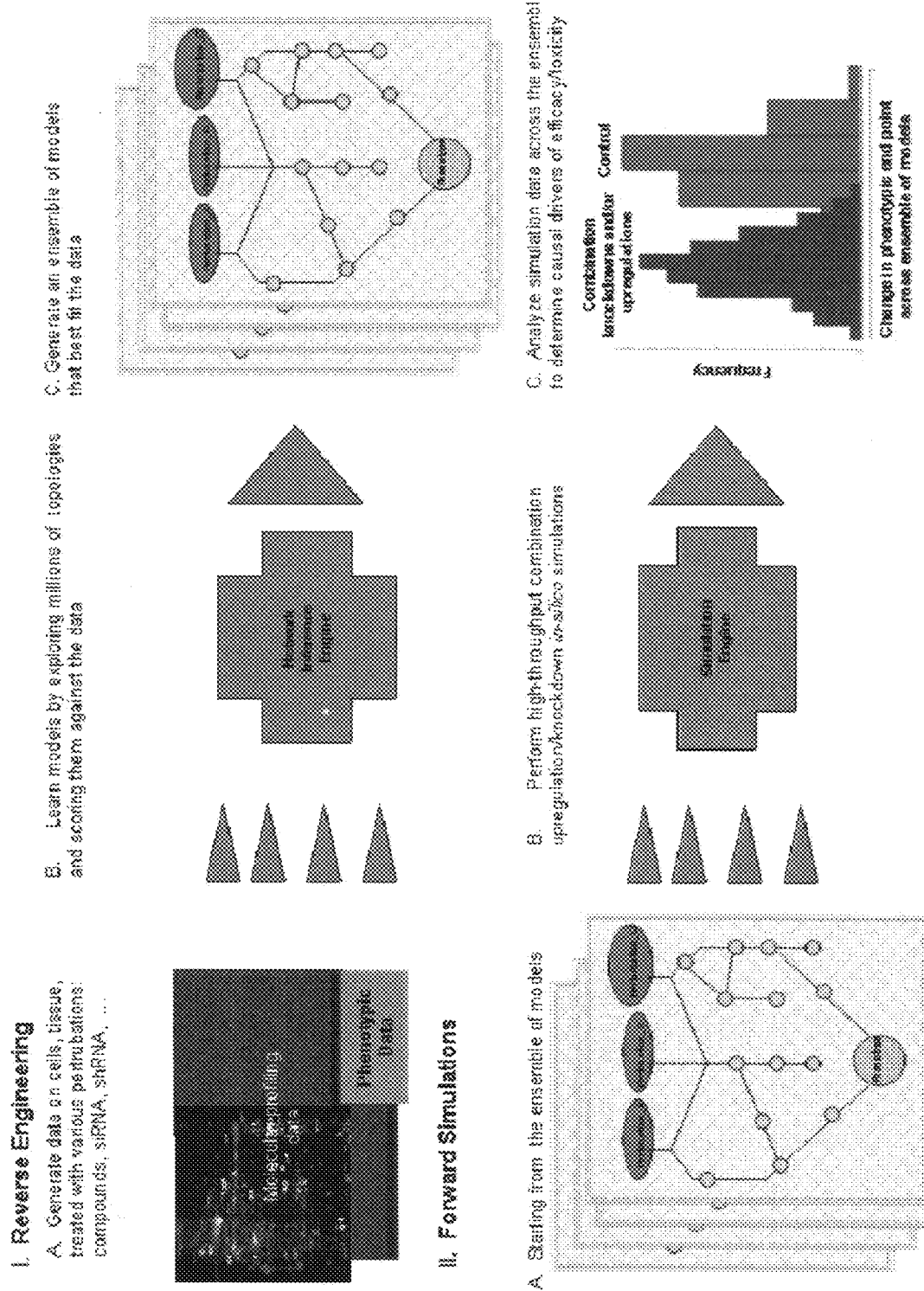
FIG. 21: A flow chart summarizing the process by which the GNS system, described herein, assists in identifying target genes (and prioritized proteins) for RNAi knock-down.
Figure 22A:
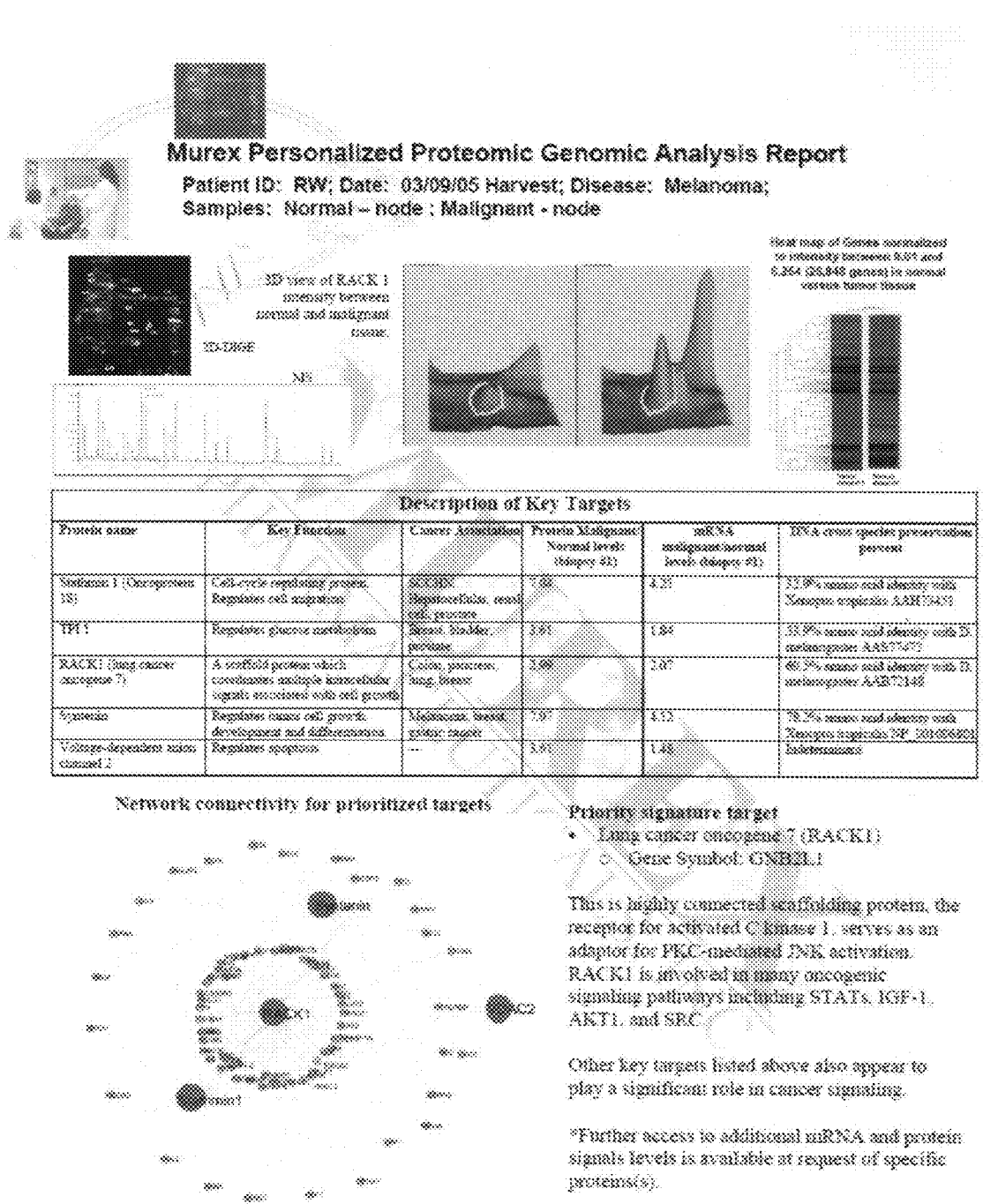
FIG. 22: (A)-(G) Results of nearest neighbor protein-protein (first order) interactions of priority proteins in VisualCell of seven (7) patients that were examined using the methods described herein.
Figure 22B:
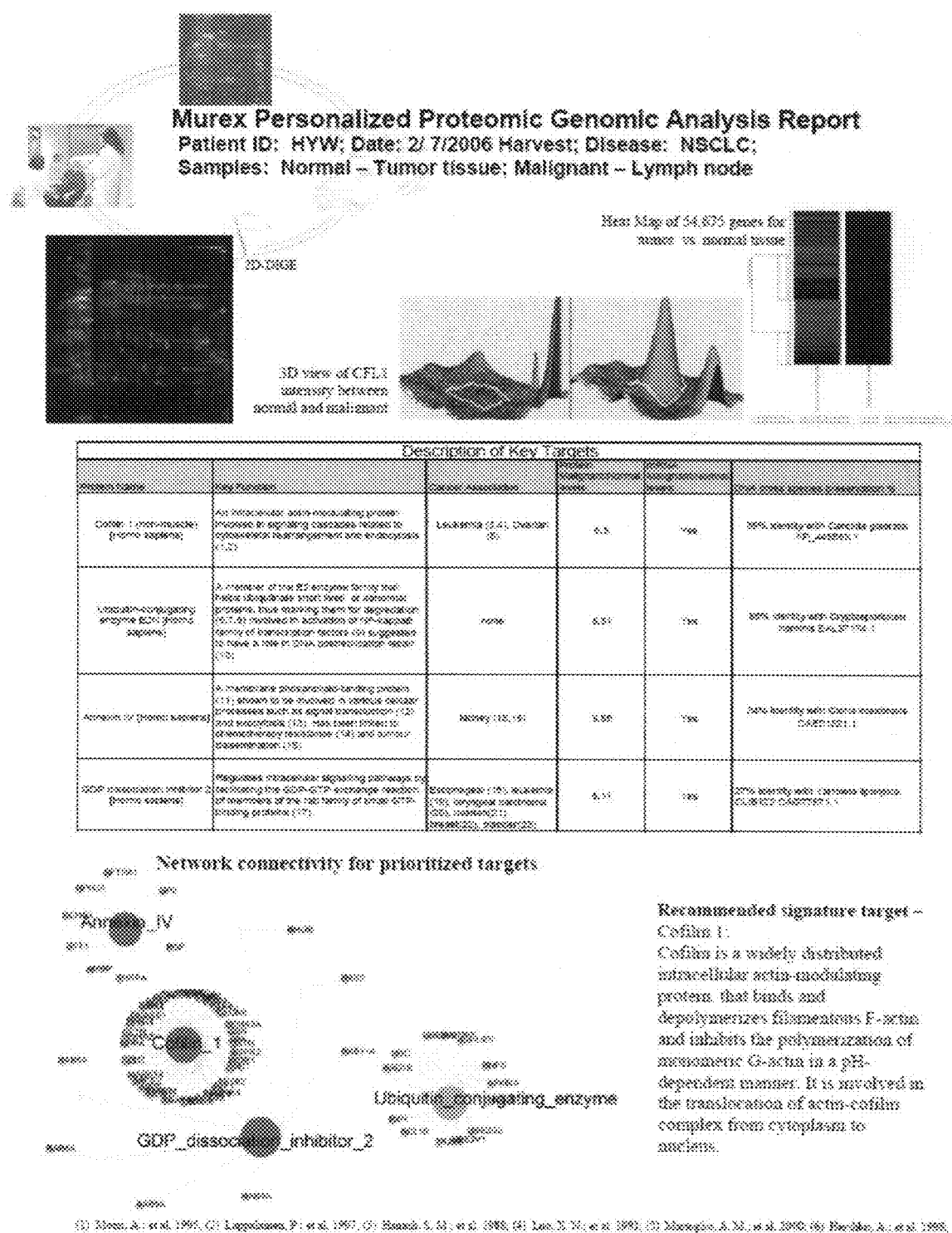
Figure 22D:
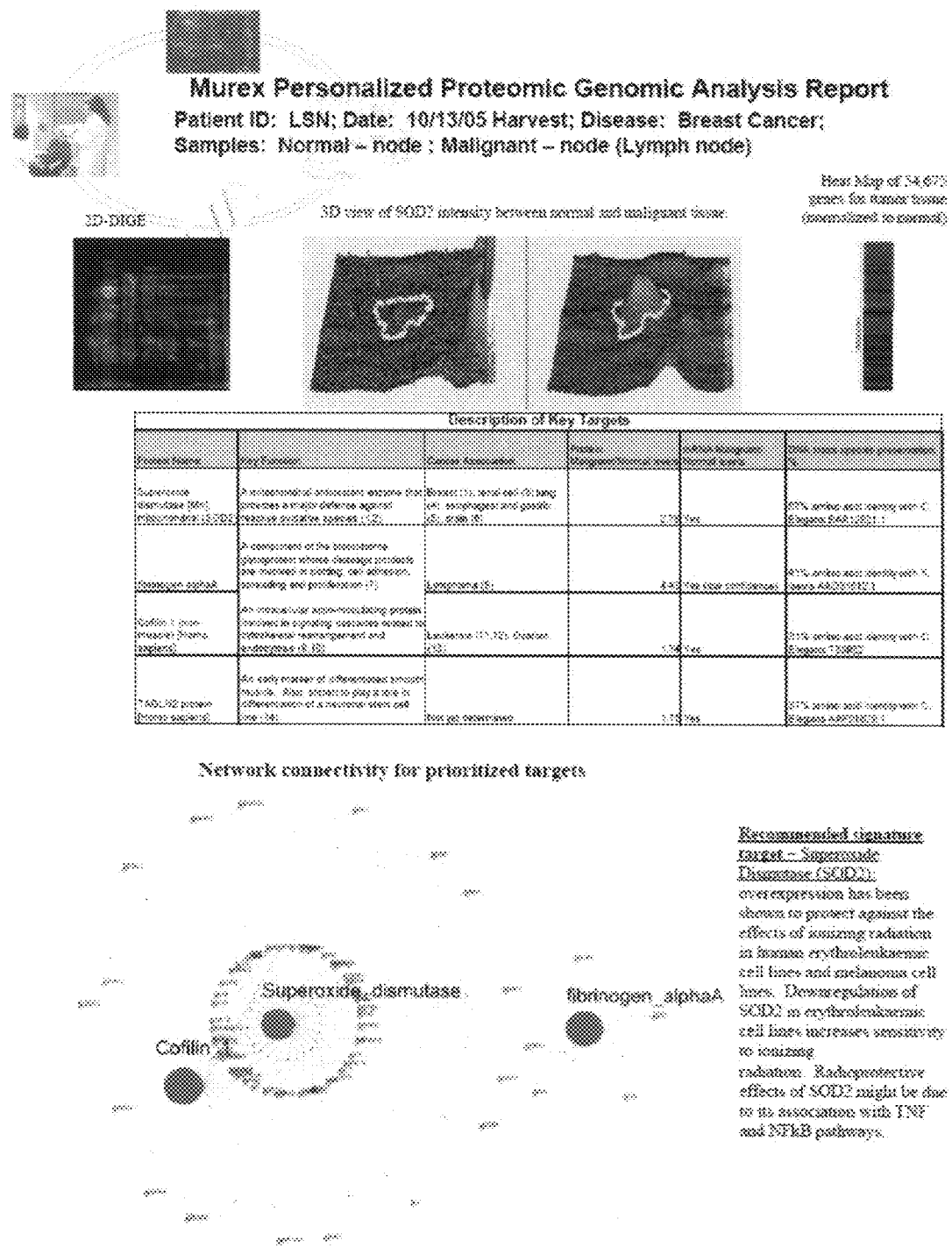
Figure 22E:
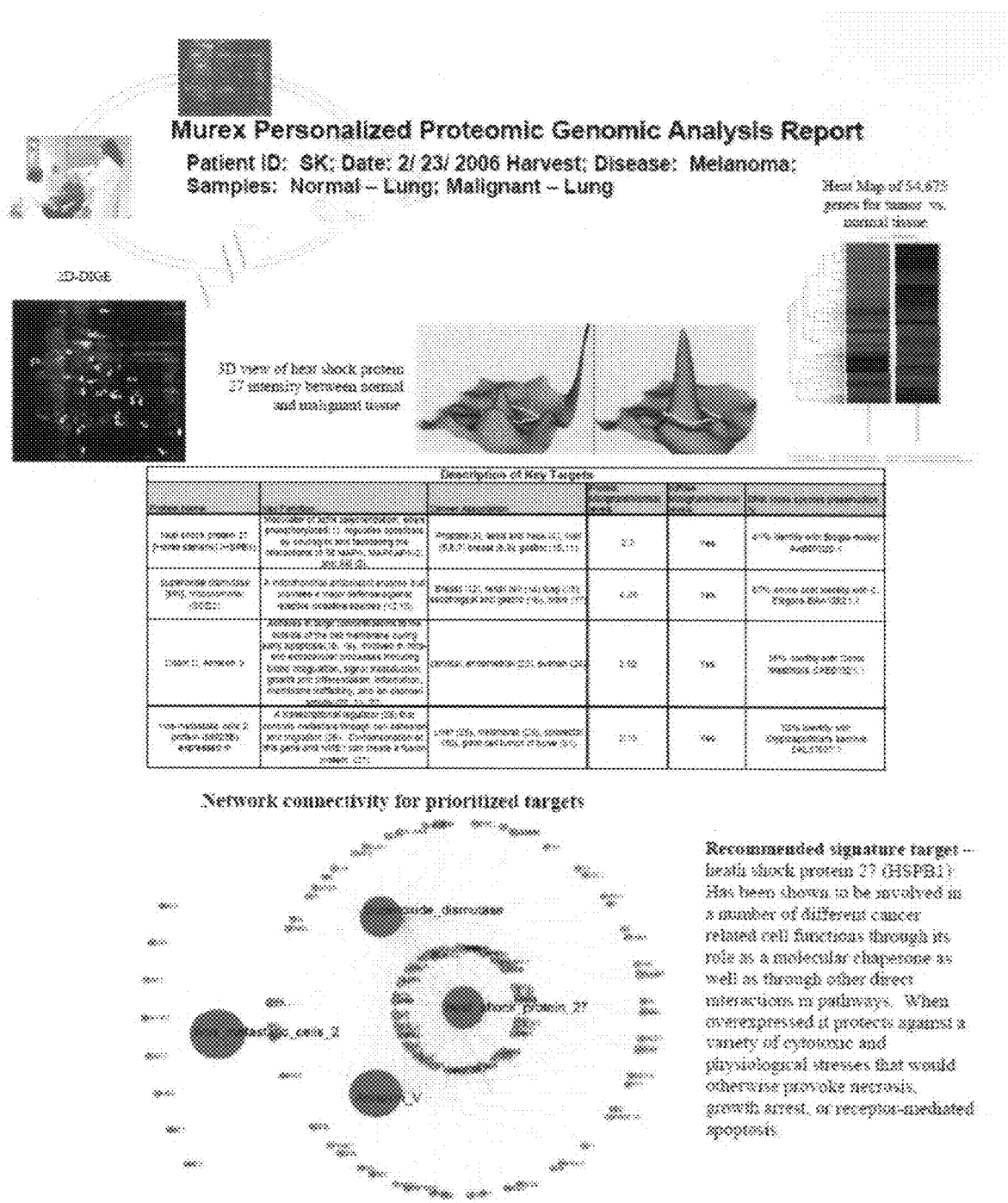

In certain embodiments, raw data obtained from gene expression profiling (e.g., microarray analysis), genomic DNA analysis, and/or proteomic analysis (e.g., 2D-DIGE/MS) may be transported to a computer system for temporary analysis, such as the proprietary computer system designed, developed and owned by Gene Network Sciences, Inc.—which uses a certain Network Inference software platform (FIG. 21). The system employed by GNS to identify abnormally expressed genes and Target Genes (as defined herein) is described in U.S. Patent Application Publications 2003/0144823; 2004/0243354; and 2004/0088116—all of which are expressly incorporated herein by reference.

The Network Inference software platform constructs a probabilistic model of causal relationships between network components that is consistent with a given constraining data set, such as high-throughput data from microarray analysis (FIG. 21A). Rather than identifying a single "best-fit" model, the probabilistic model incorporates uncertainty in the data and allows the corresponding uncertainty in the predictions to be quantified. Inferring regulatory relationships between genes is a global optimization problem in which the objective function to be minimized measures the difference between predictions of the network model and the constraining experimental data. The search domain for this global optimization is the discrete space of all possible bipartite graphs that may be constructed out of an entity (mRNA, protein, or chemical levels) and interaction nodes. Each interaction node is associated with a mathematical function that describes a quantitative relationship between entity nodes. The ensemble of models generated is then subject to analysis to extract out causal relationships. These include forward simulations on the ensemble of models generated that enable the user to determine the response to new perturbations not explicitly represented in the data set (FIG. 21B). For example, an ensemble of models can be inferred from a data set that includes single siRNA or shRNA perturbations from many biological samples along with the corresponding molecular profiling and phenotypic data. The simulation engine then enables the user to test out all two-way and three-way combinations that synergistically lead to inhibition of the phenotypic end point. In this way, scientists may determine key molecular targets and target combinations that significantly impact efficacy and/or toxicity.

Edges in the network generated by the GNS optimization algorithm, for example, correspond to direct causal relationships between measured nodes. Indirect causal relationships between measured nodes are mostly eliminated by the algorithm because it employs a Bayesian scoring function that penalizes extra complexity. However, every edge may represent an indirect relationship via unmeasured nodes (hidden interactions), such as protein signaling pathways that affect gene expression. The Bayesian framework edges in the network may be either directed or undirected (symmetrical). Connections between compounds (e.g., siRNAs), genes and phenotypic endpoints are directed, since siRNAs represent causal perturbations and molecular changes that causally influence the phenotypic response. The direction of gene-gene connections can be elucidated using perturbation experiments, such as through shRNA- and/or siRNA-mediated gene silencing experiments. The present invention may further utilize an experimental paradigm to validate predicted outcomes and to further contribute to a database (for use in future predictions).

Networks learned from data using the GNS Network Inference platform correspond to causal relationships in the experimental system where perturbations to particular genes from siRNAs, for example, are predicted to result in downstream (or upstream in the case of feedback loops as well as autoregulatory transcription factors) changes throughout the network. The accuracy of the inferred networks can therefore be validated by readily-available experimental techniques. The genes that appear in the neighborhood of siRNA (or shRNA) nodes in the network carry the interpretation of being the genes the change in expression of which (in response to siRNA and/or shRNA treatment) is explained (in the Bayesian sense) by the uncovered network. These genes therefore correspond to potential biomarkers of siRNA/shRNA activity. If efficacy or toxicity endpoints are also measured, then these 'first-line' genes in a network that connect siRNA/shRNA effects to the endpoint correspond to biomarkers of treatment efficacy or toxicity. If quantitative proteomics data (e.g., protein phosphorylation levels) are available in addition to data from cDNA microarrays, then the networks learned by including these data types in the constraining data set may uncover direct siRNA- or shRNA-protein relationships capable of elucidating siRNA or shRNA mechanism of action at the protein level. Model predictions may be analyzed in the context of known pathway information to aid in interpretation of results.

The majority of the databases currently available from human derived biopsies are mainly based on conventional compound-based gene perturbation models. Compound-based gene perturbation data are often confounded by the potential side-effects (or additional effects) brought about by the interaction of said compound with other unintended targets. The present invention provides the further advantage of improvement of the database by utilizing said siRNAs or/and shRNAs to specifically reduce expression of the intended Target Gene. Further advantages will be envisioned by those of ordinary skill in art, based on the above-mentioned combinatorial approach to developing and supplementing a novel database.

While the GNS computation analysis system provides a non-limiting example of a platform that may be used to interpret the microarray, genomic DNA, and/or proteomic data described herein, each patient's comparative malignant and normal gene-expression profiles, for example, may also be reviewed and interpreted manually—using a combination of gene-expression analysis programs. Using the pathway viewer in GeneSpring, for example, the over-expressed genes and their expression patterns in an individual patient may be visually characterized based on the location of such genes within a cellular pathway. In conjunction with the self-organizing clustering function of such software (or others), the invention provides that the over-expressed genes and pathways may be mapped and interpreted. Additionally, protein level comparisons between cancer and normal tissues may be carried out using the procedures described above (and illustrated in FIG. 3).

Still further, Target Genes identified using any of the foregoing software, platforms, or other means are, optionally, cross-referenced with other appropriate databases, such as those databases maintained by the Cancer Molecular Analysis Project (CMAP) and the BioCarta and KEGG pathways at NCI.

Figure 1B:
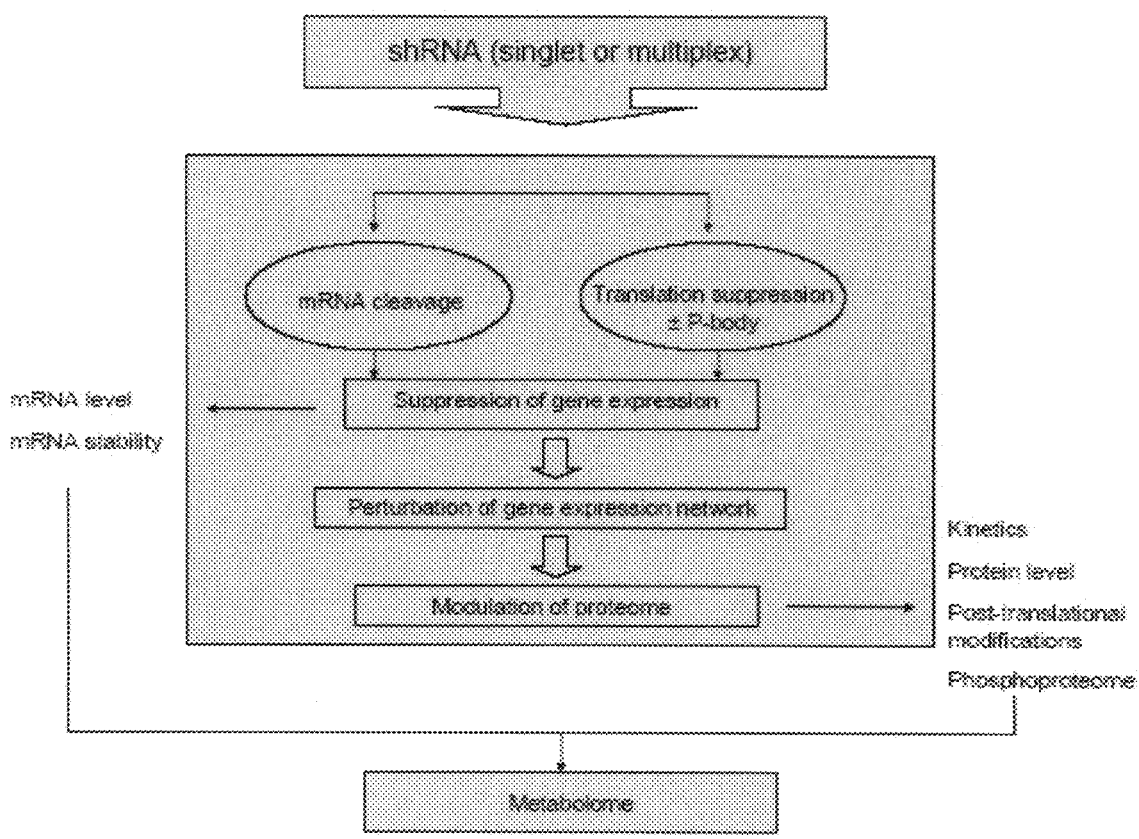

The invention provides that elevated mRNA levels, for example, identified in microarray analysis preferably correspond with discordant protein expression observed in the proteomic analysis. If such analyses do not correspond, a candidate Target Gene may still be a good candidate for RNAi knock-down, but perhaps with lower priority. With computer-assisted analysis, in certain embodiments, the invention provides that multiple Target Genes are preferably identified, such as at least five Target Genes, for each patient based on the various criteria described above. In such embodiment, the Target Gene selection process may be augmented (or completely managed) by, for example, the decision making process summarized in FIG. 1B (wherein an experimental system is treated with compound(s), e.g., siRNA(s), to generate quantitative high-throughput data, whereby the platform uses the data to build a causal network connecting biological entities such as exogenous siRNAs, mRNA, and/or protein and phenotype nodes).

Confirm Over-Expression of Selected Target Genes

Comparative gene expression levels of selected Target Genes are preferably confirmed by quantitative RT-PCR methods. For example, total RNA from normal and malignant patient tissue may be used for such analysis and comparison. Gene-specific PCR primers may be designed and chemically synthesized using well-known procedures or purchased from a commercial vendor. The primer sets will first be tested with total RNA isolated from tissue culture cells to establish appropriate PCR conditions. Once the appropriate PCR conditions are established and the specificity of the primer set is validated, real-time RT-PCR may be performed. Expression level for each Target Gene is, preferably, compared to a common housekeeping gene, such as GAPDH or Actin. The increased (or otherwise abnormal) expression of Target Genes in cancer tissue—relative to normal tissue from the same patient—is preferably confirmed. Although GAPDH and Actin are considered housekeeping genes, there are reports that such genes are expressed at higher levels in tumor cells and that other genes, such as ribosomal protein genes (RPS27A, RPL19, RPL11, RPS29, or RPS3) or, perhaps, a more robust expression signature control would be more useful as a comparator.

shRNA & siRNA Design and Synthesis

Current methods in designing shRNA and siRNA (two different methods of RNAi) often employ a set of computer-implemented rules, which are not always reliable and essentially represent a trial-and-error approach. As used herein, "RNAi molecules" refers generally to conventional shRNA molecules (the well-known shRNA molecules routinely used by those of ordinary skill in the art), enhanced shRNA (the novel shRNA molecules and uses thereof encompassed by the present invention and described below) and/or siRNA molecules. As used herein, "shRNA/siRNA," "siRNA/shRNA," and like terms refer to conventional shRNA, enhanced shRNA, siRNA, or any combination of the foregoing.

Recent studies have indicated rather wide-spread off-target effects of siRNAs (and other RNAi molecules). Although a target gene may be effectively silenced, non-specific effects both at the mRNA and protein levels have been reported. Accordingly, for the clinical applications of the present invention described herein, it is important to incorporate RNAi molecules with desirable potency, efficacy, and binding precision and accuracy. In certain embodiments of the invention, the RNAi molecules are preferably conventional or enhanced shRNAs, as such designs have been shown to be more stable, durable, potent and amenable to regulation than siRNAs. In addition, the incorporation of tumor-specific targeting of the delivery vector and tumor-specific promoters may be utilized, thereby adding a multiple-log safety buffer to the invention.

For each selected Target Gene, the invention provides that a literature search may be conducted to identify any commercially-available shRNA- and siRNA-encoding plasmids that have been shown to modulate the expression of the Target Gene and/or exhibit other preferred characteristics (such as potency, efficacy, and binding precision and accuracy). Additional information regarding such Target Gene, siRNAs, and/or shRNA may, preferably, be obtained from The Cancer Genome Anatomy Project's RNAi site of NCI. If appropriate commercially-available shRNA- and/or siRNA-encoding sequences exist, such compositions or components thereof may be used in the present invention (assuming such compositions satisfy other preferred criteria, such as those relating potency, efficacy, and binding precision and accuracy).

If there are no commercially-available siRNAs or shRNA clones for the selected Target Gene, an appropriate number of shRNAs and/or siRNAs may be designed, such as two, three, four, five, or more shRNAs and/or siRNAs, using readily-available RNAi molecule design computer programs. Synthetic shRNA/siRNA duplexes of HPLC grade may be purchased from any of numerous suppliers, such as Qiagen or IDT.

If there are no commercially-available siRNA or shRNA clones for a Target Gene (and shRNAs and/or siRNAs that are designed using computer software do not demonstrate, for example, desirable efficacy), a "shotgun" approach may be employed. For example, shRNA expression clone synthesis technology, developed by SilereTech, enables the synthesis of a "shotgun" library of shRNA expressing vectors for a given target sequence (e.g., Target Gene). The shotgun library provides thousands of RNAi candidates that are randomly distributed along the target sequence. From the shotgun library, numerous shRNA expressing vectors with varied potency and efficacy may be identified. The shotgun library provides a rich source of representative RNAi molecules (e.g., shRNAs or siRNAs) that do not require repeated synthesis, testing, or vector construction. With a proper screening process, shRNA and/or siRNA expression vectors of desired potency and efficacy may be readily identified.

The invention provides that the shRNA and/or siRNA sequences purchased, designed, or otherwise identified (using the above-mentioned "shotgun" approach) are, preferably, reviewed for unwanted "off-target" effects (i.e., binding to sequences other than the intended Target Gene). For example, the predicted "off-target" effects, or lack thereof, of a shRNA or siRNA molecule may be analyzed by conducting a BLAST search against irrelevant gene sequences of the NCBI GeneBank database.

In addition to shRNA/siRNA-mediated inhibition of gene expression, the invention provides that other appropriate methods may be employed to modulate the expression of one or more Target Genes. While the use of shRNA/siRNA to modulate gene expression is used throughout the present specification, the invention provides that such other appropriate methods may be used in addition to (or in replacement of) shRNA/siRNA methods. For example, the invention provides that other transcriptional and/or translation inhibitors may be employed to modulate Target Gene expression. Non-limiting examples of transcriptional modulators may include helix-turn-helix, zinc finger, leucine zipper, and/or helix-loop-helix proteins. Non-limiting examples of translational inhibitors/modulators may further include other forms of antisense technology, as well as siRNA-binding proteins, miRNAs, miRNA-binding proteins, small molecular inhibitors (e.g., anisomycin, cycloheximide, emetine, harringtonine and puromycin), and like compositions.

Enhanced shRNA Molecules

The invention further provides that a new, improved, and more efficacious method of using shRNAs to modulate Target Gene expression may be employed. In general, shRNAs consist of a stem-loop structure that may be transcribed in cells from an RNA polymerase III promoter within a plasmid construct. Expression of shRNA from a plasmid is known to be relatively stable, thereby often providing strong advantages over the use of synthetic siRNAs. shRNA expression units may be incorporated into a variety of plasmids and viral vectors for delivery and integration. shRNAs are synthesized in the nucleus of cells, further processed and transported to the cytoplasm, and then incorporated into the RNA-induced silencing complex (RISC) where the shRNAs are converted into active siRNA-like molecules (which are capable of binding to and preventing the translation of mRNA transcripts from Target Genes).

Plant and animal cells have recently been shown to express a novel class of short, single-stranded RNAs termed microRNAs (miRNAs). miRNAs are derived from larger precursors that also form a predicted RNA stem-loop structure. These miRNA precursor molecules are transcribed from autonomous promoters or are instead contained within longer RNAs. miRNAs appear to play a key role in the regulation of gene expression at the post-transcriptional level through translation repression. The biological activity of two miRNAs, *C. elegans* let-7 and lin-4, are well-established.

Similar to mRNAs, miRNAs are initially transcribed by RNA polymerase II into a long primary transcript (pri-miRNA), which contains one or more hairpin-like stem-loop shRNA structures. The stem-loop shRNA structures within the pri-miRNAs are further processed in the nucleus by the RNase III enzyme Drosha into pre-miRNA. Pre-miRNAs are transported to the cytoplasm by the nuclear export factor Exportin-5, where it interacts with a second RNase III enzyme known as Dicer. Dicer trims off the loop and presents the remaining double stranded stem to the RISC to seek-out target mRNAs for down-regulation.

Figure 2A:
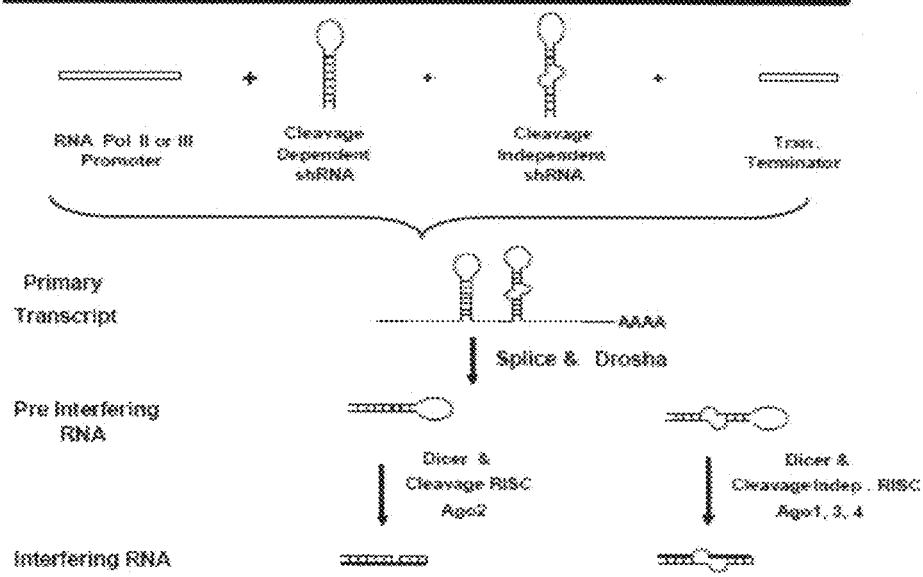
FIG. 2: (A) A diagram illustrating the cellular processing of the enhanced shRNAs encompassed and employed by the present invention. (B) A diagram illustrating two RNAi pathways.
Figure 2B:
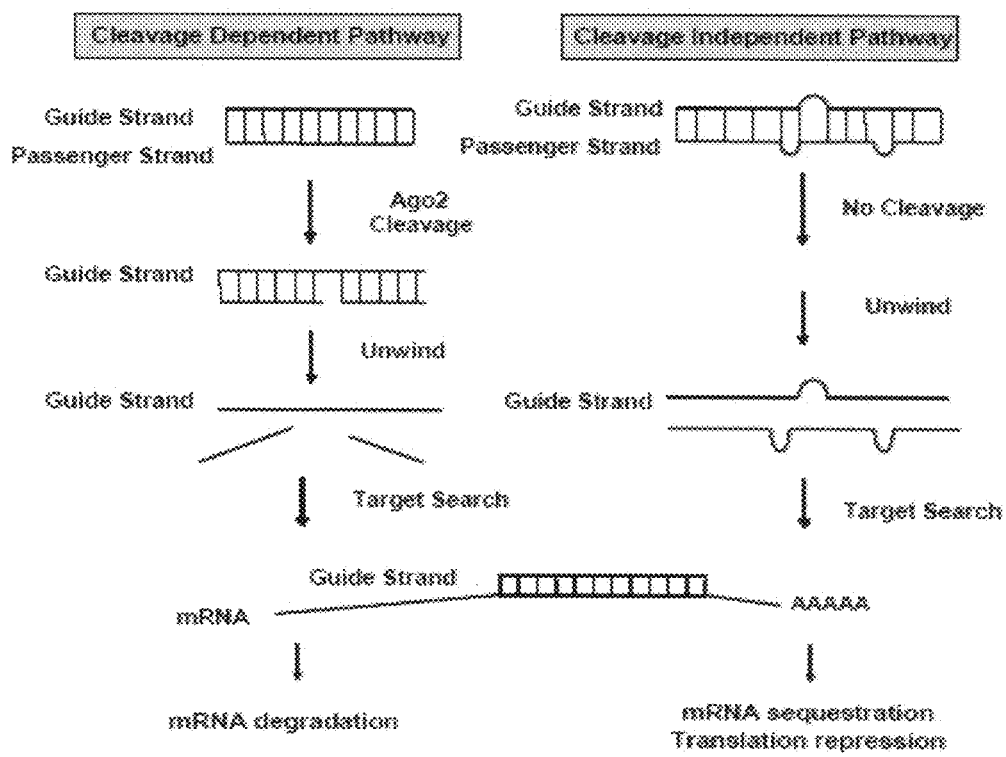

RISC may be characterized into cleavage-dependent RISC and cleavage-independent RISC (FIG. 2B). The invention provides that target-specific shRNAs may be designed to enter into and interact with either cleavage-dependent RISC or cleavage-independent RISC.

The enhanced shRNAs employed in the present invention comprise both types of shRNAs, namely, shRNAs designed to enter into and interact with both cleavage-dependent RISC and cleavage-independent RISC (FIG. 2A). The invention provides that a higher level of gene "knock-down," i.e., translation repression of Target Gene mRNA transcripts, is achieved using such enhanced shRNAs than other currently-available RNAi methods and compositions.

More specifically, the present invention provides methods and compositions for the synthesis of novel shRNA molecules that may be transcribed endogenously in human, animal and plant cells, for the purpose of "knocking down" the expression of one or more Targeted Genes. The shRNAs of the present invention simultaneously enter both cleavage-dependent RISCs and cleavage-independent RISCs, and inhibit the expression of a targeted mRNA containing a complementary target sequence (FIGS. 2A and 2B).

The invention provides that nucleic acid sequences, and constructs thereof, are used that encode one or multiple sets of shRNAs, wherein at least a portion of the shRNAs structurally resemble miRNAs. The resulting shRNAs induces degradation of a Target Gene mRNA produced in the cell, wherein the shRNAs contain a complementary target sequence or otherwise inhibits translation of such mRNA.

The constructs encoding the enhanced shRNAs described herein comprise a promoter, which is operably linked to a sequence encoding a precursor of the enhanced shRNAs. Preferably, the promoter is preferentially active in the targeted tumor tissues (i.e., it is a tumor tissue-specific promoter). Introduction of such constructs to host cells may be effected under conditions whereby the enhanced shRNA precursor transcript is produced, which is subsequently excised from such precursor by an endogenous ribonuclease. The resulting mature shRNAs may then induce degradation of Target Gene mRNA transcripts produced in the cell or otherwise repress translation of such mRNAs.

The enhanced shRNAs encompassed and employed by the present invention are, preferably, about 19-24 nucleotides long, or more preferably, about 21 or 22 nucleotides in length. The enhanced shRNAs may be designed so as to hybridize to any RNA transcript with a high degree of specificity. Preferably, a first portion of the enhanced shRNAs are designed to be perfectly (about 100%) complementary to the target sequence within the targeted RNA (e.g., mRNA). Still further, a second portion of the enhanced shRNAs are preferably designed to be perfectly (about 100%) complementary to the target RNA at positions 2-10, along with thermodynamically-favorable interspersed mis-matches at the remaining positions (FIGS. 10 and 11).

Accordingly, a first aspect of the enhanced shRNAs will, preferably, promote the cleavage of mRNAs bearing a fully complementary target site, while a second aspect of the enhanced shRNAs will, preferably, inhibit expression of mRNAs bearing partially complementary sequences (without necessarily inducing cleavage). The invention provides that simultaneous expression of both aspects of the enhanced shRNAs in cells establishes conditions within effected cells such that RNA interference may be activated through cleavage-dependent and cleavage-independent processes. The enhanced shRNAs may be designed so as to target a 3' or 5' untranslated region of the Target Gene mRNAs or coding regions thereof.

As described above, miRNAs are excised from precursor molecules that include a predicted RNA stem-loop structure. This RNA stem-loop structure of the enhanced shRNAs molecules encompassed and employed by the present invention may be designed such that it is recognized and properly processed by a ribonuclease (e.g., an RNAse III-type enzyme, such as Drosha and Dicer, or an enzyme having the recognition properties thereof), with the resulting excision of the mature siRNAs and miRNAs. Such precursor stem-loop structures may be about 40 to 100 nucleotides long or, preferably, about 50 to 75 nucleotides long. The stem region may be about 19-45 nucleotides in length (or more), or more preferably about 20-30 nucleotides in length. The stem may comprise a perfectly complementary duplex (but for any 3' tail); however, bulges or interior loops may be present, and even preferred, on either arm of the stem. The number of such bulges and asymmetric interior loops are preferably few in number (e.g., 1, 2 or 3) and are about 3 nucleotides or less in size.

The stem regions of the enhanced shRNAs comprise passenger-strands and guide-strands, whereby the guide-strands contain sequences complementary to the target RNA (and provide guidance for target sequence search). Preferably, the G-C content and matching of guide stand and passenger strand is carefully designed for thermodynamically-favorable strand unwind activity with or without endonuclease cleavage. Furthermore, the specificity of the guide strand is preferably checked via a BLAST search. The terminal loop portion may comprise about 4 or more nucleotides (preferably, not more than 25). More particularly, the loop portion is preferably 6-15 nucleotides in size. The precursor stem loop structure may be produced as part of a larger, carrier transcript (the primary transcript) from which the shRNAs are excised, or it may be produced as a precise transcript. Splice donor and acceptor sequences may be strategically placed in the primary transcript sequence to promote splicesome-mediated nuclear processing.

In certain embodiments, the enhanced shRNA-encoding sequence may comprise stem sequences of naturally occurring miRNAs (such as miR-30) to generate miRNAs suitable for use in inhibiting expression of any Target Gene. While the presence of a miR-30 loop may be desirable, the invention provides that variations of that structure may be tolerated, wherein loops may be used that are greater than 72%, preferably greater than 79%, more preferably greater than 86%, and most preferably, greater than 93% identical to, for example, the miR-30 sequence (determined using well-known computer programs such as the BESTFIT program (Wisconsin Sequence Analysis Package, Version 8 for Unix, Genetics Computer Group, University Research Park, 575 Science Drive, Madison, Wis. 53711)). The enhanced shRNA designs of the invention preferably mimic miRNAs expressed in the target tissue.

The enhanced shRNA encoding sequences (i.e., the sequences encoding the enhanced shRNAs precursors) may be present in a construct in operable linkage with a promoter. Appropriate promoters may be selected based on the host cell and effect sought. Suitable promoters include constitutive and inducible promoters, such as inducible RNA polymerase II (pol II)-based promoters. Examples of suitable promoters include the tetracycline inducible or repressible promoter, RNA polymerase I or III-based promoters, the pol II dependent viral promoters, such as the CMV-IE promoter, and the pol III U6 and H1 promoters. The bacteriophage T7 promoter may also be used (in which case, it will be appreciated, that the T7 polymerase must also be present).

The constructs encoding the enhanced shRNAs may be introduced into host cells using any of a variety of techniques and delivery vehicles well-known in the art. For example, infection with a viral vector comprising one or more constructs may be carried out, wherein such viral vectors preferably include replication defective retroviral vectors, adenoviral vectors, adeno-associated vectors, lentiviral vectors, or measle vectors. In addition, transfection with a plasmid comprising one or more constructs may be employed. Such plasmids may be present as naked DNA, or may be present in association with, for example, a liposome (e.g., an immunoliposome). Still further, the delivery vehicle may consist of immunolipoplexes, RGD targeted nanoparticles, RGD targeted liposomes, nanoparticles, aptamers, dendrimers, chitosan, or pegylated derivatives thereof. The nature of the delivery vehicle may vary depending on the target host cell.

In-vivo delivery of the enhanced shRNA-encoding constructs may be carried out using any one of a variety of techniques, depending on the target tissue. Delivery may be, for example, achieved by direct injection, inhalation, intravenous injection or other physical methods (including via micro-projectiles to target visible and accessible regions of tissue (e.g., with naked DNA)). Administration may further be achieved via syringe needles, trocars, canulas, catheters, etc., as appropriate.

Testing Efficacy of RNAi Molecules in-Vitro on Cancer Cell Lines

The shRNAs or siRNAs (and/or other transcriptional and/or translational modulating compositions) that are selected to regulate Target Gene expression are, preferably, tested in vitro on human cancer tissue culture cell lines (e.g., NCI60). While the present specification makes reference to testing the efficacy of the shRNAs and siRNAs that are selected to modulate Target Gene expression, those of ordinary skill in the art will appreciate that such testing should also be conducted to assess whether any additional or other transcriptional and/or translational modulating compositions that may be used in practicing the invention exhibit desired efficacy.

For each Target Gene, cell lines exhibiting similar, abnormal expression levels for such Target Gene are preferably used. In many cases, the cell lines may be obtained from ATCC. The invention provides that, in some cases, tumor cell lines derived from autologous cancer cells may also be reanalyzed for expression—similar to original harvested tissue and utilized for subsequent validation of shRNA/siRNA effect. The effect of such shRNAs/siRNAs is, preferably, analyzed with and without unique delivery vehicles.

More specifically, the selected cell line will be transfected with each shRNA/siRNA duplex at an effective dose range to determine the most optimum dose for each Target Gene. For example, the Block-It™ lipofectamine-based RNAi transfection kit may be used for such analysis (Invitrogen, Carlsbad, Calif.). The transfection efficiency of each cell line will be optimized using the fluorescent oligonucleotides provided with such kit. Quantitative RT-PCR analysis may be used to determine Target Gene mRNA levels in the selected cell line transfected with such shRNAs/siRNAs (or a control non-silencing shRNA or siRNA duplex).

The effective dose range (e.g., 50 nM to 250 nM) and percentage knock-down of each shRNA/siRNA duplex are preferably determined. Next, the most effective siRNA molecule or shRNA constructs for a given Target Gene may be selected for further study (or use in treating a patient as described herein). In certain preferred embodiments, the characterization of each siRNA/shRNA for each Target Gene is recorded in a database for future reference (and for future Target Gene selection decisions). An additional aspect of this invention is the contribution of the resulting gene perturbation data towards improving a gene network database computational system through the acquisition of non-confounded data derived from human source material.

Next, the ability of each shRNA/siRNA to suppress target protein and tumor cell growth is measured. To demonstrate cell growth arrest, cells from the selected cell line may be seeded the night before at 50% confluency and then transfected with an effective dose of the designed shRNA/siRNA molecule(s). At 24, 48 and 72 hours post-infection, viable cells may be enumerated by tryptan blue exclusion. Control culture for which expression of the Target Gene is not abnormally elevated will be transfected with the same dose of the shRNA/siRNA molecules to determine tumor cell specificity of the RNAi molecule(s) employed. Transfection efficiency of both cell types is, preferably, monitored using fluorescent oligonucleotides—in order to correct variation in transfection efficiency.

Total RNA from transfected cells may be harvested and the Target Gene contained therein may be subjected to semi-quantitative qRT-PCR analysis. The invention provides that preferred shRNA/siRNA targets exhibit effective curtailment of cell growth only in selected, over-expressed cell lines. If no suppression of tumor cell growth and quantitative reduction of mRNA is observed, the shRNA/siRNA candidate should be further tested, preferably in connection with a multiplex treatment strategy in combination with other RNAi molecules. The present invention provides that single target knock-down may not be entirely effective to completely suppress tumor cell growth, as redundant and overlapping pathways may compensate for the effects of a single shRNA/siRNA. Accordingly, the invention provides that multiple, such as 2, 3, 4, 5, or more, different shRNAs/siRNAs may be designed and used to "knock-down" the expression of a Target Gene—to effectively suppress tumor growth. In still further embodiments, the invention provides that multiple, such as 2, 3, 4, 5, or more, different shRNAs and/or siRNAs may be designed, tested, and used to "knock-down" the expression of multiple Target Genes.

After testing such siRNAs/shRNAs on an individual basis, the effect of a combination of siRNAs/shRNAs may be examined. Such multiplex treatment may be identical in condition to the singular siRNA/shRNA treatment described above. Various combinations of siRNAs/shRNAs may be tested as described for the singular siRNA/shRNA with or without the presence of delivery vehicle (e.g., nanoparticle or oncolytic virus). Multiplex treatment may be delivered with a single RNAi molecule expression vector expressing multiple RNAi molecules, or multiple RNAi molecule expression vectors expressing multiple RNAi molecules.

In addition to the foregoing, animal models, such as the SCID mouse (and derivatives thereof), may be used as human tumor tissue growth systems and the administration of RNAi constructs may be used to demonstrate the delivery, targeting, safety and overall efficacy of the RNAi construct being evaluated.

Parallel Processes

In certain embodiments, the invention contemplates that more traditional methods of treating, preventing, and monitoring cancer may be employed before, during (i.e., concurrent with), or after the methods of the present invention.

Following the procedures for detecting, diagnosing, and treating cancer described herein, the invention further provides that certain monitoring steps may be undertaken to ensure the targeted cancer does not return and/or to maintain the target cancer cells at manageable and/or safe levels. Preferably, such monitoring steps may be carried out using flow cytometry.

Diagnostic and Therapeutic Kits & Compositions

In certain additional embodiments of the present invention, kits are provided for carrying out certain methods described herein. The invention provides kits that comprise, for example, (i) a password or other authenticating information that provides a physician or other individual with access to a central database, instructions, and/or web-based software that enables him/her to identify a Target Gene and/or design an appropriate RNAi molecule (based on microarray, genomic DNA, and/or proteomic information provided to such database and/or web-based software); (ii) delivery vehicles capable of receiving and incorporating one or more RNAi molecule expression cassettes (or other sequences encoding desired transcriptional and/or translational modifiers) for delivery to a patient; and/or (iii) other surgical instruments and disposables that may be necessary to carry out the methods described herein.

The following examples are provided to further illustrate the compositions and methods of the present invention. These examples are illustrative only and are not intended to limit the scope of the invention in any way.

EXAMPLES

The following provides a non-limiting example of how the methods described herein may be used to identify a set of Target Genes in an individual suffering from cancer based on differential mRNA and protein expression patterns (in malignant versus non-malignant tissues). Furthermore, the following demonstrates that RNAi molecules may be designed and used to modulate the expression of such Target Genes to achieve a therapeutic effect.

Example 1

Process for Reducing Cancer Cell Growth

Patient Selection

Patient-1 is a 72-year old male with melanoma and a history of multiple recurrent disease episodes. He initially underwent two surgical resections without adjuvant therapy. At the time of the third recurrence, on Mar. 9, 2005, an auxiliary node was resected and tissue was processed at the Mary Crowley Medical Research Center (Dallas, Tex.).

Prior to surgery, an IRB-approved tissue harvest consent was obtained. A normal lymph node and skin tissue were resected for comparative analysis. Histologic review demonstrated 95% cancer cells in the resected node. The specimens were analyzed for differential and discriminatory genomic and proteomic expression as described herein. On Jan. 11, 2006, a PET scan identified areas of uptake in the left supraclavicular region, the right pericardiophrenic region, a retroperitoneal node, as well as several ill-defined lung nodules that were consistent with metastatic disease. These lesions were not resectable and Patient-1 was biopsied (supraclavicular node) on Jan. 26, 2006 a second time for genomic and proteomic analysis. Patient-1 received concurrent chemoradiotherapy from Feb. 13, 2006 through Mar. 17, 2006 with temozolomide and 45 Gy to the left supraclavicular nodal region. Patient-1 remains alive with stable disease.

RNA Amplification and Microarray Analysis

RNA was extracted from the malignant and non-malignant tissues described above using a PicoPure RNA Isolation kit (Arcturus Bioscience, Mountainview, Calif.). The quality of captured RNA was examined using an Agilent 2100 Bioanalyzer with RNA 6000 Pico LabChip (Agilent Technologies, Palo Alto, Calif.). The remainder of the samples were split into two equal portions for parallel RNA amplification and gene profile analysis. R-squared tests were performed to provide an indicator for the reproducibility of the duplicate portions.

RNA was amplified before labeling using a RiboAmp RNA amplification Kit (Arcturus Bioscience, Mountainview, Calif.). The quality of the amplified RNA was examined with BioAnalyzer. Genes exhibiting malignant tissue/non-malignant tissue expression level ratios equal to or more than >1 were determined to be "over-expressed." This ratio was determined with tissue-extracted nucleic acids (RNA), whereby the malignant tissue sample and normal tissue sample were analyzed in pair-wise fashion to identify genes that are significantly upregulated in the malignant tissue.

This "pair-wise" expression level analysis was carried out through binding reactions (i.e., GeneChip microarray hybridization reactions) with gene probes that were specific for 38,500 individual human genes. Gene expression profiles were established using bioinformatics analysis (Gene Spring 7.2 software). Specifically, hybridization and processing of GeneChip data were performed using an automated GeneChip Instrument System. Data acquisition, sample normalization and initial data analysis was performed with Affymetrix Microarray Suite (MAS) software. Gene probes with significant present cells (p-value<0.05) were selected following quantile normalization from bioconductor (www.bioconductor.org) to correct for systematic bias among samples.

Proteomics (2D-DIGEIMS) and Data Analysis 10 mg of malignant and non-malignant human lymph node tissue (from Patient-1) was lysed in 2-D lysis buffer containing 30 mM Tris-HCl (pH 8.8), 7 M urea, 2 M thiourea and 4% CHAPS. Cleared non-malignant protein lysate was labeled with a Cy3 CyDye fluor (green) for 30 minutes at 0° C., while malignant protein lysate was labeled with a Cy5 CyDye fluor (red) under the same conditions.

The reactions were terminated with the addition of lysine, and samples to be compared were mixed in an equal molar ratio. Destreak solution and rehydration buffer were added (100 µl each) before samples were loaded onto a 13-cm IPG strip (pH 3-10 linear range, Amersham) for isoelectric focusing (IEF) separation. After IEF was completed, the IPG strip was incubated with SDS-containing equilibration solutions and applied to a 9-12% gradient SDS gel (18×16 cm, 1-mm thickness). Electrophoresis was performed. The gel was subsequently scanned using a Typhoon Trio scanner (GE Healthcare/Amersham), and the images were analyzed using ImageQuant and DeCyder software. Protein spots of interest were excised and identified using MALDI-ToF/ToF mass spectrometry.

Gene Expression Profile Analysis and RNAi Selection

High-quality raw data from microarray and 2D-DIGE/MS were analyzed using the GNS network analysis system described above to identify potential RNAi targets (i.e., Target Genes). The list of targets was prioritized sequentially. First, proteins that were present in malignant tissue at levels that were at least 2-fold higher than in non-malignant tissue were identified (referred to herein as "highly-expressed proteins"). Second, the highly-expressed proteins were identified and functionally characterized for processes associated with oncogenesis, such as angiogenesis, apoptosis, cell cycle, cell cycle gene, DNA repair, migration, proliferation, signaling, stem cell association, and transcription activity through known literature searches. Third, highly-expressed proteins found to be implicated in cancer processes and elevated mRNA expression (>1.5 fold) in the tumor tissue were weighted as higher priority. Additionally, highly-expressed proteins known to exhibit high cross-species DNA sequence conservation were identified as higher priority. Fourth, for each of the proteins (and corresponding Target Genes) that met these criteria, protein-protein interactions fulfilling Gene Ontology (GO) assignments, which are frequently assigned to known cancer causing genes (determined through an enrichment analysis of GO terms assigned to oncogenes catalogued in the Cancer Census), were obtained from the human protein interaction databases of BIND, HPRD, and ResNet 33-35. The most highly-connected proteins (and corresponding Target Genes) were selected for further analysis.

Design & Synthesis of siRNAs

For each selected highly-connected protein (and corresponding Target Gene), the scientific literature was reviewed for the purpose of identifying commercially-available siRNA molecules from the Cancer Genome Anatomy Project's RNAi site of NCI (http://cgap.nci.nih.gov/RNAi) and from appropriate vendors (www.ambion.com). Commercial siRNA sequences of HPLC grade were available and purchased (synthetic predesigned protein specific siRNA duplexes) for each of the highly-connected proteins (and corresponding Target Genes).

In-Vitro Efficacy of siRNAs on Cancer Cell Lines

Selected siRNAs were tested on human cancer tissue culture cell lines HCT 116 Colon Cancer Cell Line (CCL247) and MDA-MB-231 Adenocarcinoma Breast (HTB26) from ATCC (Manassas, Va.). For each selected RNAi Target Gene, gene expression data compiled for NCI 60 cell lines were compared to identify those cell lines that have similar abnormally-high expression levels of the Targeted Genes (http://cmap.nci.nih.gov/Profiles/ProfileQuery) (http://discover.nci.nih.gov). Each selected cell line was tested for a group of identified Target Genes that are over-expressed. The cell lines were obtained from ATCC and utilized to validate siRNAs.

The RNAi activity for each siRNA on selected cell lines was determined. Specifically, the cells were transfected with each siRNA duplex across a range of doses to determine the optimum dose for each siRNA molecule using the (siPORT™ NeoFX lipid based RNAi transfection kit from Ambion, Austin, Tex.). A control non-silencing siRNA duplex with scrambled sequence was used to determine target mRNA level in selected cell lines. A time course of knock-down was then determined.

The ability of each siRNA molecule to suppress tumor cell growth was also measured. Specifically, cell growth arrest of transfected cells at Day-1, Day-2, Day-4, and Day-7 post-infection was tested using the well-known trypan blue exclusion method. Transfection efficiency was monitored with fluorescent oligonucleotides (Ambion, Austin, Tex.) in order to correct variation in transfection efficiency. RNA and protein samples were harvested from transfected cells and subjected to microarray and 2D DIGE/MS analysis (as described herein), with comparison of baseline at 24- and 72-hours post-transfection times.

Immunohistochemical Evaluation

Frozen malignant tissue cryosections and/or Formalin Fixed Paraffin Embedded sections were tested by immunohistochemically staining the cells expressing the selected proteins (i.e., those encoded by the Target Genes) using selected primary antibodies from BD Biosciences (San Diego, Calif.) and Abcam (Cambridge, Mass.). Staining was performed using the Universal Quick kit from Vector Laboratories Vectastain® (Burlingame, Calif.) and color development was achieved using a DAB (3,3'-diaminobenzenidine) substrate for the peroxidase enzyme antibody label (Vector Laboratories). Counter stain was achieved using Hematoxylin. Relevant unlabeled IgG antibodies were used as a negative control.

Western Blot Analysis

Paired tissue sample total protein—from both malignant and non-malignant samples—was tested by Western blot for the selected Target Gene protein expressions. Normal peripheral blood mononuclear cells, skin, and unaffected lymph node tissue were used as control. Total protein from cell lines expressing the selected Target Gene proteins were extracted and tested by Western blot analysis. Cell lines showing the expression of the selected Target Gene proteins were transfected using siPORT™ NeoFX™ Transfection Agent (Ambion, Austin, Tex.) with Silencer® Pre-designed siRNA for the target gene, transfection reagent alone and a Silencer® Negative Control #1 siRNA of 19 bp scrambled sequence with 3' dT overhangs (Ambion) for time periods of 24 hours, 48 hours, 4 days and 7 days. Total cell protein was extracted using CelLytic™ M (Sigma, Saint Louis, Mo.) and supplemented with Protease Inhibitor Cocktail (Sigma).

The protein concentration estimation was performed using Coomassie (Bradford) Protein Assay Kit (Pierce, Rockford, Ill.). The proteins were separated based on Molecular Weight using 15% Ready Gels (Bio-Rad, Hercules, Calif.) and SDS PAGE, transferred to High Bond PVDF membrane (Bio-Rad), probed with Target Gene protein-specific primary antibody (BD Biosciences), followed by enzyme labeled (HRP) secondary antibody and detected using the ECL Plus Western blotting detection reagents. Actin was also detected in the Western blots to show the loading concentration of samples. Band densities were estimated using AlphaImager 2000D (Alpha Innotech, San Leandro, Calif.) and NIH/Scion Image Software (Scion, Frederick, Md.).

Proteomics Results

Figure 4:
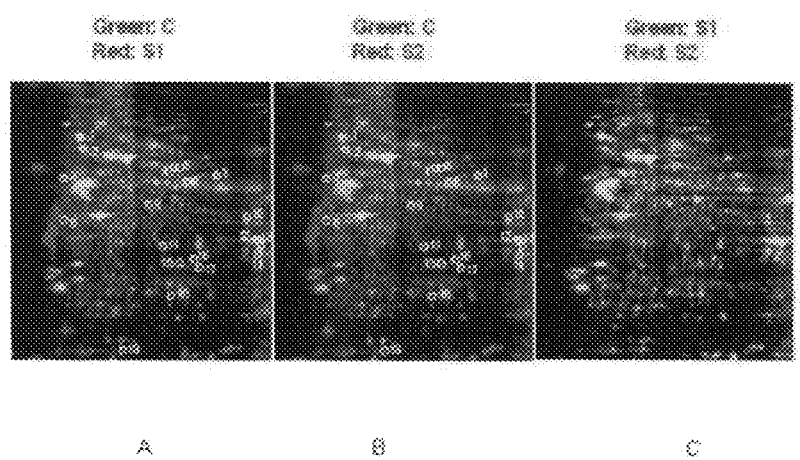
FIG. 4: 2-D gel electrophoresis images showing the 16 proteins described herein that were determined to be more than 2-fold over-expressed in malignant tissue (bright red) relative to normal tissue (as determined by mass spectrometry analysis). (A) Comparison of non-malignant tissue to malignant tissue on Mar. 9, 2005. (B) Comparison of non-malignant tissue to malignant tissue on Jan. 26, 2006. (C) Comparison of malignant tissue from Jan. 26, 2006 to malignant tissue from Mar. 9, 2005. The circled areas in panels A and B represent the prioritized proteins that were selected for further analysis, as described herein.

Sixteen proteins were identified with 2-fold differential expression by mass spectrometry. The proteins were identified as: MDH2, syntenin, Stathmin 1, elongation factor Tu mitochondrial precursor, pyruvate kinase 3 isoform 2, hnRNP L protein, hnRNP d-like protein JK TBP 10, hnRNP A2/B1, TPI1, VDAC2, heat shock protein 90, RACK 1, glyceraldehyde-3 phosphate dehydrogenase, immunoglobulin heavy chain binding protein, phosphoglycerate kinase 1, and adenylyl cyclase-associated protein. These potential targets were then prioritized via the protein network analysis system described above. Five proteins satisfied the selection criteria, which are listed in FIG. 9. An example comparison of protein profiles between non-malignant and malignant tissue is shown in FIGS. 3 and 4. Proteomic analysis performed on tissue harvested on Jan. 26, 2006, following a 10-month period of no detectable disease in the patient, indicated conservation of all original proteins, including the 5 selected target proteins (FIG. 4).

Connectivity of Priority Proteins

The priority proteins identified in Patient-1 following mass spectrometry of over-expressed 2D DIGE spots and parallel correlation with mRNA expression were further assessed for degree of connectivity by first order protein linkage analysis. The network analysis demonstrated highest connectivity of three proteins, namely, RACK1, Syntenin, and Stathmin 1 (FIG. 5). Based on this analysis, RACK1 was selected as the highest priority protein target for RNAi validation (i.e., the Target Gene of highest priority). Remarkable second order linkage (via intermediary protein interaction) between target proteins RACK1 and Stathmin 1 are shown in FIG. 5.

Immunohistochemical Staining Results

Figure 6:
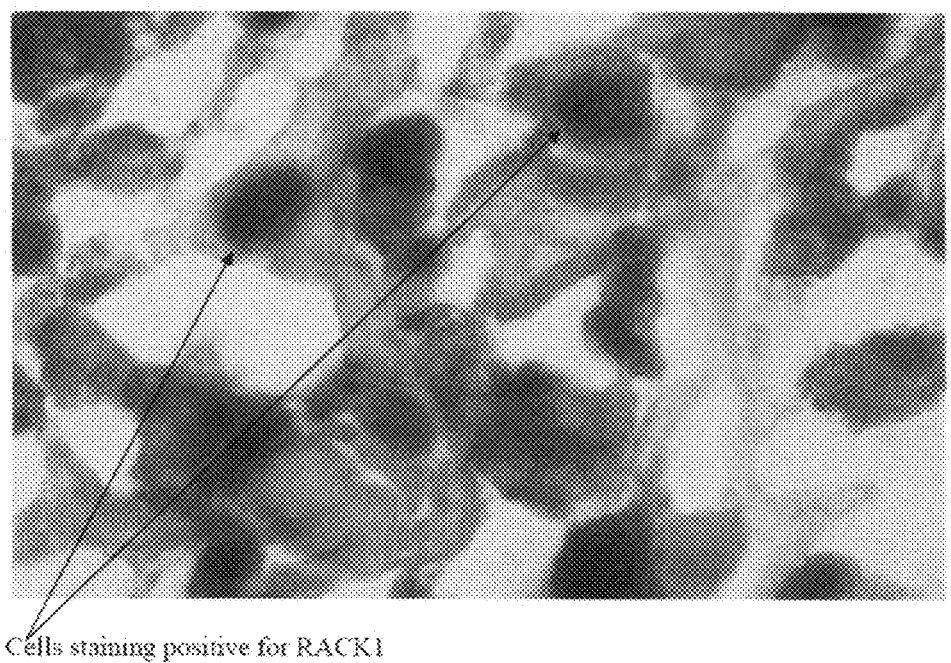
FIG. 6: Immunohistochemical staining of Patient-1 tumor cells in malignant tissue biopsied from Jan. 26, 2006.

Fresh frozen tissue from Patient-1 was harvested on Jan. 26, 2006 and subjected to immunohistochemical staining using mouse polyclonal antibody (diluted to a final concentration of 5 µg/ml) raised against RACK1 and detected using DAB substrate (as described above). The immunohistochemical staining demonstrated diffuse cellular involvement with the antibodies raised against RACK1 (FIG. 6), as well as Stathmin and Syntenin (data shown).

Western Blot Results

Antibodies raised against RACK1, Syntenin, and Stathmin 1 were used in Western blot analysis of proteins extracted from cancer cells lines HCT 116, CCL-247, MDA-MB-231, HTB-26, MDA-MB-435S and HTB-129. Differential expression of RACK1 in malignant and non-malignant tissue is shown by western blot analysis in FIG. 7A.

cDNA Microarray Results

Figure 8:
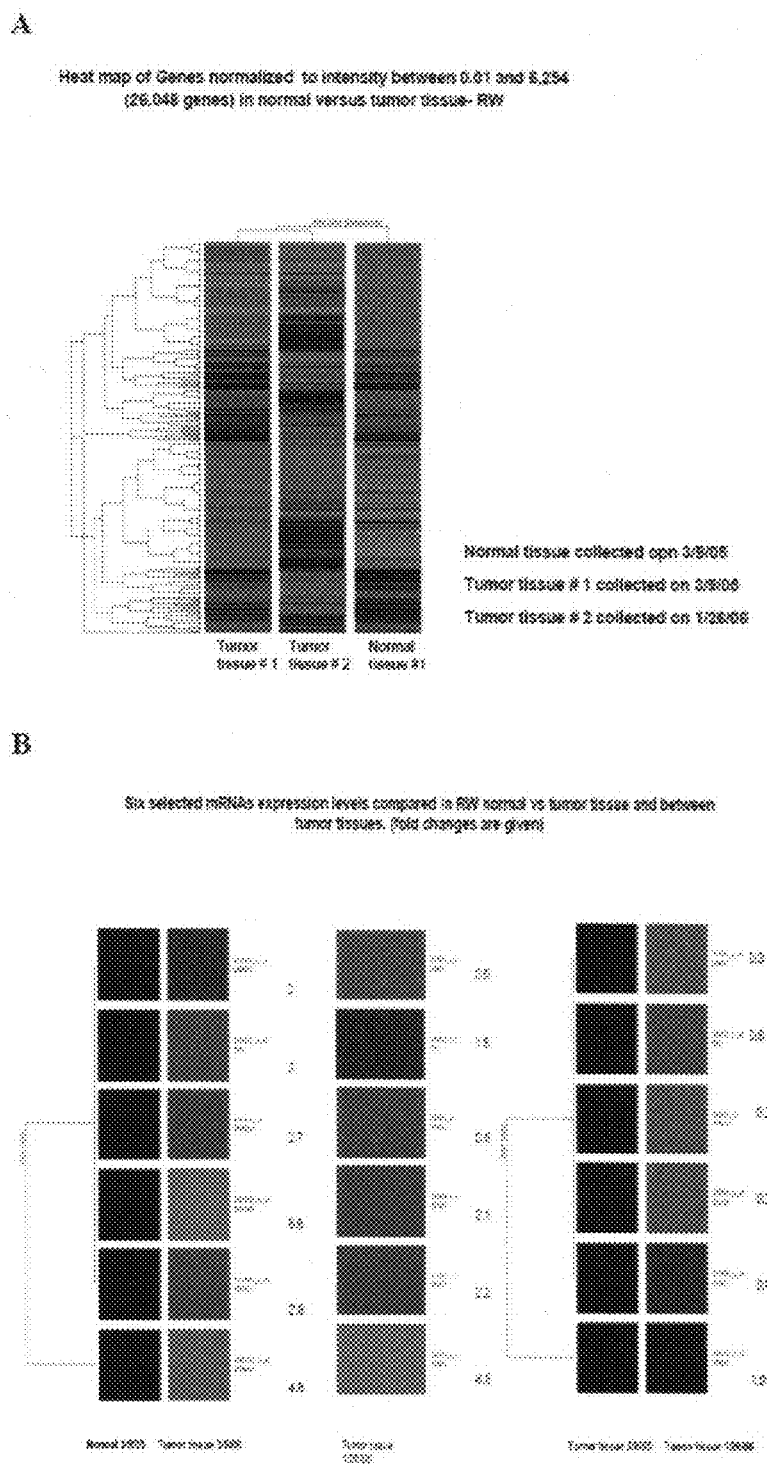
FIG. 8: (A) Differential gene expression analysis in malignant tissues (collected on Mar. 9, 2005, tumor tissue #1; Jan. 26, 2006, tissue #2) and normal tissue from the same patient. (B) Relative expression of highly-connected priority protein mRNAs in malignant and non-malignant specimens.

Referring to FIG. 8, microarray analysis demonstrated the considerable similarity in the identity of over-expressed genes in the malignant tissue harvested on Mar. 9, 2005 to Jan. 26, 2006. This correlation is consistent with the protein expression patterns described earlier. The ratios of mRNA expression in malignant versus non-malignant tissues of the top 5 prioritized Target Genes are shown in FIG. 9.

siRNA Knockdown Cell Lines siRNA knockdown demonstrated >80% knockdown of all 3 "priority" proteins, namely, RACK1, Syntenin, and Stathmin 1. FIG. 7B illustrates the siRNA knockdown of RACK1. The nucleic acid sequences used in the siRNA molecule to knockdown RACK1 expression were (a) sense 5'-CCUUUA-CACGCUAGAUGGUtt (SEQ ID NO:23) and (b) antisense 5'-ACCAUCUAGCGUGUAMGGtg (SEQ ID NO:24). A cell kill of >50% was correlated to RACK1 siRNA knockdown, as shown in FIG. 7C.

Example 2

Enhanced shRNA Molecules

Materials.

All oligonucleotides used in this Example were purchased from IDTDNA (Coralville, Iowa). The human embryonic kidney cells, HEK 293 cells, used in this Example were obtained from ATCC (Manassas, Va.) and were grown in DMEM (Gibco BRL, Invitrogen) supplemented with 10% fetal bovine serum (Hyclone®, Logan, Utah) and 2 mM L-Glutamine (Gibco BRL (Grand Island, N.Y.). The human colonic carcinoma HCT116 cells (ATCC CCL247) were obtained from ATCC (Manassas, Va.) and were grown in McCoy's 5A medium with 2 mM L Glutamine (Hyclone®, Logan, Utah) supplemented with 10% fetal bovine serum (Hyclone®, Logan, Utah).

RNA Isolation.

Total cellular RNA was isolated from CCL 247 colon cancer cell using the RNeazy mini-kit (Qiagen, Valencia, Calif.) by following the manufacturer's recommendations.

cDNA Synthesis.

The gene-specific cDNAs used in this Example were synthesized by RT-PCR. cDNA was first synthesized using total RNA and a gene-specific primer (SEQ ID NO:1) and Superscript III (Invitrogen, Carlsbad, Calif.). cDNA was then further amplified with gene-specific PCR primers (SEQ ID NO:2 and 3), which contained Nhe I and Bgl II sites at the ends thereof in order to facilitate cloning. The PCR products were subsequently digested with NheI and Bgl II, and purified from a 0.8% agarose gel before ligating into a NheI and Bgl II digested psiTEST plasmid.

Reporter-Gene cDNA Fusion Construct.

The psiTEST plasmid was purchased from Invitrogen (San Diego, Calif.). Double-stranded cDNA was digested with Nhe I and Bgl II and subsequently ligated with NheI- and Bgl II-digested psiTEST for directional insertion of the cDNA.

shRNA Expression Construct.

For each shRNA construct used in this Example, two sixty-nucleotide oligonucleotides with short overlapping complement sequences were purchased from IDTDNA (Coralville, Iowa). dsDNAs were synthesized by fill-in reaction with high-fidelity Taq DNA polymerase (Invitrogen, Carlsbad, Calif.), digested with Bam HI and Hind III. The appropriate sized DNA was subsequently isolated from agarose gel before insertion into Bam HI and Hind III sites of a pSilencer 4.1-CMV neo plasmid (Ambion, Austin, Tex.).

siRNAs.

The siRNAs used in this Example were purchased from Ambion (Austin, Tex.). The siRNAs used for the STMN1 (#16428) gene are represented by SEQ ID NO:4 (sense strand) and SEQ ID NO:5 (antisense strand).

Sequence Confirmation.

All sequence determinations were performed by SeqWright (Houston, Tex.). The following primers were used: psiTEST Forward (SEQ ID NO:6); psiTEST Reverse (SEQ ID NO:7); pSilencer Forward (SEQ ID NO:8); and pSilencer Reverse (SEQ ID NO:9).

Transfection of Cell Lines with siRNA or shRNA.

Reverse-transfection of cell lines was performed with siPort™ NeoFX™ or siPort™ Amine (Ambion, Austin, Tex.) via the protocol recommended by the manufacturer. Briefly, one hour before transfection, healthy growing adherent cells were trypsinized and resuspended in normal growth medium at $1 \times 10^5$ cells/ml. siPORT NeoFX was diluted (5 µl/well) into a predetermined volume of Opti-MEM 1 medium (100 µl/well) for each 6-well plate used. The plate was incubated for 10 minutes at room temperature. The siRNAs were diluted into Opti-MEM 1 medium for a final concentration of 10 nM-30 nM as required in 100 µl/well volumes of OptiMEM1.

The diluted siPORT NeoFX and siRNAs were combined and incubated for 10 minutes at room temperature. The transfection complexes were dispensed into empty 6-well plates (200 µl/well). The cells were gently mixed and provided with 2.3 ml of $1 \times 10^5$ cells/ml into each well of the 6-well plate. The plate was gently agitated to evenly distribute the complexes. Final volume of transfection was 2.5 ml/well. The plate was incubated at 37° C. After 8 hours of incubation, the cells were checked for cytotoxicity. If cytotoxicity was noticed, the media was replaced with fresh media after 8 hours. Otherwise, the media was replaced with fresh media after 24 hours of incubation. The cells were assayed, as described herein, following 24 hours, 48 hours and 4 days post-transfection for protein knock-down by Western blotting, flow cytometry or RT-PCR. Transfections were also performed with Lipofectamine™ 2000 (Invitrogen, Carlsbad, Calif.) using the protocol recommended by the manufacturer.

Secreted Alkaline Phosphatase Assay.

Secreted alkaline phosphatase was assayed with colorimetric EnzoLyte™ pNPP Secreted Alkaline Phosphatase Reporter Gene Assay Kit (AnaSpec, San Jose, Calif.). Cell culture media was first incubated at 65° C. for 30 minutes to inactivate the endogenous non-specific alkaline phosphatase. Assays were performed in 96-well plates, with 50 µl of media per well. Triplicate samples were used for each data point and compared against a standard concentration curve. The GraphPad Prism program was used to extrapolate concentration in units of samples from the standard curve.

Western Immunoblotting.

Cells were lysed with lysis buffer CellLytic-M (Sigma, Saint Louis, Mo.) and scraped off the surface of the culture dish. The cells were incubated at room temperature for 30 minutes on a slow shaker and briefly centrifuged. A small aliquot was removed for protein concentration estimation by Coomassie Bradford Plus Assay (Sigma, Saint Louis, Mo.), with BSA as a standard. The SoftMaxPro software program was used to calculate the protein concentration values (based on a standard curve).

Equal amounts of protein (5-20 µg) were separated via a pre-assembled gel (15 percent PAGE) using the Mini-Protein II Cell system (Bio-Rad). Following electrophoresis, the separated proteins were electro-transferred onto a PVDF membrane under standard conditions. The PVDF membranes were first blocked using a buffer containing 5% non-fat dried milk in DPBS-T overnight at 4° C. After two changes of wash buffer, proteins were tagged using a dilution of rabbit polyclonal primary antibody to Stathmin (Calbiochem-EMD, Biosciences, Inc. La Jolla, Calif.), followed by a HRP-conjugated secondary antibody (Abcam, Cambridge, Mass.). Chemiluminescent detection was performed using ECL Plus Western Blotting Detection reagents (GE HealthCare) with BioMax MR films (Kodak). Membranes were stripped and re-probed with a different antibody for a house-keeping protein, such as β-Actin (for control purposes). The membranes were scanned using an AlphaImager 2000 Digital Imaging System (Alpha Innotech Corporation). Quantitative densitometric analysis was carried out using the Beta Release 2 of Scion Image (Scion Corporation).

Flow Cytometry Analysis.

siRNA- and shRNA-transfected cells were Trypsin-treated and collected. An aliquot of cells was set apart for staining to evaluate the dead and apoptotic cells. The rest of the cells were fixed and permeabilized using the Fix and Perm reagent (BD Biosciences) for 20 minutes at 4° C. in the dark. Following permeabilization, cells were incubated with primary antibody in 100 µl of staining buffer for 30 minutes at 4° C. in the dark. Fluorescein-tagged secondary antibody was added to the cells and incubated for 10 minutes. The cells were subsequently washed and stored in staining buffer for acquisition of events using FACS caliber (BD Biosciences). Data were analyzed using FACS PRO software.

Viable Cell Count.

Sample cells were diluted 1:10 with DPBS and added to 50 µl of tryptan blue (Tryptan Blue 0.4%, Gibco BRL). Viable cells were counted using a hemacytometer.

Sequences and Oligonucleotides.

The nucleic acid sequences used for the STMN1 shRNA constructs and summarized in Table 1 below.

TABLE 1

| Sequence Designation | SEQ ID Number |
| --- | --- |
| 0015 | SEQ ID NO: 10 |
| 0016 | SEQ ID NO: 11 |
| 0017 | SEQ ID NO: 12 |
| 0018 | SEQ ID NO: 13 |
| 0019 | SEQ ID NO: 14 |
| 0020 | SEQ ID NO: 15 |
| 0021 | SEQ ID NO: 16 |
| 0022 | SEQ ID NO: 17 |
| 0023 | SEQ ID NO: 18 |
| 0024 | SEQ ID NO: 19 |
| 0054 | SEQ ID NO: 20 |
| 0055 | SEQ ID NO: 21 |
| 0056 | SEQ ID NO: 22 |

The shRNA constructs described herein comprise two nucleic acid sequences referenced in the above Table 1. Each shRNA construct is reference by a combination of the appropriate Sequence Designations shown therein. For example, shRNA constructs comprising Sequence Designations 0017 and 0018 in Table 1 above (i.e., SEQ ID NO:12 and 13) and referred to herein as "17/18" or "Construct 17/18." FIG. 10 illustrates the location of certain structural dimensions of these shRNA constructs, including the location of the sense sequence, anti-sense sequence, and mismatches thereof.

Design of shRNA and Expression Constructs.

Enhanced shRNAs were designed to mimic the framework of human pre-miRNA hsa-miR-30 by substituting the mature miRNA sequence with a STMN1-specific siRNA sequence at the stem region of the stem-loop structure. Two nucleotides juxtaposition to the STMN1-specific siRNA sequence were modified for efficient processing of the pre-miRNA to mature miRNA. The loop region was also enlarged to 15 bases for efficient Drosha processing of pri-miRNA to pre-miRNA.

Figure 11A:
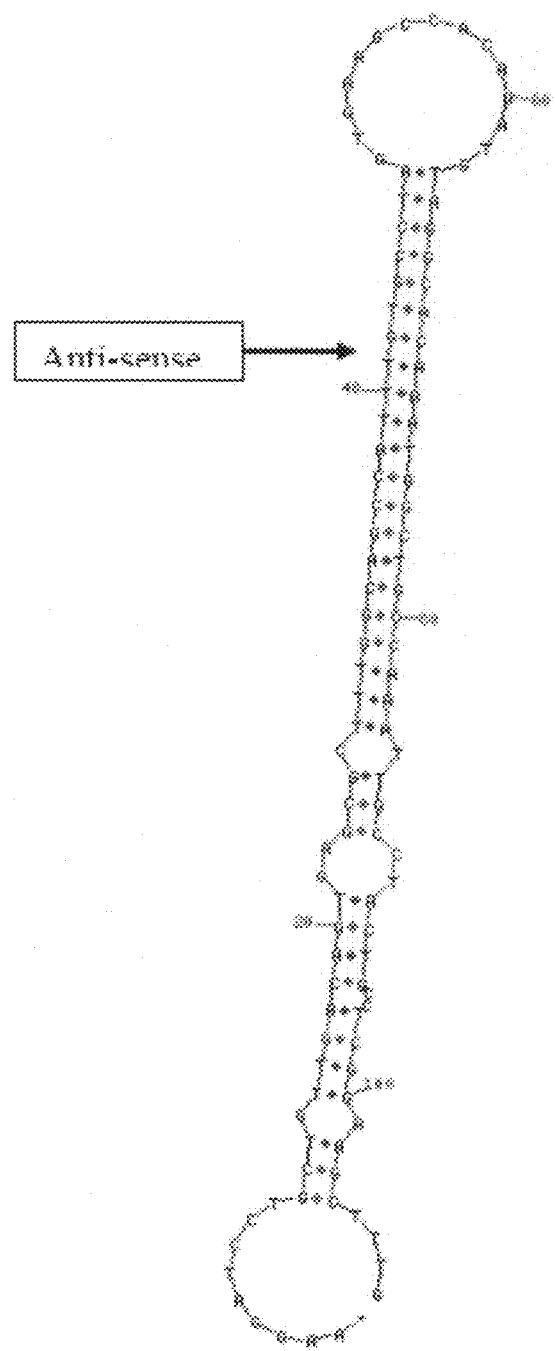
FIG. 11: (A) The predicted stem-loop structure of Construct 15/16. (B) The predicted stem-loop structure of Construct 17/18. (C)-(E) The predicted-stem loop structures of Constructs 54/18, 55/18, and 56/18, which contain mismatches and bulges either within the sense or anti-sense strand SEQ ID NOS.: 15 and 16 (11A); 17 and 18 (11B); 20 and 18 (11C); 21 and 18 (11D); 22 and 18 (11E).
Figure 11B:
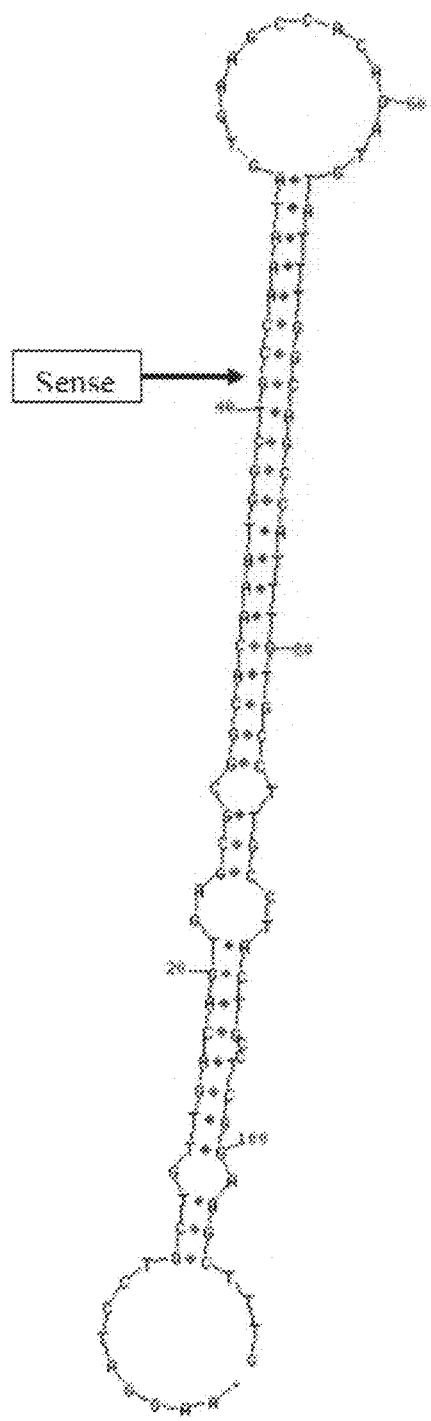
Figure 11C:
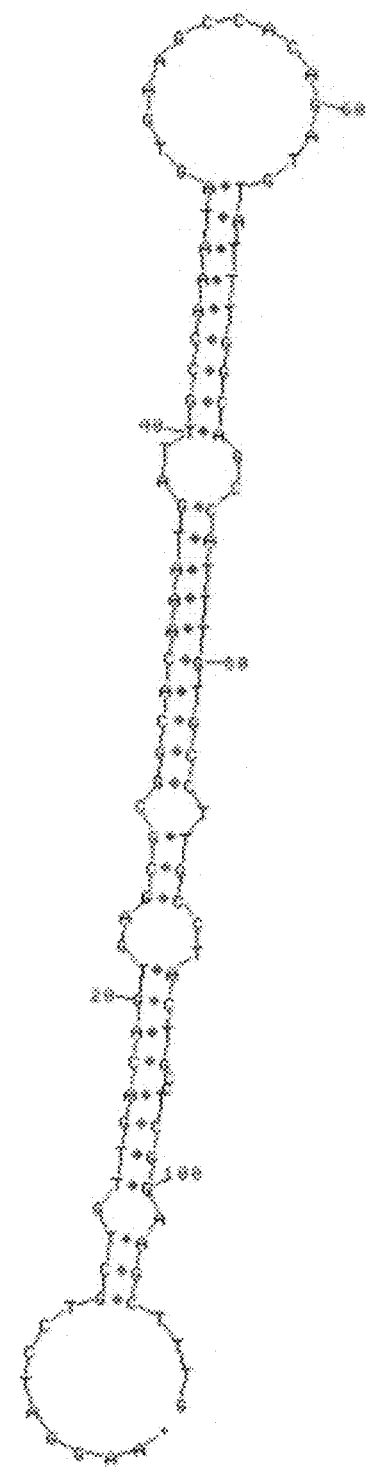
Figure 11D:
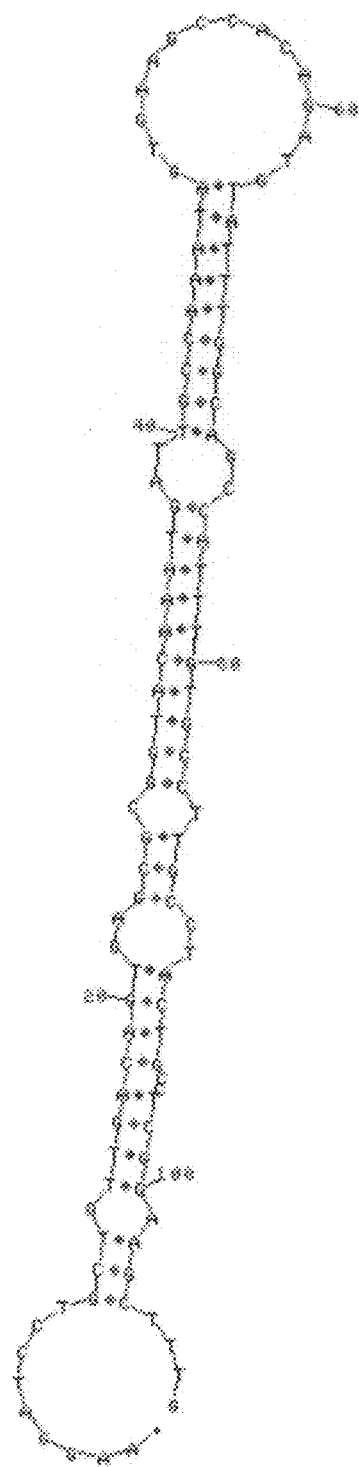
Figure 11E:
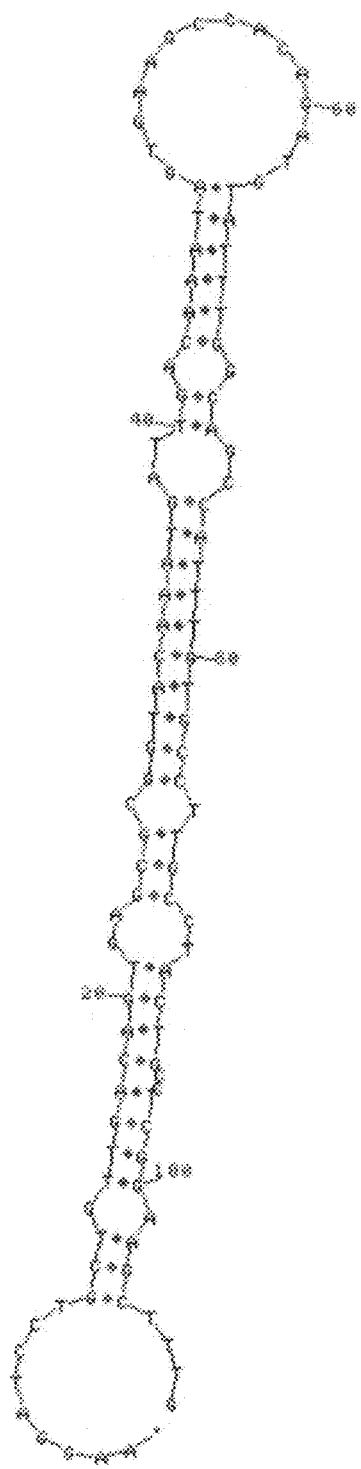

To test for the positional effect of the siRNA sequence, the STMN1-specific siRNA sequences were placed in both orientations—either on the ascending strand or on the descending strand of the stem of the stem-loop structure. The prototype designs were Construct 15/16 and Construct 17/18, with guiding strand (anti-sense) at the ascending strand and the descending strand of the stem-loop structure, respectively. The sequence for Construct 15/16 and Construct 17/18 are shown in FIG. 10. The predicted Construct 15/16 and Construct 17/18 stem-loop structures are shown in FIG. 11A and FIG. 11B, respectively.

Figure 12:
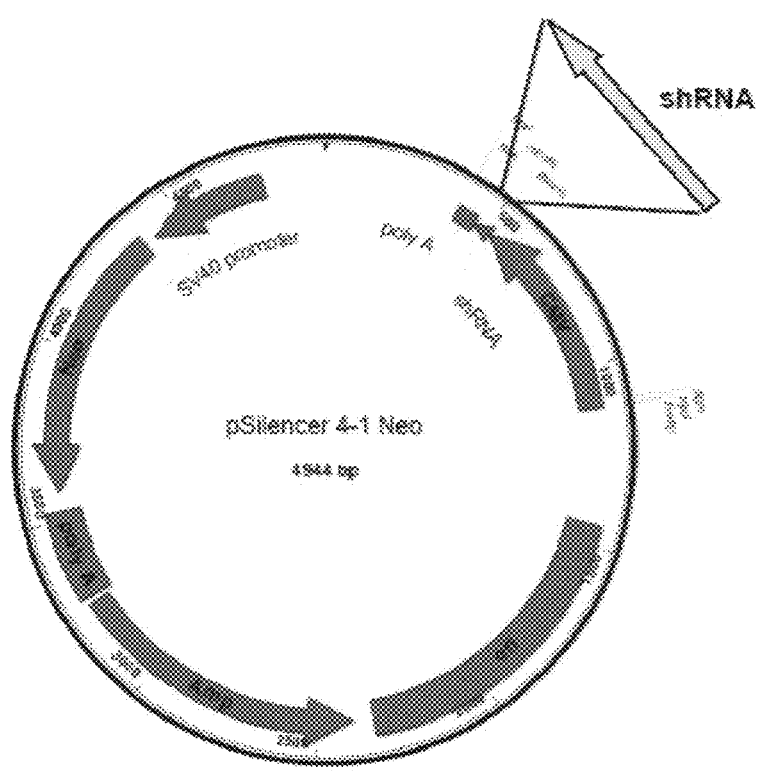
FIG. 12: A diagram showing the pSilencer 4-1 Neo vector described in the Examples below.

Additional STMN1-specific shRNAs were designed to introduce mismatches and bulges either at the sense strand or at the anti-sense strand to determine the structural-functional requirement and efficacy thereof. Introduction of mismatches at the sense strand was designed to test the hypothesis of this invention to shunt shRNA to additional RISC to provide more effective and target-specific knock-downs (i.e., repression of gene expression). The predicted structures for each shRNA, with mismatches, are shown FIGS. 11C (Construct 54/18), 11D (Construct 55/18), and 11E (Construct 56/18).

shRNA expression units were synthesized by fill-in reaction with oligonucleotides as described above. The synthetic shRNA expression units comprised Bam HI and Hind III sites at the 5' and 3' ends, respectively, to facilitate the insertion into the psilencer 4.1-CMV Neo expression vector (Ambion, Austin, Tex.), as shown in FIG. 12. The expression construct sequence was confirmed before used for RNA interference analysis, as described above.

Reporter-cDNA Transcription Fusion Constructs.

Introduction of siRNA or shRNA into mammalian cells rely on an efficient transfection and delivery system. The transfection efficiency varies widely from cell line to cell line. Thus, it is often difficult to obtain an effective and accurate assessment of target gene knock-downs for each siRNA or shRNA by examining the whole cell extract. Additionally, it is often difficult to assess the Target Gene knock-down for prolonged periods of time. Therefore, a reporter assay system was used, which revealed the efficacy of each siRNA and shRNA construct described herein, without any bias introduced by the transfection efficiency.

Figure 13:
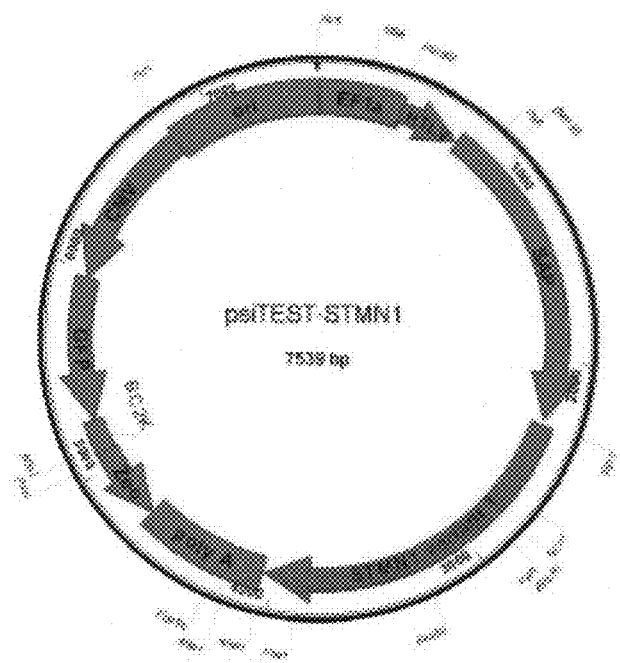
FIG. 13: A diagram of the psiTEST-STMN1 vector containing the STMN1 cDNA insert described herein.

The reporter-cDNA transcription fusion system (psiTEST) of Invitrogen (Invitrogen, San Diego, Calif.) was employed. The psiTEST system used a soluble form of alkaline phosphatase (sAP) as the reporter gene. sAP activity may be easily sampled and assayed from culture media. STMN1 cDNAs were synthesized by RT-PCR with gene specific primers, as described above. STMN1 cDNA was inserted into the psiTEST vector down stream from the mRNA sequence for the soluble form of the alkaline phosphatase gene to form a transcriptional fusion construct. The resulting fusion construct is illustrated in FIG. 13. It was envisaged that sequence-specific knock-down of STMN1 will result in knock-down of the transcripts of reporter gene-fusion expression, thereby leading to curtailment of sAP expression. Fusion constructs with STMN1 cDNA was sequenced and confirmed for the inserted cDNA sequence, as described above.

Reporter-cDNA Transcription Fusion Assay.

Figure 14:
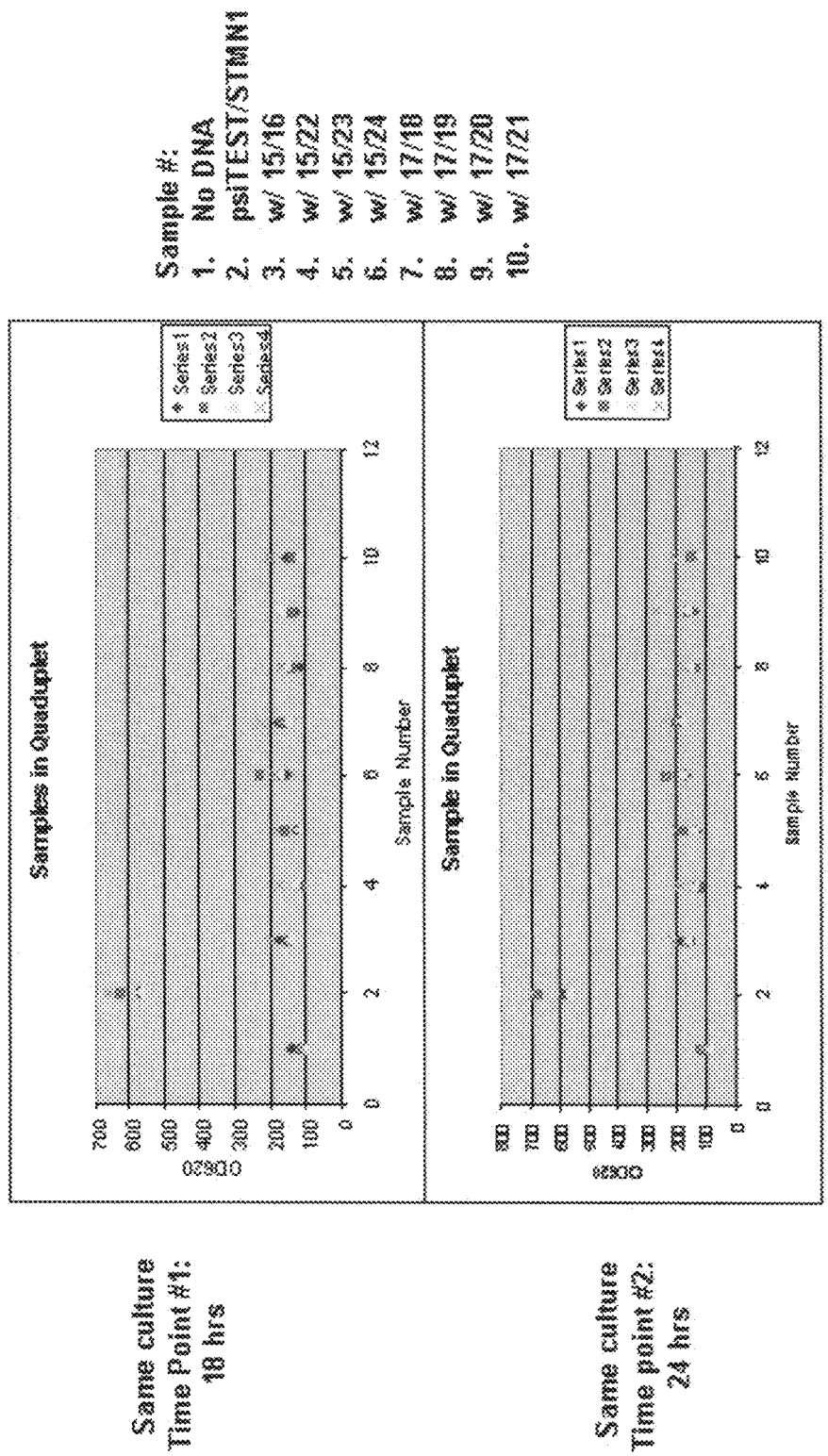
FIG. 14: Charts illustrating the reliability of the reporter-cDNA transcription fusion system used in the Examples below, which involved HEK-293 cells co-transfected with psiTEST/STMN1 and various shRNA constructs.

The reliability of the reporter-cDNA transcription fusion system was first determined. Specifically, HEK-293 cells were co-transfected with psiTEST/STMN1 and various shRNA constructs. The shRNA expression vector to psiTEST/STMN1 expression vector was co-transfected at a 3:1 ratio. For each transfection, triplicate samples were collected at 18 hours and 24 hours post-transfection, and assayed for alkaline phosphatase (AP) activity in the medium. AP assay was performed using pNPP, a calorimetric substrate for AP, vis-à-vis OD620 readings. FIG. 14 shows the results of this experiment.

As shown in FIG. 14, the assay process was very consistent—with triplicate samples, it showed little variation between the triplicates. The 24-hour samples exhibited a consistent pattern as the 18-hour samples with much shorter color development time, indicating increased accumulation of AP activity in the media. When compared to siTEST/STMN1 transfection alone (FIG. 14, sample #2), all shRNA co-transfection effectively reduced the sAP activity in the media (FIG. 14, samples #3-10). Mock transfection without any plasmid DNA showed very little background sAP activity contributing from the cell or serum (FIG. 14, sample #1).

shRNA Knock-Down Persists while siRNA Knock-Down Looses its Effect Over Time.

The abilities of the siRNAs and shRNAs to knock-down Target Gene expression were compared over a course of approximately 5 days. HEK-293 cells were reverse-transfected with reporter construct+non-specific DNA, or reporter construct+shRNA expression Constructs (Constructs 17/18, 17/19, 17/20, or 17/21), or reporter construct+siRNA (16428). A 3:1 molar ratio of shRNA and siRNA to reporter gene construct was employed. At 12 hours post-transfection, aliquots of samples were taken, and the culture media was replaced with fresh media to remove any residual siRNA or shRNA. The culture media was sampled at a regular interval for up to 5 days (media was not changed).

Figure 15:
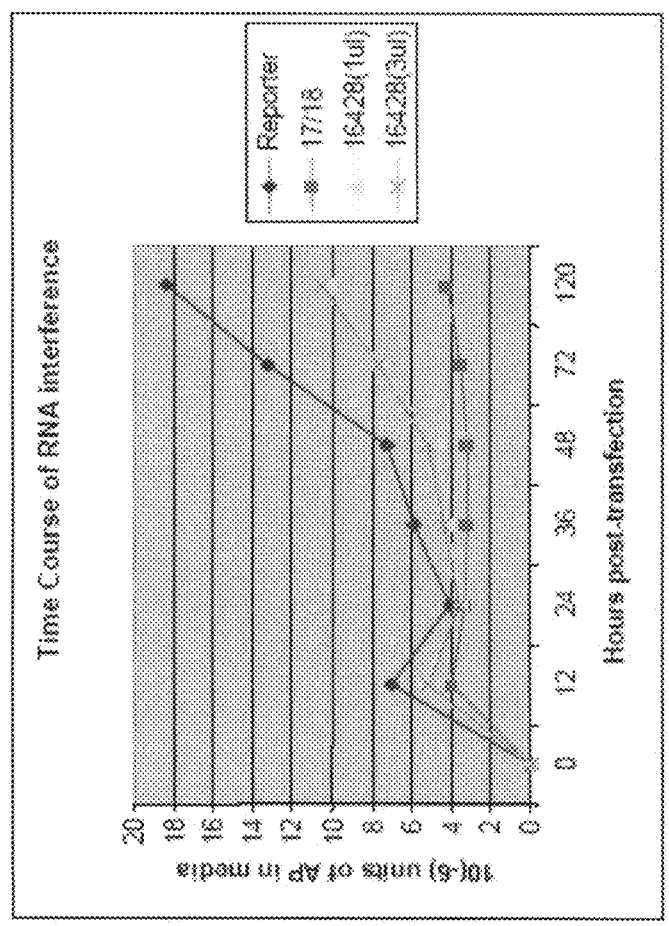
FIG. 15: A chart illustrating RNA knock-down by psiTEST/STMN1-alone and enhanced shRNAs in transfected cells over a period of time.

In order to compare sAP activity for each time point, the sAP assay was compared to a standard curve generated by known units of AP. FIG. 15 shows that psiTEST/STMN1-alone transfected cells continued to accumulate sAP activity in the culture media (blue line), whereas all shRNA co-transfected cultures exhibited reduced sAP expression. The 24-hour time point shows a reduced sAP activity in response to a washing step at the 12-hour time point.

When psiTEST/STMN1 was co-transfected with either 10 nM or 30 nM of 16428 siRNA (16428 being a STMN1-specific siRNA targeted at the same sequence as the shRNA constructs described herein), the sAP activity accumulates in a similar pattern as psiTEST/STMN1 transfection alone, albeit lower in sAP accumulation (FIG. 15, light blue and yellow lines). Thus, siRNA appears to be either less active or otherwise looses its activity over time. By Western blotting, it was determined that 10 nM of 16428 is the effective dose to knock-down STMN1 expression (data not shown); 3-fold excess of siRNA at 30 nM concentration appear to achieve a similar inhibition pattern as for 10 nM. At the saturation concentration of siRNA, the reporter expression appears to be inhibited initially, but the inhibition did not persist as it did with the enhanced shRNAs.

The fact that shRNAs were able to inhibit sAP expression over a 5-day period indicates that once transfected, shRNAs are able to continuously shut-down the expression of its targeted gene. Comparable siRNA is either not as effective, or looses its activity over time. These data show the considerable advantage, and prolonged activity, of the enhanced shRNAs described herein over conventional siRNAs.

Construct 17/18 phasing was more effective than Construct 15/16. The knock-down efficiency of Construct 17/18 was compared to that of Construct 15/16 by Western immunobloting with STMN1-specific monoclonal antibodies.

Figure 16:
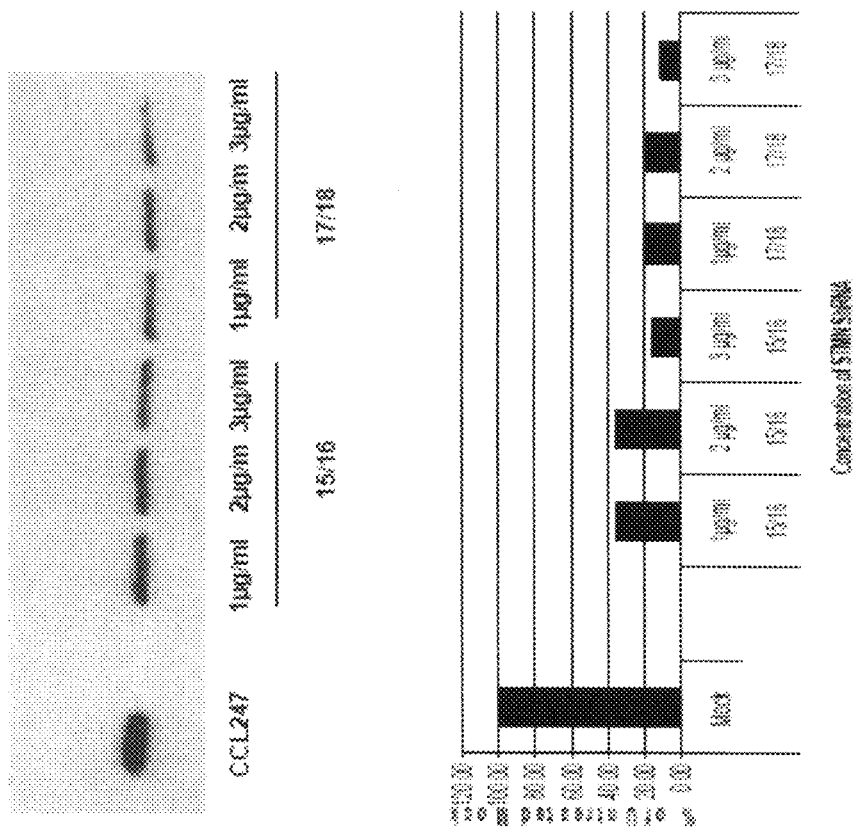
FIG. 16: (Top) An image showing Western blot results of the STMN1 protein. (Bottom) A bar graph illustrating STMN1 RNA knock-down by Constructs 15/16 and 17/18 at different concentrations.

CCL247 cells were transfected with 1, 2 or 3 µg/ml of either Construct 15/16 or 17/18. Total cellular proteins were harvested from transfected cells at 48 hours post-transfection and equal amounts of protein were loaded onto polyacrylamide gels for Western blot analysis, as described above. FIG. 16 shows that both Construct 15/16 and Construct 17/18 were able to knock-down the expression of the STMN1 protein when compared to protein isolated from mock transfected cells. Construct 17/18 appeared to be more effective than Construct 15/16.

Flow cytometry was also used to evaluate the population of transfected cells at the single-cell level. At 24 hours post-transfection, with 3 µg of either Construct 15/16 or Construct 17/18, both transfected cell populations exhibited effectively-reduced expression of STMN1 (when compared to media alone) (FIG. 17).

Figure 17:
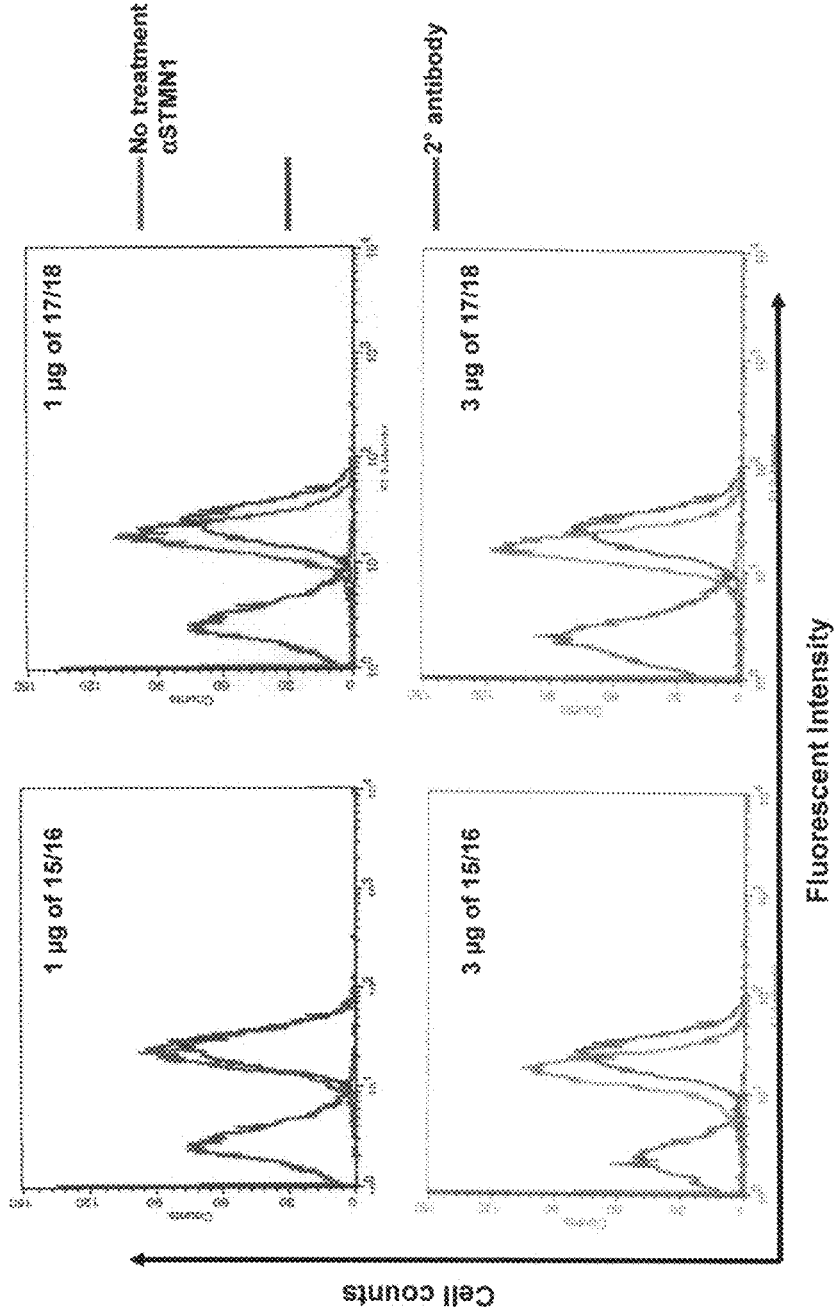
FIG. 17: Flow cytometry results showing the effect of Construct 15/16 and Construct 17/18 on STMN1 expression.

However, when 1 µg was used for either Construct 15/16 or Construct 17/18 (and single cell populations were analyzed by flow cytometry at 24 hours post-transfection), Construct 15/16 was not as effective as Construct 17/18 at 1 µg/ml (FIG. 17). Thus, positioning of the guiding strand sequence at either side of the stem provides active shRNA molecules; however, positioning the guiding strand at the descending strand of the stem-loop structure appears to be more effective than at the ascending strand. This empirical observation that positioning the guiding strand at the descending strand of the stem-loop structure provides a favorable advantage in effective dose, and indicates that such structure is preferred for shRNA processing and activity.

RNAi-Mediated Cell Death and Apoptosis.

Recently, Lovborg and colleagues utilized Hoechst 33342 as a reagent used for multi-parametric evaluation of apoptosis, wherein they demonstrated that apoptotic cells have increased permeability to Hoechst after fixation (Lovborg, et al. Mol. Cancer Ther. 2004; 3(5): 521-6). Propedium iodide (PI) is a nucleic acid-binding dye that is not permeable to cell membranes, only dead cells with permeable membranes (which become stained in the presence of PI dye). This procedure is routinely used by researchers to identify dead cells within a population of cells.

Figure 18:
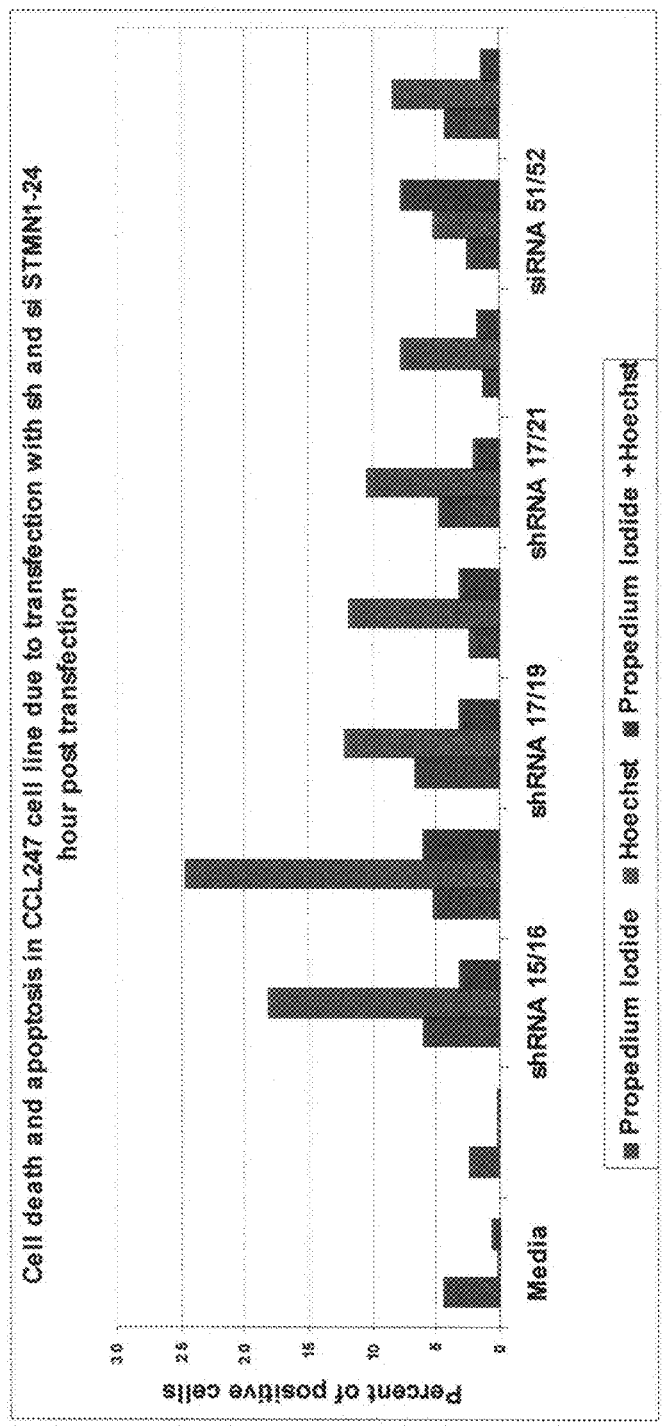
FIG. 18: A bar graph summarizing the cell death assays described herein for the enhanced shRNA-transfected cells described in the Examples below, wherein STMN1 protein expression was suppressed by such enhanced shRNAs.

On the other hand, Hoechst 33342 is also a nucleic acid-binging dye that needs to be transported into cells through an active transport system, in order to identify the live cell population. Lovborg and colleagues demonstrated that apoptotic cells with leaky membranes and condensed chromosomes appear to have higher fluorescent intensity than normal cells after fixation (fixed cells lack active transport for Hoechst 33342). PI and Hoechst 33342 provide a simple and quick assay system to evaluate shRNA-transfected cell populations. CCL247 cells were transfected with various shRNA constructs for STMN1. After 24 hours, the increased population of cells was observed to have increased Hoechst and PI fluorescence at the single cell level. The increase in fluorescence was observed for STMN1 shRNA transfected cells, but not for mock transfected cells (FIG. 18).

Enhanced Knock-Down with Combinatorial shRNA Designs Indicate Advantageous Formulation for RNAi.

Figure 19:
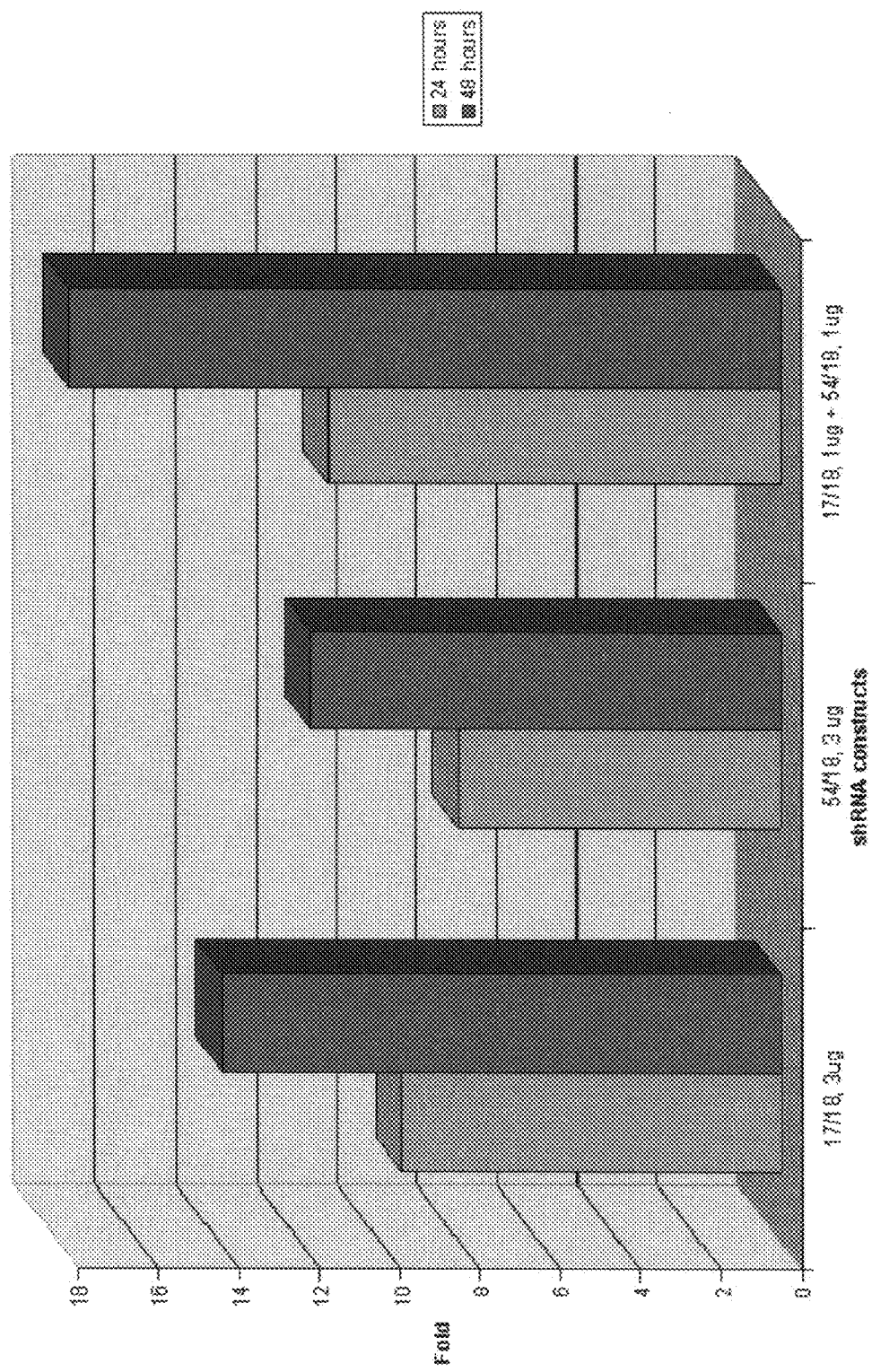
FIG. 19: A bar graph showing the reduction in STMN1 mRNA following the introduction of the enhanced shRNA molecules described in the Examples below.

The knock-down efficiency was further examined with Constructs 17/18 and 54/18 (17/18 with single mismatch) and in combination. CCL247 cells was either transfected with 17/18 or 54/18 alone or in combination. At 24 and 48 hours post-transfection, STMN1 mRNA knock-down was examined by qRT-PCR method and STMN1 protein expression was examined at the individual cell level by flow cytometry with STMN1 specific antibody. With a combination of 1 µg of 17/18 and 54/18, the treatment resulted in more effective reduction in STMN1 mRNA than 3 µg of either 17/18 or 54/18 alone (FIG. 19). In terms of promoting STMN1-specific mRNA degradation, the combination of 17/18 and 54/18 is an advantageous formulation.

Figure 20:
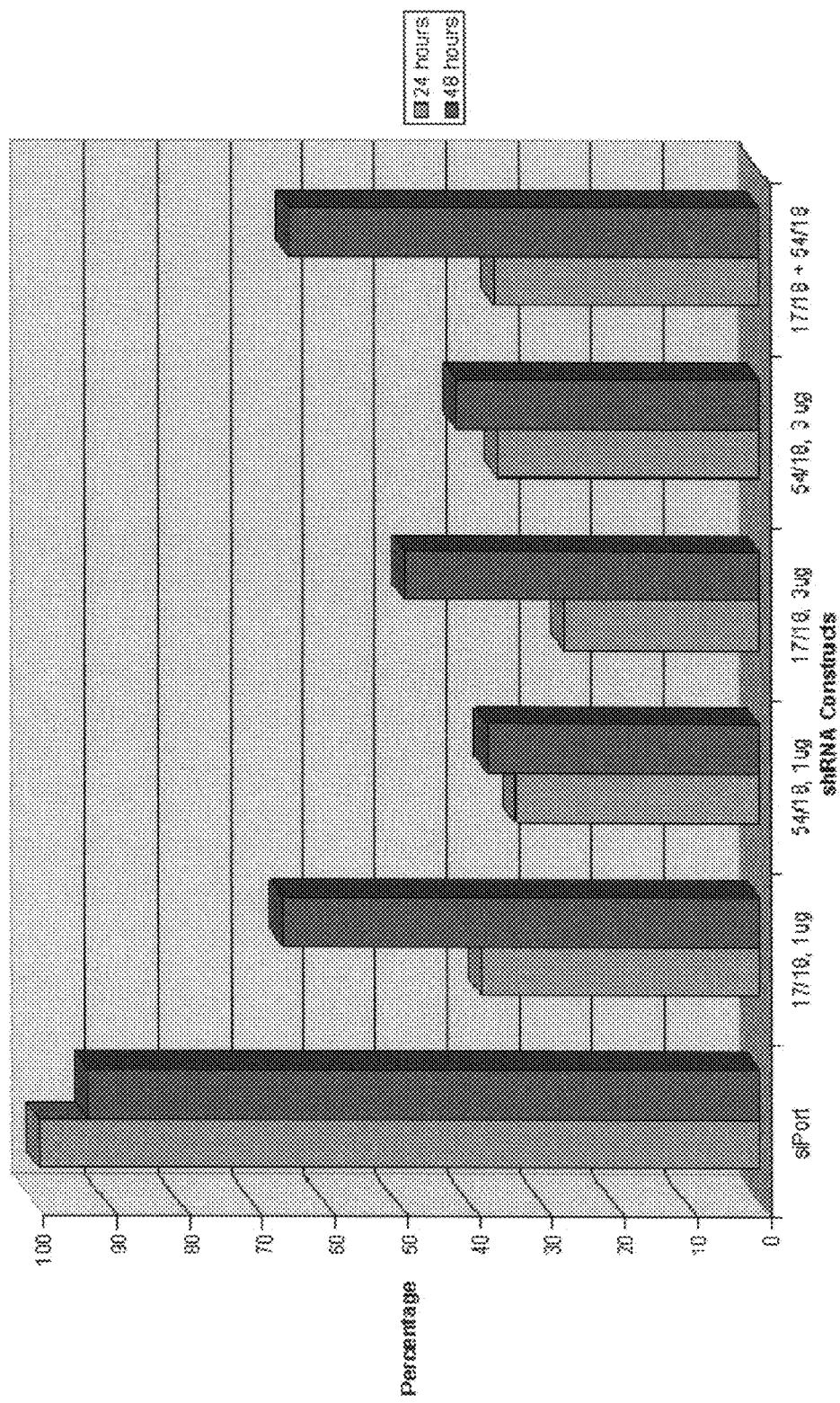
FIG. 20: A bar graph summarizing the results of flow cytometry analysis, which shows the percentage of STMN1-positive cells detected following the introduction of the enhanced shRNA molecules described in the Examples below.

At the cell population level, the combination of 17/18 and 54/18 appears to be similarly effective as the 17/18 or 54/18 alone at 24 hours post-treatment (FIG. 20). In addition, at 48 hours, cell recovery for the combination of 17/18 and 54/18 appears to be similarly effective as the 17/18 alone (FIG. 20). 54/18 treatment alone, however, resulted in a more prolonged effect, further persisting to 48 hours. Such data further demonstrate the effectiveness of the enhanced shRNA designs described herein to effectively reduce target protein expression levels.

The invention provides that using a combinatorial approach, particularly with the enhanced shRNAs described herein, provides a desirably efficacious RNAi formulation. Such formulations were shown to provide superior efficacy in comparison to other currently-available conventional molecules designed for RNA interference.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for treating cancer, which comprises:
   (a) obtaining a specimen of cancer tissue and normal tissue from a patient;
   (b) extracting total protein from the cancer tissue and normal tissue;
   (c) obtaining a protein expression profile of the cancer tissue and normal tissue;
   (d) identifying one or more over-expressed proteins in the cancer tissue, wherein a protein is considered to be over-expressed if the protein is found in the cancer tissue at higher levels than in the normal tissue;
   (e) identifying at least one prioritized protein from the one or more over-expressed proteins, wherein the prioritized protein is translated from an mRNA molecule that will serve as a target for an RNA interference molecule;
   (f) designing an RNA interference expression cassette to modulate the expression of at least one gene that encodes the mRNA molecule from which said prioritized protein is translated, wherein the RNA interference expression cassette encodes one or more RNA interference molecules that, individually or collectively, include:
   (i) a shRNA that comprises a first sequence that is about 19-24 nucleotides in length and is 100% complementary to a target sequence within the mRNA molecule wherein the first sequence comprises a cleavage dependent oligonucleotide that is cleavage dependent at a RNA-induced silencing complex (RISC) complex; and
   (ii) wherein the shRNA further comprises a second sequence that is about 19-24 nucleotides in length and includes thermodynamically favorable interspersed mis-matches which are not complementary to corresponding nucleotides in the target sequence within the mRNA molecule, with all remaining nucleotides in the second sequence being 100% complementary to the target sequence wherein the second sequence comprises a cleavage independent oligonucleotide that is cleavage independent at the RNA-induced silencing complex (RISC) complex; wherein the first sequence and the second sequence are located on the same RNA interference expression cassette;
   (g) incorporating said cassette into a delivery vehicle; and
   (h) providing a patient with an effective amount of the delivery vehicle.

2. The method of claim 1, wherein the normal tissue is extracted from an area in close proximity to the cancer tissue.

3. The method of claim 1, wherein the cancer and normal tissue is extracted using laser capture microdissection.

4. The method of claim 1, wherein the protein expression profile is obtained using 2D DIGE and mass spectrometry.

5. The method of claim 1, wherein a protein expression level must be at least two-fold higher in cancer tissue than in normal tissue to be considered an over-expressed protein.

6. The method of claim 1, wherein the delivery vehicle is selected from the group consisting of immunoliposomes, immunolipoplexes, RGD targeted nanoparticles, RGD targeted liposomes, nanoparticles, aptamers, dendrimers, chitosan, pegylated chitosan and oncolytic viral vectors.

7. The method of claim 1, further comprising measuring whether the RNA interference expression cassette is capable of suppressing the expression of one or more genes that encode the at least one prioritized protein in vitro prior to providing said delivery vehicle to a patient.

8. The method of claim 7, further comprising measuring whether the at least one prioritized protein exhibits a reduced expression level after provision of said delivery vehicle to the patient.

9. The method of claim 1, wherein the RNA interference expression cassette comprises a tumor-specific promoter.

10. A method for treating cancer, which comprises:
    (a) obtaining a specimen of cancer tissue and normal tissue from a patient;
    (b) extracting total protein from the cancer tissue and normal tissue;
    (c) obtaining a protein expression profile of the cancer tissue and normal tissue using 2D DIGE and mass spectrometry;

(d) identifying one or more over-expressed proteins in the cancer tissue, wherein a protein is considered to be over-expressed if the protein is found in the cancer tissue at higher levels than in the normal tissue;
(e) identifying at least one prioritized protein from the one or more over-expressed proteins, wherein the prioritized protein is translated from an mRNA molecule that will serve as a target for an RNA interference molecule;
(f) designing an RNA interference expression cassette to modulate the expression of at least one or more genes that encode the mRNA molecule from which the at least one prioritized protein is translated, wherein the RNA interference expression cassette encodes one or more RNA molecules that include:
(i) a shRNA that comprises a first sequence that is about 19-24 nucleotides in length and is 100% complementary to a target sequence within the targeted mRNA wherein the first sequence comprises a cleavage dependent oligonucleotide that is cleavage dependent at a RNA-induced silencing complex (RISC) complex; and
(ii) wherein the shRNA further comprises a second sequence that is about 19-24 nucleotides in length and includes thermodynamically favorable interspersed mis-matches which are not complementary to corresponding nucleotides in the target sequence within the targeted mRNA, with all remaining nucleotides in the second sequence being 100% complementary to the target sequence wherein the second sequence comprises a cleavage independent oligonucleotide that is cleavage independent at the RNA-induced silencing complex (RISC) complex; wherein the first sequence and the second sequence are located on the same RNA interference expression cassette;
(g) incorporating said cassette into an appropriate delivery vehicle, wherein the delivery vehicle is an immunoliposome; and
(h) providing a patient with an effective amount of the delivery vehicle.

* * * * *